United States Patent
De La Huerga

(10) Patent No.: US 7,107,281 B2
(45) Date of Patent: *Sep. 12, 2006

(54) METHOD FOR STORING RECORDS AT EASILY ACCESSIBLE ADDRESSES

(75) Inventor: Carlos De La Huerga, Milwaukee, WI (US)

(73) Assignee: HyperPhrase Technologies, LLC, Madison, WI (US)

( * ) Notice: Subject to any disclaimer, the term of this patent is extended or adjusted under 35 U.S.C. 154(b) by 606 days.

This patent is subject to a terminal disclaimer.

(21) Appl. No.: 10/188,420

(22) Filed: Jul. 2, 2002

(65) Prior Publication Data

US 2002/0174105 A1 Nov. 21, 2002

Related U.S. Application Data

(63) Continuation-in-part of application No. 09/326,177, filed on Jun. 4, 1999, now Pat. No. 6,434,567, which is a continuation-in-part of application No. 09/247,349, filed on Feb. 10, 1999, now Pat. No. 7,013,298, which is a continuation-in-part of application No. 08/727,293, filed on Oct. 9, 1996, now Pat. No. 5,895,461, and a continuation-in-part of application No. 08/871,818, filed on Jun. 9, 1997, now Pat. No. 5,903,889, said application No. 10/188,420, and a continuation-in-part of application No. 09/130,934, filed on Aug. 7, 1998, now Pat. No. 6,345,268.

(60) Provisional application No. 60/023,126, filed on Jul. 30, 1996.

(51) Int. Cl.
*G06F 17/30* (2006.01)

(52) U.S. Cl. .............................. 707/102; 707/1; 707/3; 707/10; 707/104.1

(58) Field of Classification Search ...................... 707/1, 707/3, 10, 102, 104.1
See application file for complete search history.

(56) References Cited

U.S. PATENT DOCUMENTS

| | | | |
|---|---|---|---|
| 4,864,501 A | | 9/1989 | Kucera et al. |
| 4,887,212 A | | 12/1989 | Zamora et al. |
| 4,994,966 A | | 2/1991 | Hutchins |
| 5,161,223 A | * | 11/1992 | Abraham ........................ 707/3 |
| 5,161,225 A | * | 11/1992 | Abraham et al. ........ 707/103 R |
| 5,218,697 A | | 6/1993 | Chung |
| 5,291,399 A | | 3/1994 | Chaco |
| 5,361,346 A | | 11/1994 | Panesar et al. |
| 5,379,424 A | * | 1/1995 | Morimoto et al. .............. 707/2 |
| 5,392,386 A | | 2/1995 | Chalas |
| 5,434,974 A | | 7/1995 | Loucks et al. |

(Continued)

FOREIGN PATENT DOCUMENTS

| | | |
|---|---|---|
| GB | 2154344 A | 9/1985 |
| WO | WO 01/33432 A1 | 5/2001 |
| WO | WO 01/35714 A2 | 5/2001 |

OTHER PUBLICATIONS

Microsoft Corporation, Microsoft Word 97, Screen printouts, pp. 1–4, 1997.

(Continued)

*Primary Examiner*—Frantz Coby
(74) *Attorney, Agent, or Firm*—Quarles & Brady LLP

(57) ABSTRACT

A method for identifying record segments that are to be stored for subsequent access and linking within other records. The method includes earmarking a record segment with a data reference and thereafter storing an address corresponding to the earmarked segment along with the data reference so thereafter when the data reference is recognized within another record, a link can be made between the data reference in the other record and the record segment stored at the address associated therewith.

44 Claims, 27 Drawing Sheets

U.S. PATENT DOCUMENTS

| | | | |
|---|---|---|---|
| 5,438,655 A | | 8/1995 | Richichi et al. |
| 5,515,534 A | | 5/1996 | Chuah et al. |
| 5,558,638 A | | 9/1996 | Evers et al. |
| 5,581,460 A | | 12/1996 | Kotake et al. |
| 5,740,252 A | | 4/1998 | Minor et al. |
| 5,745,360 A | | 4/1998 | Leone et al. |
| 5,745,908 A | | 4/1998 | Anderson et al. |
| 5,761,436 A | | 6/1998 | Nielsen |
| 5,764,906 A | | 6/1998 | Edelstein et al. |
| 5,794,050 A | | 8/1998 | Dahlgren et al. |
| 5,822,539 A | | 10/1998 | van Hoff |
| 5,833,599 A | | 11/1998 | Schrier et al. |
| 5,860,136 A | | 1/1999 | Fenner |
| 5,867,562 A | | 2/1999 | Scherer |
| 5,867,821 A | | 2/1999 | Ballantyne et al. |
| 5,878,421 A | | 3/1999 | Ferrel et al. |
| 5,884,302 A | | 3/1999 | Ho |
| 5,895,461 A | * | 4/1999 | De La Huerga et al. ........ 707/1 |
| 5,903,889 A | * | 5/1999 | de la Huerga et al. .......... 707/3 |
| 5,905,866 A | | 5/1999 | Nakabayashi et al. |
| 5,905,991 A | | 5/1999 | Reynolds |
| 5,940,843 A | | 8/1999 | Zucknovich et al. |
| 5,942,986 A | | 8/1999 | Shabot et al. |
| 5,963,205 A | | 10/1999 | Sotomayor |
| 5,963,950 A | | 10/1999 | Nielsen et al. |
| 5,970,505 A | | 10/1999 | Ebrahim |
| 5,974,413 A | | 10/1999 | Beauregard et al. |
| 5,987,475 A | | 11/1999 | Murai |
| 6,014,677 A | | 1/2000 | Hayashi et al. |
| 6,031,537 A | | 2/2000 | Hugh |
| 6,038,573 A | | 3/2000 | Parks |
| 6,094,649 A | | 7/2000 | Bowen et al. |
| 6,128,635 A | | 10/2000 | Ikeno |
| 6,141,663 A | | 10/2000 | Hunkins et al. |
| 6,151,624 A | | 11/2000 | Teare et al. |
| 6,157,914 A | | 12/2000 | Seto et al. |
| 6,178,434 B1 | | 1/2001 | Saitoh |
| 6,188,751 B1 | | 2/2001 | Scherer |
| 6,272,505 B1 | | 8/2001 | De La Huerga |
| 6,345,268 B1 | * | 2/2002 | de la Huerga ................. 707/3 |
| 6,434,567 B1 | * | 8/2002 | De La Huerga ............ 707/102 |
| 6,795,817 B1 | * | 9/2004 | Agarwal et al. ................ 707/2 |

OTHER PUBLICATIONS

Glinert, A Pumped–Up Publishing Pro, Apr. 1997, Computer Shopper, p. 462.
Goodman, Web Documents Without HTML, Arp. 1997, Computer Shopper, p. 412.
Marshall, Acrobat, Common Ground Extend Reach Beyond Document Viewing, InfoWorld, Apr. 21, 1997, p. 105.
Weibel, Publish To Paper And The Web, Dec. 1996, PC/Computing, p. 130.
"Automated Hypermedia Link Generation", IBM Technical Disclosure Bulletin, Jun. 1992, pp. 447–449.
"Glossary of Terms", attribution unknown, Jul. 18, 1999, pp. 1–6.
"Link Class Hierarchy Design", IBM Technical Disclosure Bulletin, vol. 34, No. 9, Feb. 1992, pp. 166–167.
"Multimedia Hyperlinks Automatically Created for Reference Documents", IBM Technical Disclosure Bulletin, PubNo.=350, Jun. 1993.
Weibel, "Publish to Paper and the Web", Computing, vol. 9, Dec. 1996, p. 130.
"Text Formatting Rules", attribution and date unknown, c2.com/cgi/wiki?TextFormattingRules printed May 28, 2003, pp. 1–3.
"Turbo Pascal, Version 1.5 Demonstration", Microsoft evidence, 2003, pp. 1–4.
"U: Telecoms/Electronic mail/LANS", Current Awareness Abstracts, Oct. 1995, aslib.co.uk/caa/abstracts/open/95–1505.html, printed Apr. 10, 2003.
"User Generated Hypertext Links", IBM Technical Disclosure Bulletin, vol. 38, No. 10, Oct. 1993, pp. 453–454.
Z. Li et al, "Hypermedia Links and Information Retrieval", University of Southampton, attribution and date unknown, pp. 1–11.
"What is Wiki", date unknown, http://wiki.org/wiki.cgi-?WhatIsWiki, p. 1.
"Wiki History", date unknown, last edited May 21, 2003, pp. 1–4.
"Wikipedia WikiWiki", date unknown, wiki.org. pp. 1–3.
A. F. Fountain et al, "MICROCOSM: An Open Model for Hypermedia with Dynamic Linking", Hypertext: Concepts, Systems, and Applications, Proceedings of the First European Conference on Hypertext. INRIA<France, Nov. 1990, pp. 289–311.
A. Salminen et al, "From Text to Hypertext by Indexing", ACM Transactions on Information Systems, vol. 13, No. 1, Jan. 1995, ACM 1046–8188/95/0100–0069 $3.50, c. 1995, pp. 69–99.
B. Goodman, "Web Documents Without HTML", Computer Shopper, Apr. 1997, p. 412.
B. J. Rhodes, et al, "Remembrance Agent: A Continuously Running Automated Information Retrieval System", Proceedings of the First International Conference on the Practical Application of Intelligent Agents and Multi–Agent Technology, Apr. 22–24, 1996, pp. 487–495.
B. Rhodes et al, "The Wearable Remembrance Agent: A System for Augmented Memory", The Proceedings of the First International Symposium on Wearable Computers (ISWC '97) Cambridge, MA, Oct. 1997 pp. 1–10.
C. Bailey et al, "An Agent–Based Approach to Adaptive Hypermedia Using a Link Service", Adaptive Hypermedia abnd Adaptive Web–Based Systems International Conference, AH 2000, Trento, Italy, Aug. 2000, eprints.ecs.soton.ac.uk/archive/00004465/02/ah2000.html.
C. H. Franke III, "Authoring a Hypertext UNIX Help System", Proceedings of ACM Conference on Computer Science, ACM 0–897971–737–5, c. 1995, pp. 238–245.
C. Keep et al, "Intermedia", The Electronic Labyrinth, copyright 1993–2000, pp. 1–2.
D. F. Brailsford, "Experience with the Use of Acrobat in the CVAJUN Publishing Project", ECHT '94 Proceedings, Sep. 1994 pp. 228–232.
D. Raymond et al, "Hypertext and the Oxford English Dictionary", Communications of the ACM, vol. 31m No. 7, Jul. 1988, pp. 871–879.
D. T. Change, "HieNet: A User–Centered Approach for Automatic Link Generation", Hypertext '93 Proceedings, Nov. 1993, pp. 145–158.
E. Wilson, "A Guide to Justus: An Overview of a Hypertext Legal Database", 5th BILETA Conference British and Irish Legal Technology Association, lileta.ac.uk/90papers/wilson.html, pp. 1–13, printed Apr. 11, 2003.
E. Wilson, "A Hypertext Interface for Automated Document Drafting", Law Technology Journal, vol. 1, No. 1, Oct. 1991 law.warwick.ac/itj/1–1e.html , pp. 1–14 printed May 29, 2003.

E. Wilson, "Cases for Justus" Preparing a Case Database for a Hypertext Information Retrieval System, Literary & Linguistic Computing, vol. 5, No. 1, 1990, Oxford University Press 1990, pp. 119–128.

E. Wilson, "Electronic Books: The Automatic Production of Hypertext Documents from Existing Printed Resources", attributed to Proceedings of the Fourth Annual Conference of the UW Centre for New Oxford English Dictionary, Information in Text, Waterloo, 1988, pp. 29–45.

E. Wilson, "Guiding Lawyers: Mapping Law into Hypertext", Artificial Intelligence Review 6, 1992, pp. 161–189.

E. Wilson, "Integrated Information Retrieval for Law Enforcement in a Hypertext Environment" ACM Portal — Portal.acm.org/citation.cfm?id=62505&coll=ACM&dl= ACM&CFID=11032774&CFTOKEN . . . , Jun. 25, 2003.

E. Wilson, "Integrated Information Retrieval for Law in a Hypertext Environment", Annual ACM Conference on Research and Development in Information Technology, 1988, pp. 663–677, ACM Portal, Portal.acm.org/citation.cfm?id=62505&coll=ACM&CFID=11032774& CFTOKEN . . . , Jun. 25, 2003.

E. Wilson, "Integrated Information Retrieval for Law in a Hypertext Environment", attributed to Proceedings of the SIGIR/ACM International Conference on Research and Development in Information Retrieval, 1988, ACM 0–89791–274–B 88 06500 0663 $1.50, c 1988, pp. 663–677.

E. Wilson, "Links and Structures in Hypertext Databases for Law", Proceedings of the First European Conferences on Hypertext, INRIA, France, Nov. 1990, pp. 194–211.

E. Wilson, "Reference and Reference Inversion in Statutes and Cases: a Hypertext Solution", attributed to Informatics 10, 1989, Cisti Product Help 9919308 to 16173682126, printed Mar. 4, 2003.

G. Crane, "From the Old to the New: Integrating Hypertext into Traditional Scholarship", Hypertext '87 Papers, Nov. 1987, pp. 51–55.

G. Hill et al, Applying Open Hypertext Principles t the, University of Southampton, attribution and date unknown, pp. 1–19.

G. Hill et al, "Extending the Microcosm Model to a Distributed Environment", ECHT '94 Proceedings, copyright 1994 ACM 0–89791–640–9/94/0009/$3.50, pp. 32–40.

G. Hill et al, "Microcosm and the. A Distributed Link Service", 1995/1996 Research Journal, University of Southampton,, pp. 1–6.

G. Hill et al, "Open and Reconfigurable Hypermedial Systems: A Filter–Based Model", CSTR 92–12, University of Southampton, pp. 1–17.

G. Hill, et al, Applying Open Hypertext Principles to the, attribution and date unknown, University of Southampton.

G. Krupka, "SRA: Description of the SRA System as Used for MUC–6", attributed to the Proceedings of MUC–6 Workshop, 1995, pp. 221–374.

G. Perlman, "Information Retrieval Techniques for Hypertext in the Semi–Structured Toolkit", Hypertext '93 Proceedings, Nov. 1997, pp. 260–267.

G. Salton et al, "Automated Analysis, Theme Generation, and Summarization of Machine–Readable Texts", Science, vol. 264, Jun. 3, 1994, pp. 1421–1426.

H. Davis et al, "A Framework for Delivering Large–Scale Hypermedia Learning Material", attribution and date unknown.

H. Davis et al, "Hypermedia and the Teaching of Computer Science: Evaluation an Open System.", attribution and date unknown, University of Southampton, pp. 1–8.

H. Davis et al, "Media Integration Issues within Open Hypermedia Systems", attribution and date unknown.

H. Davis et al, "Microcosm: A Hypermedia Platform for the Delivery of Learning Materials", CSTR 93–10, University of Southampton pp. 1–11.

H. Davis et al, "MICROCOSM: An Open Hypermedia Environment for Information Integration.", CSTR 92–15, University of Southampton, pp. 1–18.

H. Davis et al, "Towards an Integrated Information Environment with Open Hypermedia Systems", ACM, Milano, Nov. 30–Dec. 4, 1996 p. 181–190.

H. J. Love, "Using Agent–Based Technology to Create a Cost Effective, Integrated, Multimedia View of the Electronic Medical Record", Symposium on Computer Applications in Medical Care, Oct. 28 to Nov. 1, 1996, New Orleans, pp. 441–444.

H. Kaindl et al, "Semiautomatic Generation of Dictionary Links in Hypertext", Submitted to DIS '95, Feb. 1, 1995, pp. 1–14.

J. Allen, "Automatic Hypertext Construction", PhD. Dissertation Cornell University, Jan. 1995.

J. Allen, "Automatic Hypertext Link Typing", ACM Proceedings for the Hypertext '96 Conference, Washington D.C., Mar. 1996, pp. 42–52.

J. Naughton, "Putting the Turbo in Pascal", Hardcopy, Jan. 1985, vol. 14, No. 1.

J. Robertson et al, The Hypermedia Authoring Research Toolkit (HART), Attributed to Proceedings of the European Conference on Hypertext, ACM 0–8791–640–9/94/0009/ $3.50, Sep. 1994. pp. 177–185.

K. E. Willard et al, "W3 based Medial Information Systems vs Custom Client Server Applications", UNIV_MINN_W#_PAPER, http://archive.ncsa.uinc.edu/SDG/IT($/Proceedings/MedTrack/willard/UMHC_UMHC_paper . . . , date unknown, pp. 1–6 printed Jun. 4, 2003.

K. Osterbye et al, "The Flag Taxonomy of Open Hypermedia Systems", ACM Hypertext '95 Washington DC, 1996 ACM 0–89791–778–2/96/03 . . . $3.50, pp. 129–139.

K. W. Church et al, "Commercial Applications of Natural Language Processing", Communications of the ACM, v.38, n. 11, Nov. 1995, pp. 71–79 ISSN: 0001–0782, printed Mar. 13, 2003.

L. Carr, "The Microcosm Link Service and its Application to the World Wide Web", attribution and date unknown.

M. Bernstein, "An Apprentice That Discovers Hypertext Links", attribution and date unknown, pp. 212–223.

M. Bieber, "Issues in Modeling a "Dynamic" Hypertext Interface for Non–Hypertext Systems", Hypertext '91 Proceedings, Dec. 1991, pp. 203–217.

L. N. Garrett et al, "Intermedia: Issues, Strategies, and Tactics in the Design of a Hypermedia System", ACM CSCW, 1986, pp. 163–174.

Lotus, "Application Developer's Reference" Lotus Notes Release 3, copyright 1993, pp. 6–24 to 6–25.

Lotus, "Getting Started with Application Development", Lotus Notes Server for Windows Release 3, copyright 1993, pp. i. to 2–15.

L. N. Garrett et al, "Intermedia: Issues, Strategies, and Tactics in the Design of a Hypermedia Documents System", Proceedings of the 1986 ACM Conference on Computer-supported Cooperative Work, 1986, pp. 163–174, ACM Portal, Portal.acm.org/citation.cfm?id=62505&coll=ACM&Dl=ACM&CFID=11032774&CFTOKEN . . . , Jun. 25, 2003.

M. Bieber, "Providing Information Systems with Full Hypermedia Functionality", Working Paper Series Stern IS–92–29, Oct. 1992, pp. 2–13, printed May 16, 2003.

.P. Lissack, "Concept Sampling—A New Twist For Content Analysis", attribution and date unknown, pp. 1–40.

Microsoft Word 97 SR–2, demonstration pages, Microsoft exhibit, 2003.

N. Garrett, "Hypermedia: Issues, strategies, and Tactics in the Design of a Hypermedia System", ACM Portal Portal.acm.org/citation.cfm?id=637090&coll=ACM&dl=ACM&CFID=11034774&CFTOKEN . . . , Jun. 25, 2003.

P. Evans, "Speaking the Same Language", PC User, Issue 193, Sep. 22, 1992, pp. 57–58.

P. H. Lewis et al, "Content Based Retrieval and Navigation with Images in the Microcosm Model", University of Southampton, attribution and date unknown, pp. 1–5.

P. H. Lewis, et al, "Media–based Navigation with Generic Links", ACM Hypertext '96, Washington DC, pp. 215–223.

P. J. Brown, "A Help System Based on UNIX Manual Pages", date unknown, dcs.ex.ac.uk/~brown/guide/spe.guide.help.html, printed Apr. 24, 2003.

P. J. Brown, "A Simple Mechanism for Authorship of Dynamic Documents", attribution and date unknown, pp. 34–42.

P. J. Brown, "GUIDE User Manual", Copyright 1985, Sixteenth Impression, Apr. 1995.

P. J. Brown, "Turning Ideas into Products: The Guide System", Hypertext '87 Papers, Nov. 1987, pp. 33–40.

P. J. Brown, "UNIX Guide: Lessons from Ten Years Development", ACM Milano, Nov. 30–Dec. 4, 1992, pp. 63–70.

P. Marshall, "Acrobat Common Ground Extend Reach Beyond Document Viewing", Info World Apr. 21, 1997, p. 105.

P. N. Smith, "Journal Publishing with Acrobat: the CAJUN Project", Electronic Publishing. vol. 6(4), Dec. 1993, 481–493.

P. Thistlewaite, "Automatic Construction and Management of Large Open Webs", Information Processing & Management, vol. 33, No. 2, 1997, pp. 161–173.

P. Tyrvainen, "On Domain Modeling for Technical Documentation Retrieval", PhD Dissertation University of Technology (Espoo, Finland), Mar. 15, 1994, Published: Acta Polytechnica Scandinavica. 1994. pp. 1–163.

R. Hollom et al, "Integrating Internet Resource Discovery Services with Open Hypermedia Systems", CSTR 93–18, University of Southampton, pp. 1–18.

R. Wilkins et al, "A Direct Communication Model for Process management in an Open Hypermedia System", CSTR 93–14, University of Southampton, pp. 1–19.

Resource Workshop, Windows Programming Guide, Borland, c. 1991.

S. Ball, "New Approaches to Custom Interfaces", Attributed to Proceedings of the AUUG 95, 1995, csu.edu.au/special/conference/apwww95/papers95/sball/sball.html, pp. 1–11, printed May 5, 2003.

P. Thistlewaite et al, "Managing Large Hypermedia Information Bases: A Case Study Involving the Australian Parliament", Proceedings of AusWeb95 The First Australian World Wide Web Conference, Apr. 30 to May 2, 1995, pp. 223–227.

P. Thistlwaite, "Hypermedia in the Australian Parliament", web.archive.org/web/19970129035318//pastime.an-u.edu.au/pbt/hypermedia.html, date unknown, pp. 1–8 printed Apr. 11, 2003.

S. Glinert, "A Pumped–Up Publishing Pro", Computer Shopper, Apr. 1997, pp. 462.

S. Goose et al, "An Architecture to Support an Open Distributed Hypermedia System", University of Southampton, 1995/1996 Research Journal, pp. 1–7.

S. Huffman et al, "Notes Explorer Entity–Based Retrieval in Shared, Semi–Structured Information Spaces", Proceedings of the ACM CIKM 96, Rockville MD, ACM 0–89791–873–8/96/11, c. 1996, pp. 99–106

Matalon/S. Andrew, "Online Visits—Stump World Systems—", attributed to http://stumpworld.com/stump, Oct. 18, 1995.

S. Probets et al, "Dynamic Link inclusion in Online PDF Journals", attribution and date unknown pp. 1–14.

T. Joachims et al, "WebWatcher: A Tour for the World Wide Web", Proceedings of the International Joint Conference on Artificial Intelligence, 1997, citeseer.nj.nec.com/63787/16829. pp. 1–6 printed Jun. 4, 2003.

T. Starner et al, "Wearable Computing and Augmented Reality", M.I.T. Media Lab Vision and Modeling Group Technical Report No. 355, Nov. 1995, pp. 1–9.

Turbo Debugger for Windows, Resource Workshop User's Guide, Borland, c. 1991.

Turbo Pascal 1.5, Borland, c. 1992.

Turbo Pascal for Windows, Borland, c. 1998.

Turbo Pascal for Windows, Programmers Guide, Borland, c. 1987.

Turbo Pascal for Windows, Turbo Debugger for Windows, V.3.1 User's Guide, Borland, c. 1988 & 1992.

Turbo Pascal for Windows, User's Guide, Borland, c. 1987. 1991.

Turbo Pascal for Windows, Windows Reference Guide, Borland, c. 1991.

V. Bush, "As We May Think", Atlantic Monthly, Jul. 1945, theatlantic.com/unbound/flashbks/computer/bushf.htm, pp. 1–19 printed Jun. 24, 2003.

W. Fitzgerald et al, "Using natural Language Processing to Construct Large–Scale Hypertext Systems", submitted to the Eighth Knowledge Acquisition for Knowledge–Based Systems Workshop. Banff. Canada. Jan. 30 to Feb. 4, 1994.

W. Hall et al, "Linking the World Wide Web and Microcosm", attribution and date unknown, pp. 1–5, printed Jun. 4, 2003.

W. Hall et al, "Multimedia Teaching with Microcosm–HiDED: Viceroy Mountbatten and the Partition of India", attribution and date unknown, pp. 89–99.

W. Hall et al, "The Design and Implementation of an Open Hypermedia System", CSTR 92–19, University of Southampton, pp. 1–15.

W. Hall, "The History of the Microcosm Project", attribution and date unknown, Multimedia Research Group, pp. 1–6.

Information—Paul Thistlewaite; Jun. 4, 2003; 2 pages; cs.anu.edu.au/people/Paul.Thistlewaite/.

Wiki: Welcom Visitors; wiki.org/; May 28, 2003.

* cited by examiner

| Relevant Device/Application For Data Type $j$ ||
|---|---|
| Device/Application | IRS Information Provided |
| ICD - 1 | ARS; RRS |
| ICD -2 | ARS; RRS |
| ICD - 3 | ARS; RRS; DR |
| ⋮ | ⋮ |
| PC -1 | ARS; RRS |
| PC - 2 | ARS; RRS; DR |
| ⋮ | ⋮ |
| DB Literate Processor | ARS; DR |
| ⋮ | ⋮ |

Fig. 5

| DR | Address |
|---|---|
| DR - 1 | Add - 1 |
| DR - 2 | Add - 2 |
| ⋮ | ⋮ |
| "42° View" | Add - P |
| "68° View" | Add - Q |
| "135° View" | Add - R |
| ⋮ | ⋮ |
| DR - (N-1) | Add - (N-1) |
| DR - N | Add - N |
| ⋮ | ⋮ |

| Terminal Descriptor Definition Table | |
|---|---|
| ECG | Temporal Descriptor Definition |
| ⋮ | ⋮ |
| DR - N | Temporal Descriptor - N |

Fig. 28

| Temporal Descriptor Definition (for ECG DR) | |
|---|---|
| MR List | Temporal Rule Set (TRS) |
| Admission | Prior to Event Time Range (PRTR) |
| | Post Event Time Range (POTR) |
| | Resolving Rule (RR) |
| Discharge | PRTR - 2 |
| | POTR - 2 |
| | RR - 2 |
| MR - 3 | PRTR - 3 |
| | POTR - 3 |
| | RR - 3 |
| ⋮ | ⋮ |
| MR - N | PRTR - N |
| | POTR - N |
| | RR - N |
| No Match | No Match Rules |

Fig. 29

METHOD FOR STORING RECORDS AT EASILY ACCESSIBLE ADDRESSES

CROSS-REFERENCE TO RELATED APPLICATIONS

This application is a continuation-in-part of U.S. patent application Ser. No. 09/326,177 which was filed on Jun. 4, 1999 now U.S. Pat. No. 6,434,567 and is entitled "Method For Specifying Enterprise-Wide Database Address Formats" which is a continuation-in-part of U.S. patent application Ser. No. 09/247,349 which was filed on Feb. 10, 1999 now U.S. Pat. No. 7,013,298 and is entitled "Method and System for Automated Data Storage and Retrieval" which is a continuation-in-part of U.S. patent application Ser. No. 08/727,293 which was filed on Oct. 9, 1996 now U.S. Pat. No. 5,895,461 and is entitled "Method and System for Automated Data Storage and Retrieval With Uniform Address Scheme" which in turn claims priority from provisional Appln. Ser. No. 60/023,126 which was filed on Jul. 30, 1996, the Ser. No. 09/247,349 application also being a continuation-in-part of U.S. patent application Ser. No. 08/871,818 which was filed on Jun. 9, 1997 now U.S. Pat. No. 5,903,889 and is entitled "System and Method for Translating, Collecting and Archiving Patient Records". This application is also a continuation-in-part of U.S. patent application Ser. No. 09/130,934 which was filed on Aug. 7, 1998 now U.S. Pat. No. 6,345,268 and is entitled "Method and System for Resolving Temporal Descriptions of Data Records in a Computer System".

STATEMENT REGARDING FEDERALLY SPONSORED RESEARCH OR DEVELOPMENT

Not applicable.

BACKGROUND OF THE INVENTION

The present invention relates to the collection, storage and retrieval of data on computer systems. More particularly, the present invention relates to a method and apparatus for specifying address formats and rule sets for creating address formats for use throughout an information enterprise which facilitate automatic address building and storage for collected records and automatic generation of hyperlinks to stored records via database literate processors.

An exemplary information enterprise includes at least one database (DB), information collecting devices (ICDs) for collecting information to form data records for storage on the DB and one or more processors linked to the DB for running application programs which access and manipulate DB records. For example, U.S. patent application Ser. No. 09/170,169 (hereinafter "the '169 application") entitled "Data Collection Device and System," which is commonly owned by the applicant of this application, describes several remote ICD types which collect information and provide the information and corresponding addresses to a DB for storage. For the purposes of this explanation ICDs may also include stationary computers or the like for data entry. U.S. patent application Ser. No. 09/247,349 (hereinafter "the '349 application) entitled "Method and System for Automated Data Storage and Retrieval" which is commonly owned by the applicant of this application, describes a database literate processor application program which automatically builds database addresses for forming hyperlinks between data references to records and the records referenced by the data references. The '349 application also teaches processors which receive information sets and based on set content, generate DB addresses for the sets and store the information sets at the generated addresses. Although the invention may be used with other application programs, to simplify this explanation the invention will be described in the context of the DB literate processor program referenced above. Hereafter DB literate processor is taken to mean any of several different types of data processors including a word processor, a spread sheet, a data entry form and so on.

The proliferation of information systems throughout all aspects of business and personal life is a clear sign that society has recognized the advantages associated with such systems. Nevertheless, conventional information systems are plagued by a number of important shortcomings which render systems difficult to use and therefore, in many cases, underutilized.

First, in most cases it is extremely difficult to develop and maintain an entire information system which is completely information compatible. Information compatibility means that when a record and a corresponding address are provided to the DB for storage, the record information is arranged in a record format required by the DB and the record address is in an address format required by the DB. Information compatibility also means that when a DB literate program identifies a DB record in a record request, the request includes an address format which is recognizable by the DB.

Generally there are two ways to facilitate information compatibility. First, each ICD program and DB literate program may be programmed to provide records and respective storage addresses in record formats and address formats required by the DB. Second, an intermediate computer may be provided which receives information from ICDs and DB literate programs and uses the received information to generate records and respective storage addresses which comport with required DB record and address formats. The intermediate computer effectively operates as a translator between the ICDs and DB literate programs on one hand and the DB on the other hand.

In either case, after a DB characterized by record formats and address formats has been defined, additional custom programming has to be done to support information compatibility. In systems which do not include an intermediate computer, each ICD program and DB literate program has to be programmed to support information compatibility. In the case of an ICD program, this means that the program can recognize information required to form a record and an address, can identify the required information and can assemble the address and record for delivery to the DB. In the case of a DB literate program, this means that the program can recognize a reference to a stored record, can recognize information required to form an address for the referenced record, can identify the required information and can assemble an address for the referenced record. In systems which include an intermediate computer, the computer has to be programmed to receive information from the ICDs and application programs, recognize information required to form a record and/or an address, identify the required information and assemble the record and/or address for delivery to the DB.

Thus, programming an ICD, a DB literate program, or an intermediate computer requires provision of DB address formats and record formats and rule sets for identifying required information to instantiate the formats, rule sets for how to use the identified information to instantiate the formats often including specific information forms and rules for converting the identified information into the specific information forms.

Therefore, conventional systems for defining DB address formats and record formats require at least two programming steps to facilitate information compatibility including DB definition and additional programming of either ICD programs and DB literate programs or additional programming of an intermediate computer.

While two step programming is not particularly difficult where ICDs and application programs are only used with one DB and where the DB only supports one record format and one address format, most information systems include several DBs and each DB typically supports several different record formats and address formats. In addition, most information systems also include many different ICD and application program types, each of which may internally format information in a unique manner and may provide information to an intermediate computer in a unique configuration. These different ICD and application program types further increase programming complexity.

This smorgasbord of different DBs, record formats, address formats, ICD types and application program types is due to the evolutionary nature of information systems generally. Typically information systems grow and expand along with the businesses they serve. For example, an initial system may include one type of ICD and a single application, each of which is supportable by a single programming language. As technology evolves a second ICD type may be developed and added to the system, the second ICD type having to be programmed for DB information compatibility and so on. Similarly, as a business expands, database requirements eventually exceed existing capacity and additional DBs have to be added to the information system. Many times a new DB requires different record formats and address formats. In addition, often different ICDs and applications only support a vendors proprietary software and record and addressing formats.

The second shortcoming of conventional information systems is related closely to the first and is that highly skilled programmers are typically required to facilitate information compatible programming. This is because such programming requires an intimate knowledge of DB record formats and address formats and the form in which ICDs internally store information. In addition, in systems which do not include an intermediate computer, the programmer must have knowledge about the ICD and DB literate program programming languages. In systems which have an intermediate computer the programmer must have knowledge about the intermediate computers programming language. The task of programming is further exacerbated in most cases as most information systems include many different ICD types, application program types and DBs having unique programming characteristics as described above.

Third, modifications to information systems are relatively difficult to implement. Consider the case where a new record format and a new address format are added to a DB or the case where an entirely new DB is added to an information system where the new DB requires new address formats and record formats. In either of these two cases additional customizing programming is required. In systems which do not include an intermediate computer each ICD program and each DB literate program has to be modified to accommodate the new DB record format(s) and address format(s). Also, new rule sets for identifying required information and for instantiating address formats and record formats have to be provided to each ICD and each DB literate program. In systems which include an intermediate computer the intermediate computer has to be reprogrammed to accommodate the new DB record format(s) and address format(s).

Fourth, because highly skilled programmers are required to support and maintain an information system and many businesses do not employ such programmers, often, despite a systems ability to support additional information gathering, storage, retrieval and processing capabilities, a business will not take advantage of such additional capabilities.

For example, in a medical facility ICDs including bar code readers may routinely be used to memorialize physician visits to patients. With a bar coded bracelet on each patient, at the beginning of each patient visit a physician may be required to use the ICD to read the patient's information from the bracelet. The ICD then generates a record including date, time, patient ID, physician ID and so on documenting a patient encounter. The ICD also generates a record address and, when downloaded to a DB, the DB stores the record at the corresponding address.

In this case, it may be advantageous to use the same bar code reading ICD to track other facility information. For example, facility equipment may be bar coded to track location of mobile equipment, medication containers may be bar coded when filled to track dispensation and so on. If the ICDs are used to track equipment location without custom programming equipment locations will be mistaken for patient encounters. Thus, custom programming is required. In this case, while the ICD may be ideal for other facility purposes, the programming task required to support these other capabilities may be prohibitively complex and therefore the additional capabilities may never be realized.

Fifth, especially in systems which include a large number of different devices, applications and DBS, program errors are extremely likely and, unfortunately, because of system complexity debugging is extremely difficult. For example, in the case of an ICD which generates both a data record and a corresponding address for the record from an information set and then downloads the record/address to a DB for storage, if a new record/address format pair is to be supported and each of the ICD and DB have to be programmed to support the new format separately, errors or incompatibilities between the DB and ICD are likely and identifying the errors would be difficult at best.

Therefore, it would be advantageous to have a method and apparatus which could be used to simplify the process of programming all of the components of an information system such that complete information compatibility can be achieved through a single programming process. It would also be advantageous if such a method and/or apparatus could ensure information compatibility.

BRIEF SUMMARY OF THE INVENTION

The present invention is to be used with a system which includes at least one and perhaps several different types of processing devices, each processing device capable of either generating a storage address for a record or generating and creating a link to record stored at a particular address or both storing and linking. To this end, each processing device requires, among other things, a database address format which can be used as a pattern for generate the storage or linking address.

The invention includes both a method and an apparatus for specifying enterprise wide address formats for the use by all processing devices for address generating purposes. To this end, the inventive method includes the steps of specifying required address formats including a plurality of fields, for each format field, specifying a field type and providing the address format to the processing devices for storing and linking processes. To facilitate field type specification, the system preferably includes pre-defined field types which have been designed specifically for the facility which employs the invention and which, to that end, are defined to be the field types most likely to be routinely used at the facility.

In systems including many different types of processing devices, by specifying address formats once and then providing the formats to all processing devices, complete enterprise wide address compatibility is ensured.

In addition to including pre-defined address format field types, the invention also provides an instantiation rule set for each pre-defined field type which includes rules for identifying information to fill in or "populate" the corresponding field. For example, for a date field, the instantiation rule set indicates how to determine (e.g., the date format) in the address. As another example, for an "ECG" field, the instantiation rule set indicates how to determine if an information set or a data reference corresponds to an ECG and if so, how to format an ECG type address format for storage or linking purposes It has been recognized that in a completely information compatible system there are at least two common information threads which are present in the software required to operate each system DB, device and application and that, by providing tools and methods which exploit these common information threads, the processes of defining, maintaining and modifying DB record and address formats and associated rules can be simplified appreciably. By simplifying the DB management tasks, DB management can be accomplished by less skilled administrators, in less time and can take full advantage of all DB capabilities.

The two common information threads are unique field instantiation rule sets (IRSs) and data type definitions. With respect to field IRSs, virtually all records and corresponding addresses can be divided into distinct fields. For instance, an exemplary universal resource locator (URL) address comporting with the well-known hypertext markup language (HTML) of the Internet, for a medication administration record for a specific patient at a specific time is:

"http://hww.st_mary.springfield/medication/given/ 987654321/19_05_1996/13:42/repo rt.html" (hereinafter "the exemplary address")

Where "http://hww.st_mary.springfield" corresponds to a first field, "medication/given" corresponds to a second field, "987654321" corresponds to a third field and indicates a patient ID number, "19_05_1996" corresponds to a fourth field and indicates a date, "13:42" indicates a time and corresponds to a fifth field and "report.html" corresponds to a sixth field and indicates the record type stored at the address. For each field in the exemplary address, a data object having a specific form has to be provided to instantiate the field. Hereinafter, although many types of data objects (e.g. text, other characters, binary codes, etc.) may be used to instantiate a field, the invention will be described as using ASCII text character strings to instantiate fields. In addition, a field specific rule set for identifying information to instantiate the field has to be provided. Moreover, in many cases, a second rule set, referred to herein as a conversion rule set, has to be provided for converting identified information into the specific form required for instantiation. Obviously, specifying all of this information for each field in each address format supported by a system is an arduous task.

However, the common field thread is that most fields and corresponding IRSs (i.e. required field string gleaning rules and conversion rules) are used repetitively in many different address and record formats. This is particularly true in the case of a specialized facility where most information can generally be grouped by one or a small number of information segments. For example, in the case of the patient ID field (i.e. "987654321") in the exemplary address above, a large number of records and corresponding addresses at medical facility will include a patient ID field. Therefore, if an IRS is specified once for a patient ID field and is then stored as a "pre-defining" field IRS, each time a patient ID field is required in an address or a record format, the pre-defining field IRS can be used. Similar predefining field IRSs can be provided for date, time, report type, server location, event (e.g. medication/given, post-op_ecg, etc.) physician identification, and so on.

Thus, the present invention provides a method and apparatus for, in effect, "pre-defining" field IRSs which, therefore, can be used to easily and quickly specify new address and record formats.

In addition to expediting DB management tasks, pre-defining field IRSs force system wide information compatibility and thereby reduce and, in many cases, will even eliminate debugging requirements. This is because, after unique field IRS have been specified once, those unique IRSs are used for specific corresponding fields thereafter and hence every time the corresponding field is employed, the same field character string and rules are employed.

With respect to the data type definitions common thread, a data type definition includes standard data type definition information such as information defining the structure and type of information stored in the specific data type and defining relationships between the specific data type and other data types common to conventional data type definitions. In addition, according to an exemplary embodiment of the present invention, the data type definition also includes an address format, a record format and a unique data reference (DR) where the DR is used to refer to a record of the specific data type.

Typically, each of a system DB and at least one and more often many system devices and applications require at least a subset of data type definition information. Therefore, after being specified once, the data type definitions can simply be provided once to a relevant system DB and corresponding devices and applications. Thus, the present invention also provides a method and apparatus for specifying data type definitions, earmarking certain sections of each data type definition for provision to specific devices and applications and then downloading earmarked sections to the devices and applications.

Thus, one object of the invention is to provide a system including predefined address format fields and corresponding instantiation rule sets which can be used to quickly define address formats for use by an enterprise computing system.

Another object is to provide a system wherein address formats can be specified once for all processing devices (e.g. databases, servers, applications, data collection devices, etc.). In addition to reducing the time and effort required to support a new address format, this feature ensures enterprise wide address formatting compatibility.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 5 is a schematic diagram illustrating the device and application list of FIG. 2;

FIG. 25 is a schematic illustrating a DR reference table according to the present invention;

FIG. 28 is a schematic diagram of a temporal descriptor definition table according to the present invention;

FIG. 29 is a schematic diagram of an exemplary temporal descriptor definition of FIG. 28;

DETAILED DESCRIPTION OF THE INVENTION

Although the present invention is meant to be used in a plurality of different environments, in order to simplify this explanation, the invention will be described in the context of a medical facility named "St. Mary's, Springfield". In addition, the invention will be described in the context of a single record and data type definition corresponding thereto. The record is a medication administration record. In this regard, it will be assumed that it is desirable to record each medication administration including data, time, the patient receiving medication, the physician administering medication and the medication type administered.

A. System Hardware and Exemplary Database Definitions

Figure 1:
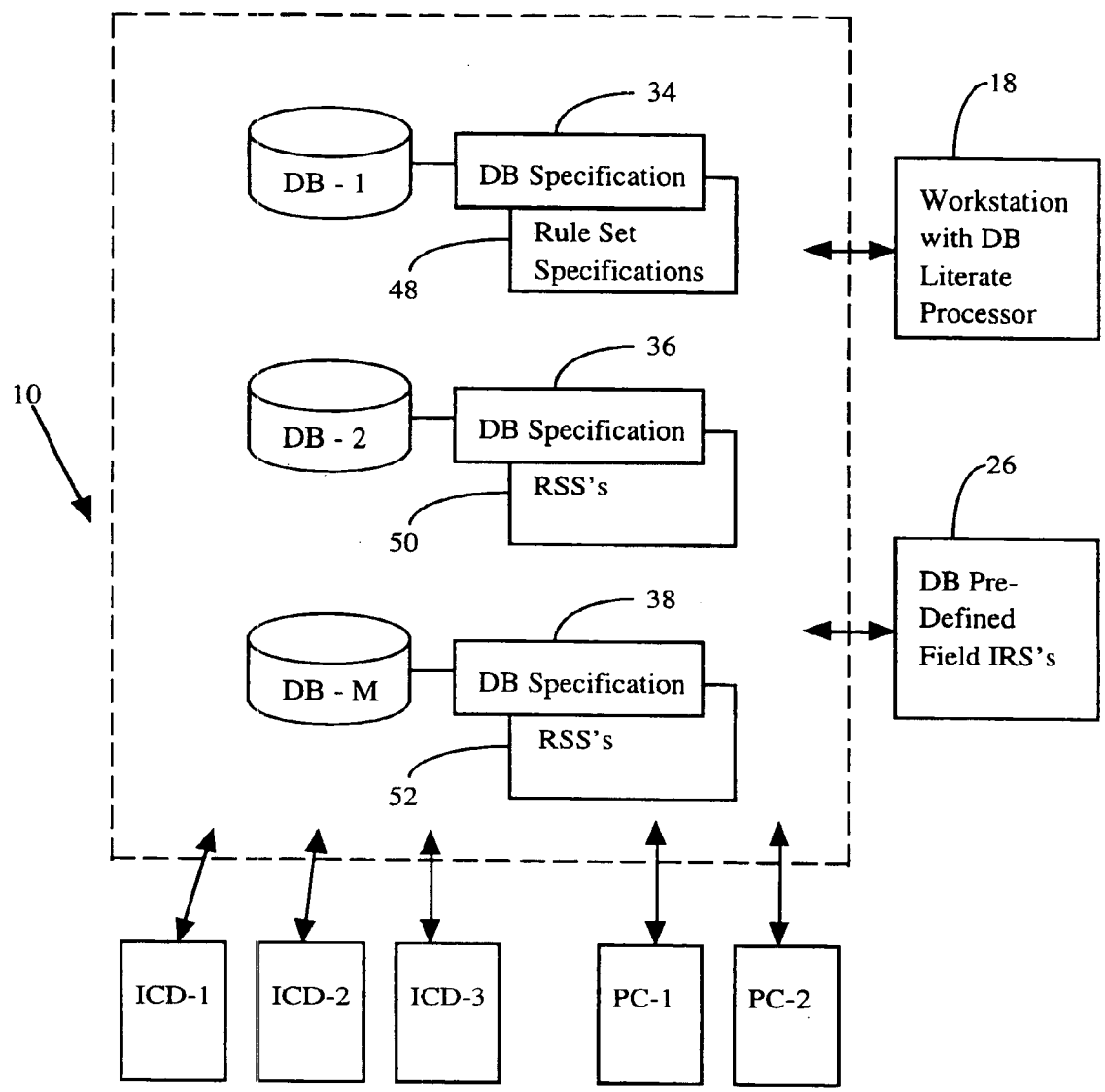
FIG. 1 is a schematic diagram of an exemplary information system according to the present invention.

Referring now to the figures wherein like reference characters represent similar components, systems and subsystems throughout the several views, and more specifically, referring to FIG. 1, therein is illustrated various components of an exemplary information system 10 including several databases DB-1, DB-2, . . . , DB-M, several personal computers PC-1, PC-2, a workstation 18 including a DB literate processor, several remote information collection devices (ICDs) ICD-1, ICD-2 and ICD-3 and a pre-defining field instantiation rule set (IRS) DB 26.

Figure 2:
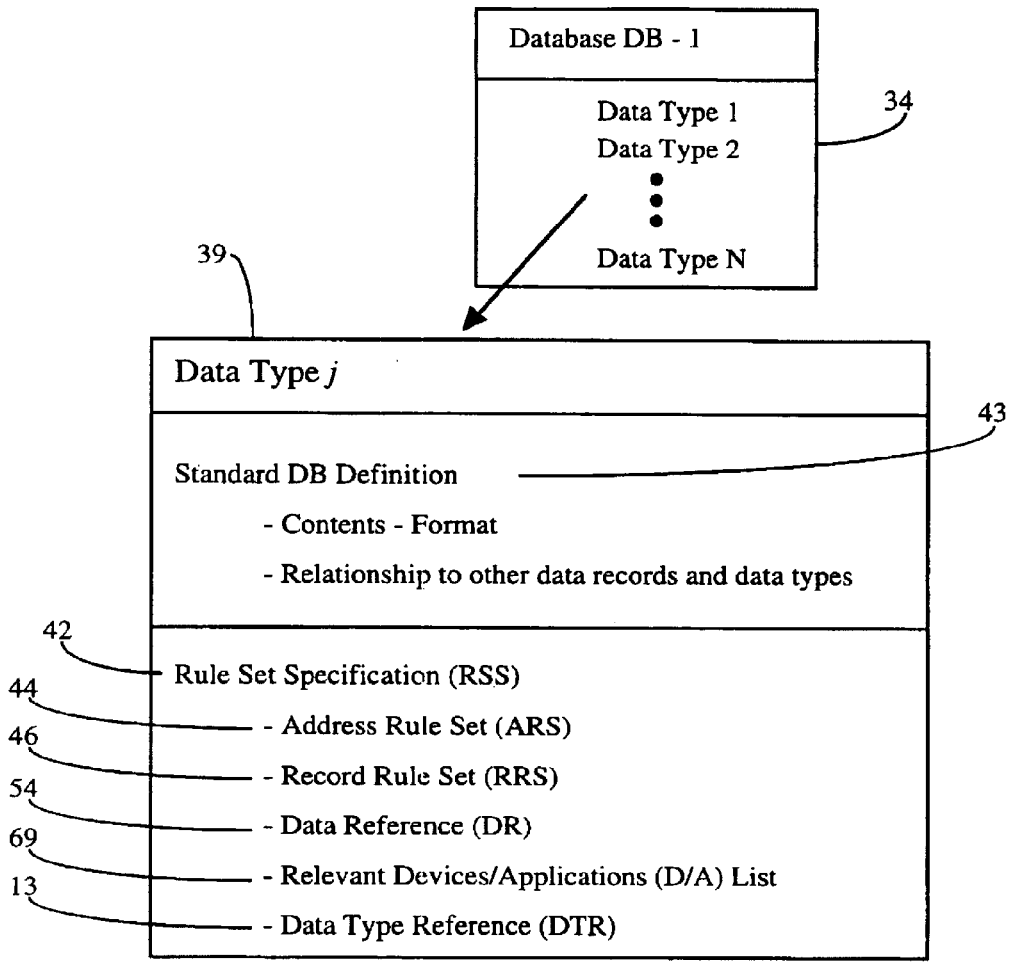
FIG. 2 is a schematic diagram of an exemplary database definition recorded in the present invention.

Each database DB-1, DB-2, DB-M, includes a DB specification 34, 36, 38, respectively. Referring also to FIG. 2, exemplary DB specification 34 corresponding to database DB-1 lists data types (1–N) which are stored in database DB-1. In addition, for each data type in database DB-1, specification 34 includes a database definition 39 having standard database definition information including DB content or format for records of the specification type and information specifying relationships of the specific data type records to other data records and data types. For example, for a data type j in specification 34, the standard database definition information is identified by numeral 43.

1. Rule Set Specification

Referring still to FIG. 2, for each data type (1–N), data type definition 39 also includes a rule set specification (RSS). Although RSSs constitute a portion of a DB specification, referring also to FIG. 1, RSSs 48, 50 and 52 are illustrated as distinct from corresponding DB specifications 34, 36, 38, respectively, to stress the fact that RSSs 48, 50, 52 are in addition to standard DB definition information (e.g. 43 in FIG. 2). RSSs 48 in FIG. 1 include, among other RSSs, RSS 42 in FIG. 2 which corresponds to data type j. RSS 42 includes an address rule set (ARS) 44, a record rule set (RRS) 46 and a data reference (DR) (list 664 and data type reference DTA are optional and described below).

A. Address Rule Set (ARS)

ARS 44 includes a plurality of related data constructs which together define an address format for data type j, define rules for identifying information for forming an address having the address format and define rules for using the identified information to form an address. To this end, referring to FIG. 3, exemplary ARS 44 specifies an address format including six address fields 56, 58, 60, 62, 64 and 66.

For each field, ARS 44 specifies that the field is either "fixed" or "variable". Fixed means that the text (i.e. data object) used to instantiate a field is always the same. For example, for St. Mary's of Springfield, it will be assumed that all DBs are identified generally by a universal resource locator (URL) segment "http://hww.st_mary.springfield". In this case, all data types, including type j (see FIG. 2), include a first fixed field 56 wherein the text to instantiate the field comprises: http://hww.st_mary.springfield". As another example, each time a medication is given to a patient, an administration record is required. In this case, an exemplary fixed text field specifying the occurrence of medication administration is "medication/given".

Referring still to FIG. 2, variable means that text used to fill or instantiate a field may vary from record address to record address. For example, the character string used to fill a date field will vary daily, the character string used to fill a time field will vary as time lapses and the character string used to fill a patient field will vary depending on which patient a record is associated with. In FIG. 3, fields 56, 58 and 66 are fixed while fields 60, 62 and 64 are variable.

In addition to specifying fixed and variable characteristics, ARS 44 also specifies a field name for each field. For example, for fixed fields 56, 58 and 66 ARS 44 specifies "facility/server", "medication/given" and "report.html". For variable field 60, ARS 44 specifies name "patient ID", for field 62 ARS 44 specifies name "Date" and for field 64 ARS 44 specifies name "Time". These field names are not required by a DB, a system device or application but rather are provided to help a system user define data type definitions and to visualize address and record formats. To this end, the field names should generally describe the type of information corresponding to the field. Hence the name "Date" corresponds to the date field and so on.

For each field 56–66, ARS 44 also provides a field instantiation rule set (IRS). As the characteristics of each IRS are similar, only IRSs 45 and 47 corresponding to fields 62 and 58, respectively, are illustrated and described in detail. IRS 45 includes a field format 70, a variable search rule set (VSRS) 72 and a conversion rule set (CRS) 74. Similarly, IRS 47 includes a field format 76 and a variable search rule set (VSRS) 78.

For fixed field 58, field format 76 constitutes the specific fixed text to be placed in the field. For example, for field 58, the field format includes "medication/given". VSRS 78 includes a rule set which provides rules which indicate how, based on a set of information, to determine that medication has been given. For example, rules to determine if a medication has been given in the present example include a list of every possible medication bar code used at the St. Mary's facility. When one of the listed bar codes is identified in a set of information, medication administration is assumed. Although not illustrated, VSRS 78 may include other rules for determining if a medication has been administered. For example, where medication is delivered for administration in an electronically locked medication container which can signal when the container is opened (see U.S. patent application Ser. No. 08/955,475), a rule may assume administration when a container open signal is received as a portion of an information set. As another example, when a bar code is identified, the rule may also require reception of a patient ID # prior to assuming medication administration.

Although the rule sets described herein are relatively simple, other more complex rules are contemplated. For example, rules can be in the form of a sequence of program steps which are written in the JAVA program language, in Visual Basic programming code or in some other common programming language. In addition, rules may include Boolean operations, statistical computations or natural language processing to determine relationships among data items.

Referring still to FIG. 3, field format 70 constitutes a variable character string specifying an information format required to instantiate field 62 with a date. In the present example, the variable character string is "DD_MM_YYYY" where DD indicates the day of a month, MM indicates a number corresponding to the month of a year (i.e. "05" is May) and YYYY indicates a four digit year (e.g. 1996). Thus, independent of how a date appears in an information set, the date must be provided in the specified variable character string form "DD_MM_YYYY" according to format 70.

VSRS 72 includes a rule set which is used to search an information set for any date specifying information which can be used to instantiate variable field 62. To this end, VSRS 72 specifies a separate rule corresponding to each possible format in which a date might appear in an information set (see exemplary rules in VSRS 72). Exemplary rules include "##/##/####", "##_##_##" and "####_##_##" where each "#" corresponds to a number in the character string. Many other rules are contemplated including rules which account for spelled out months, other date patterns and so on.

Referring still to FIG. 3, with respect to variable field 62, while corresponding date specifying information may appear in a record or information set in any of several different formats, as indicated by format field 70, ARS 44 requires a specific format for instantiating variable field 62. Thus, conversion rules for converting date information to specific format 70 are required. To this end, CRS 74 includes conversion rules corresponding to field 62. In FIG. 3, an exemplary rule correlates "##/##/####" with "DD/MM/YYYY" meaning the first two "#'s" are assumed to correspond to "DD", the third and fourth "#'s" are assumed to correspond to "MM" and the last four "#'s" are assumed to correspond to "YYYY". Thus, if a string having the form "##/##/####" is located, format "DD/MM/YYYY" is assigned to corresponding numbers. Then, D's, M's and Y's in format "DD/MM/YYYY" can be mapped to D's, M's and Y's in field format 70 (i.e. into "DD_MM_YYYY") to make a data conversion and provide information to instantiate field 62 with a date having format 70. Similar IRSs (e.g. 80, 82, 84, 86) are provided for each of fields 56 through 66.

Although not illustrated here, in the case of some field types, IRS rules may be relatively simple. For example, with respect to date field 62 in FIG. 3, instead of searching an information set for date information, the corresponding IRS may simply cause a device or application to arrest a processor clock and identify a current date for instantiation purposes. Similarly, with respect to time field 64, the processor may simply access a clock and identify time for instantiation. Hereafter, the term "searching" will be used generically to mean actual examination to find information within an information set and also to mean accessing information in a known location.

B. Data Reference (DR)

Referring again to FIG. 2, DR 54 is a unique phrase or word which may be used in a document to refer to a record of data type j. In the present example, where data type j corresponds to a medication given to a patient, DR 54 may be as simple as "medication given". As another example, where a data type corresponds specifically to an ECG report, a corresponding DR may be "ECG report", the purpose of the DR is explained below.

C. Record Rule Set (RRS)

RRS 46 includes a plurality of related data constructs which together define a record format for data type j, define rules for identifying information for forming a record having the record format and define rules for using identified information to form a corresponding record. To this end, referring to FIG. 4, exemplary RRS 46 specifies a record format including six record fields 156, 158, 160, 162, 164 and 166. For each field, RRS 46 specifies that the field is either "fixed" or "variable". As in the case of ARS 44 above, fixed means that a text character string used to instantiate the field is always the same while variable means that a text character string or information to be provided within a field typically varies from record to record.

Field 156 is a fixed field while all other fields in RRS 46 are variable. In the present example it will be assumed that field 156 corresponds to a "medication/given" field indicating the general nature of the record, field 158 corresponds to a physician ID, field 160 corresponds to a patient ID, field 162 corresponds to date of medication administration, field 164 corresponds to a time of medication administration and field 166 corresponds to an administration record, including, among other things, the type of medication administered, the quantity of medication administered, the prescribing physician, the dispensing pharmacist, and so on. The type (i.e. physician ID, patient ID, etc.) of information or name for each field 156 through 166 is identified.

For each field 156 through 166, RRS 144 also provides a field instantiation rule set (IRS). As the characteristics of each IRS are similar, only IRSs 145 and 147 corresponding to fields 162 and 156, respectively, are illustrated and described in detail. IRS 147 includes a field format 176 and a variable search rule set 178. Similarly, IRS 145 includes a field format 170, a VSRS 172 and a converting rule set 174.

For fixed field 158, field format 176 constitutes the specific field text to be placed in the field. For example, for field 156, the field format includes "medication/given". VSRS 178 includes a rule set which provides rules which indicate how, based on a set of information, to determine that medication has been given. In the present example, the rules to determine if a medication has been given for the record rule set are identical to the "VSRS" corresponding to field 58 in FIG. 3.

Figure 3A:
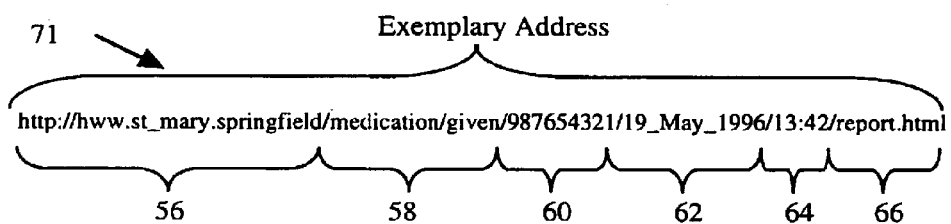
FIG. 3A is an exemplary address which is consistent with the address rule set of FIG. 3.
Figure 3:
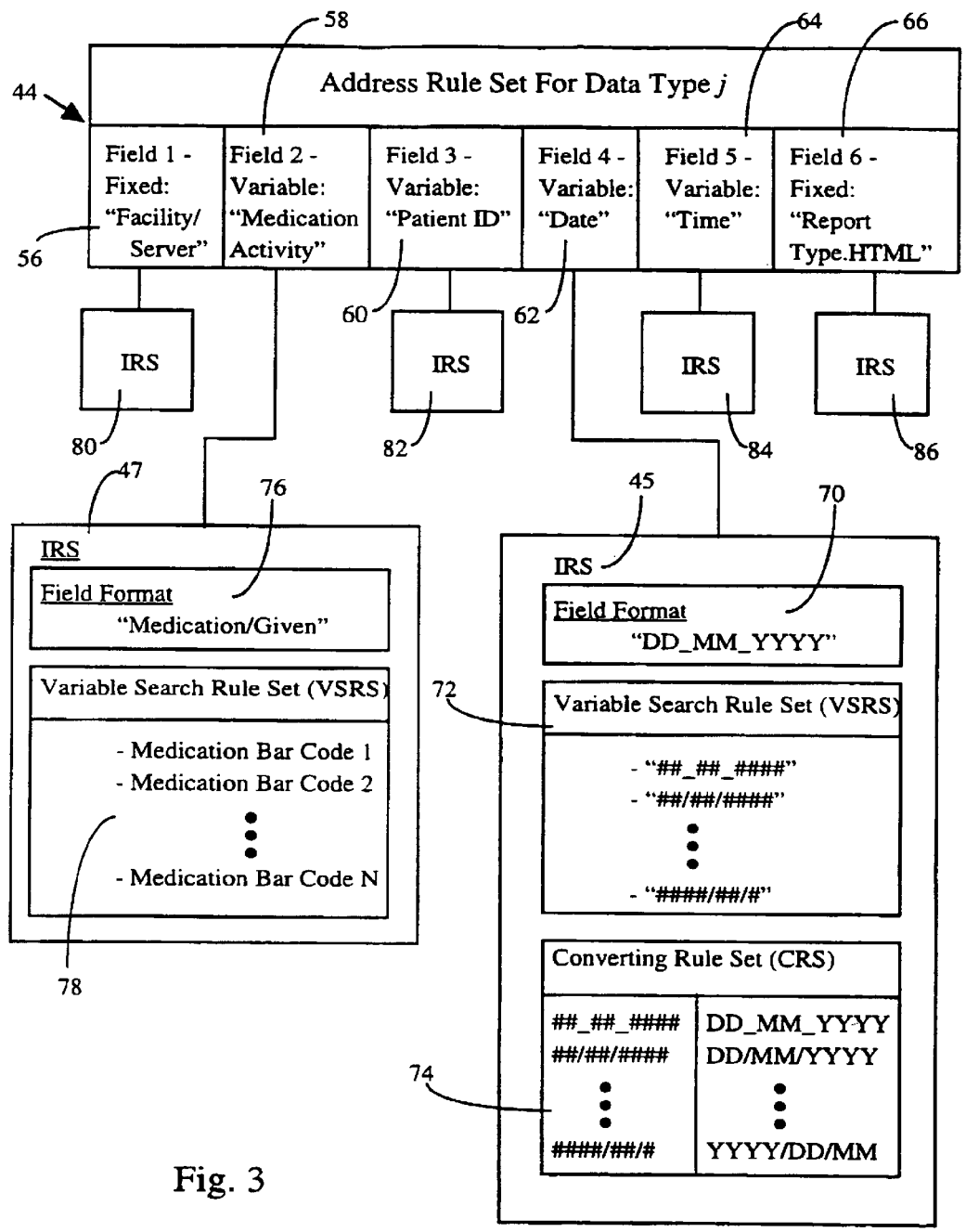
FIG. 3 is a schematic diagram illustrating details of the address rule set of FIG. 2.
Figure 4:
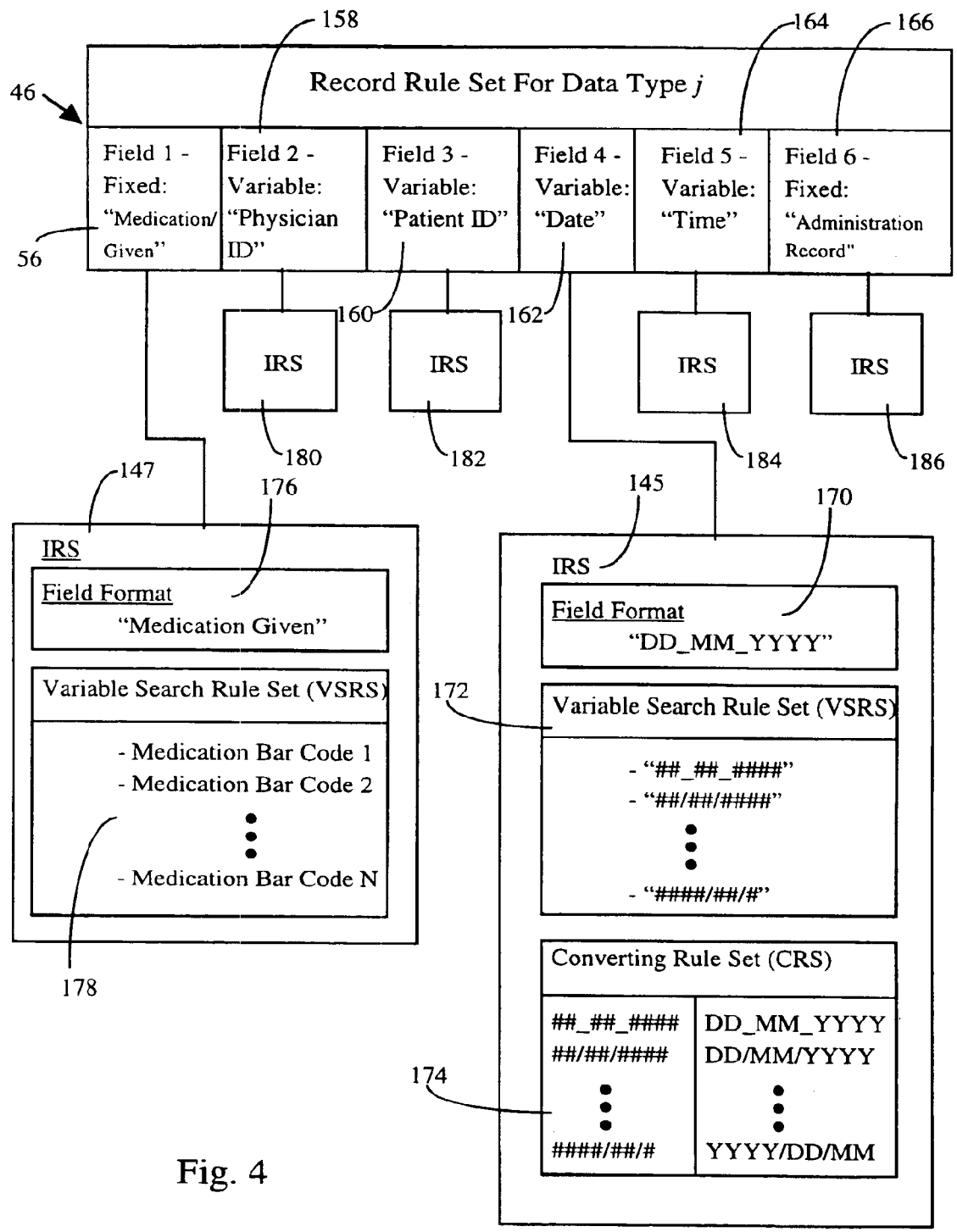
FIG. 4 is similar to FIG. 3, albeit illustrating details of the record rule set of FIG. 2.

Referring to FIGS. 3 and 4, the IRS 145 corresponding to variable date field 162 in RRS 46 is identical to the IRS 45 corresponding to ARS 44 and therefore is not explained here in detail.

Referring still to FIG. 4, IRSs 180, 182, 184 and 186 are provided for each of fields 158, 160, 164 and 166, respectively, each fixed field IRS including a field format and a VSRS and each variable field IRS including a field format, a VSRS and a CRS.

As indicated above, it should be appreciated that many of the fields in an ARS and a corresponding RRS and the instantiation rule sets associated therewith will be identical and therefore, in a preferred embodiment, where IRSs are identical among ARS and RRS fields, the rules are only defined once. In FIGS. 3 and 4, similar or identical rules are illustrated twice in the interest of facilitating clear explanation of the invention.

Referring again to FIG. 1, an exemplary DB literate processor 18 is described in the '349 application which is referenced above and which is incorporated herein by reference. The processor in the '349 application is capable of performing one or both of two separate database functions including a storing function and a linking function.

With respect to storing, the database literate processor can receive a record or information set, identify a specific data type corresponding to the record or information set, identify a RSS corresponding to the specific data type wherein the RSS includes an ARS, glean information from the information set to form an address corresponding to an address format for the information set and store the information set or record at the table address for subsequent retrieval or reference.

With respect to linking, the processor searches a record or information set for a DR (e.g. 54 in FIG. 2) and, when a DR is identified which references another record stored on a database, correlates the DR with an ARS (e.g. 44 in FIG. 2), identifies an address format corresponding to the ARS, gleans information from the record which is required to form an address according to the address format, forms an address from the gleaned information wherein the address corresponds to the record associated with the DR and thereafter forms a hyperlink to the referenced record which, when the DR is selected (e.g. via mouse controlled cursor, not illustrated), provides the referenced record to the system user that selected the DR.

The referenced record may be provided as a complete display screen or in a screen window when the DR is selected.

Moreover, it is contemplated that when the DR is selected the referenced record may simply be expanded in the referring record or information set. For example, assume a "heart image" DR corresponds to an image of a heart which is stored on a system database and that a physician types the phrase "heart image" while entering a report about a patient visit, it is contemplated that in one embodiment of the invention, when the phrase "heart image" is entered, the database literate processor forms the address corresponding to the image and, instead of creating a hyperlink thereto, retrieves the image and "blends" (i.e. reformats the text to accommodate the image) the image into the text facilitating easy reference.

In the present example, it is assumed that processor 18 in FIG. 1 is only capable of the linking function. It is also assumed that PC-1 is only capable of the storing function while PC-2 is capable of both the linking and storing functions.

The '169 application referenced above is incorporated here in by reference and describes an exemplary remote ICD which can be provided with an address format for a specific record to be received and can then receive information which constitutes a record, use some of the received information to provide an address having the address format for the received record and then store the record and address for subsequent downloading to a DB. It is contemplated that ICD's used with the present invention, like the ICDs described in the '169 application, could have the same storing and linking capabilities of the DB literate processors described in the '349 application. To this end, it is assumed hereinafter that ICD-1 and ICD-2 are each capable of the storing database function described above while ICD-3 is capable of both the storing and linking database functions described above.

Thus, each of processor 18, PC-1, PC-2, ICD-1, ICD-2 and ICD-3 require some subset of RSS information to perform their intended functions (i.e. linking and storing). ICD's 1 and 2 and PC-1 each require an ARS and corresponding RRS, each of ICD-3 and PC-2 require an ARS, a DR and a corresponding RRS and processor 18 requires an ARS and a corresponding DR.

D. Relevant Devices and Applications (D/A) List

Referring again to FIG. 2, in addition to the ARS 44, RRS 46 and DR 54, RSS 42 may also, optionally, include a relevant devices and applications list 69 (D/A list) which indicates the RSS information sub-sets to be provided to each system device and application. Referring also to FIGS. 1 and 5, an exemplary D/A list 69 corresponding to information system 10 includes a table having a device/application column 81 and an "IRS information provided" column 83. Column 81 lists every device and application in system 10 which may receive any of the RSS information for the specific data type j. In the present example, list 81 includes ICD-1, ICD-2, ICD-3, PC-1, PC-2 and DB literate processor 18.

Column 83 lists each type of RSS information which is provided to each specific device or application in column 81. Thus, with respect to data type j, column 83 specifies that the ARS and RRS corresponding to data type j are provided to ICD-1. Similar information is provided to ICD-2. With respect to ICD-3, information provided includes the DR, in addition to the ARS and RRS corresponding to data type j. Column 83 also specifies that each of the ARS and RRS are provided to PC-1 and that, in addition to the ARS and RRS, the DR is provided to PC-2. With respect to DB literate processor 18, column 83 specifies that the ARS and DR corresponding to data type j are provided to processor 18.

In the alternative, instead of specifying specific RSS information to be provided to each information system device and application, all of the RSS information may be provided to every system device and application. While providing all of the RSS information to every device and application results in a simpler system, such a system would waste device and application memory and therefore, at least in cases where memory is limited, might be prohibitive.

E. Data Type Reference (DTR)

Referring yet again to FIG. 2, RSS 42 may further, optionally, include a data type reference (DTR) 13. DTR 13 serves a similar function as DR 54 but, instead of being used for the DB linking function, is used during the DB storing function. To this end, DTR is a reference which will always be included in an information set when a corresponding data type should be employed for storing. For example, each time a specific imaging system is used, the imaging system may provide its identification number to the ICD which is then required to log imaging system use. In this case, the imaging system ID # may be provided as a DTR corresponding to a suitably formatted RSS. Then, when an ICD identifies the imaging system ID # within an information set, the ICD can automatically identify the RSS corresponding to the DTR and generate an address and record to memorialize the imaging system use.

In the absence of the DTR, the ICD would have to search the information set for information required in each field within an ARS and each field within a corresponding RRS to determine if a record should be generated and stored. The DTR simply short circuits then process of identifying suitable data types for storing.

Instead of being a single fixed string, the DTR may be a variable character, text or other data type string. For example, if an ICD is required to memorialize each patient encounter, the DTR may include a variable character string such as "##########" which, when located, indicates a patient encounter. When the patient ID string is encountered, the ICD simply employs the corresponding RSS components to memorialize the encounter.

With respect to the medication given data type, referring to FIGS. 2 and 3, the DTR 13 may include a variable rule set which mirrors VSRS 78 so that any time a medication bar code is identified, the ICD can quickly identify the correct data type for memorializing administration.

Referring again to FIGS. 1 and 2, with database specifications 34, 36 and 38 having all of the features described above, RSS information (e.g. 42) can be provided to system 10 devices and applications to facilitate complete information compatibility.

2. Enterprise Wide IRSs and ARS Specification

Referring again to FIG. 1, as virtually all system devices and applications require some sub-set of RSS information, it has been recognized that, instead of specifying RSS information separately for each DB, device and application in system 10, the RSS information can be specified a single time so that the RSS has a unique format and characteristics and thereafter can be used with all DBs, devices and applications which constitute the system 10. In addition, it has been recognized that, as many address and record fields require similar information types, a pre-defining set of unique field IRSs can be developed which can be used to streamline the process of defining data type definitions.

For instance, in the present example which corresponds to a medical facility, a large percentage of total facility records will require a date corresponding to each specific field. Referring also to FIG. 3, and specifically to variable date field 62, each time a date field is required in an ARS (or an RRS), a user is required to specify a field format 70, a VSRS 72 and a CRS 74. According to the present invention, a pre-defining field IRS corresponding to a variable date field includes a pre-defining field format and corresponding VSRS and CRS like format 70, VSRS 72 and CRS 74, respectively, which are used every time a variable date field is required in an ARS.

Similarly, IRSs are provided for all other variable and fixed fields routinely used in system 10 data type definitions. Thus, for example, referring to FIGS. 3 and 4, IRS 47 is identical to IRS 147. In this case, the pre-defining field rule set only includes a single instance of an IRS which, when selected and linked to a specific field, provides all of the rules required to instantiate the specific field.

Referring again to FIG. 1, exemplary pre-defining field IRSs are illustrated as being stored in DB 26 which is linked to databases DB-1, DB-2 and DB-3 for use in defining DB specifications 34, 36 and 38.

To facilitate use of pre-defining field IRS capabilities an inventive editor having two related editing functions is required. A first or pre-defining field editor (hereinafter "field editor") function is required to define IRSs for each field potentially useable by system DBs for addressing and record format purposes. Second, a data type editor (hereinafter "data type editor") function is required to define data type information including ARSs, RRSs, DRs and D/A lists.

Prior to describing the data type editor and field editor functions, a general understanding of system 10 architecture is helpful. To this end, referring now to FIG. 6, system 10 generally includes a communication network 84 which links together system databases DB-1, DB-2 and DB-M, DB literate processor 18, DB 26 and a database administration work station 86. Work station 86 includes a screen 88, a work station processor 90 and one or more interface devices 92. As illustrated, exemplary interface devices include a keyboard 92 and a mouse 93 which controls a cursor (not illustrated) on screen 88. In addition, processor 90 is linked to a transceiver 94 which can receive information from, and transmit information to, remote ICD-1, ICD-2 and ICD-3 via RF or some other suitable means.

Figure 6:
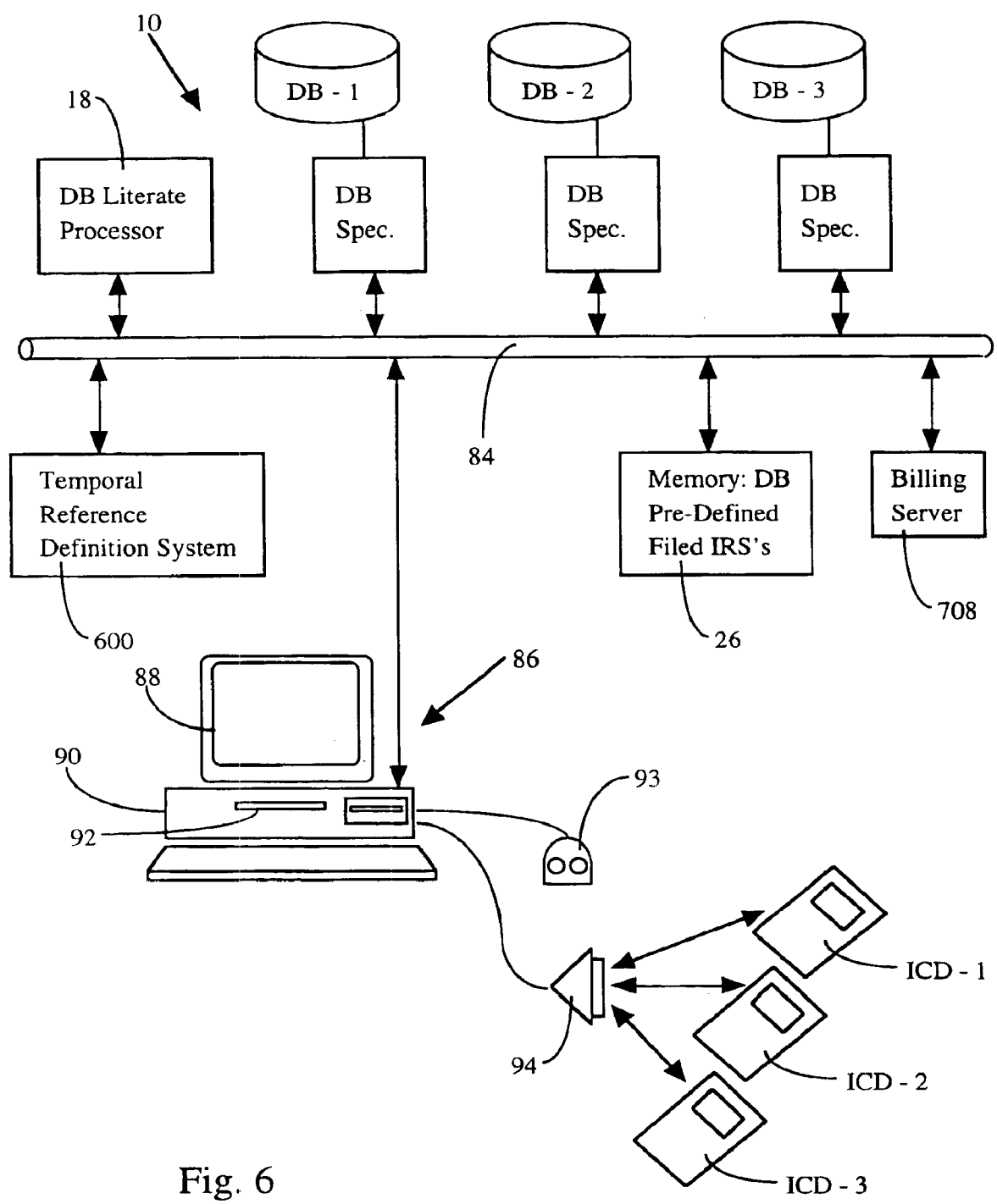
FIG. 6 is an illustration of an exemplary system according to the present invention and consistent with FIG. 1.

Referring still to FIG. 6, each of the field editor and data type editor comprise software programs which are loaded on to work station 86. Preferably, each of the field and format editors include similar types of tools, and, specifically, exemplary tools include instructions, selection icons and information boxes which are presented on display 88 screens. A work station user uses mouse 93 to control a cursor to select and deselect screen icons and to place the cursor within information boxes to provide information in the boxes via keyboard 92. Also, preferably, both the field and data type editors have similar appearances so that changing from one editor to the other is essentially seamless from the perspective of a system user.

Figure 7:
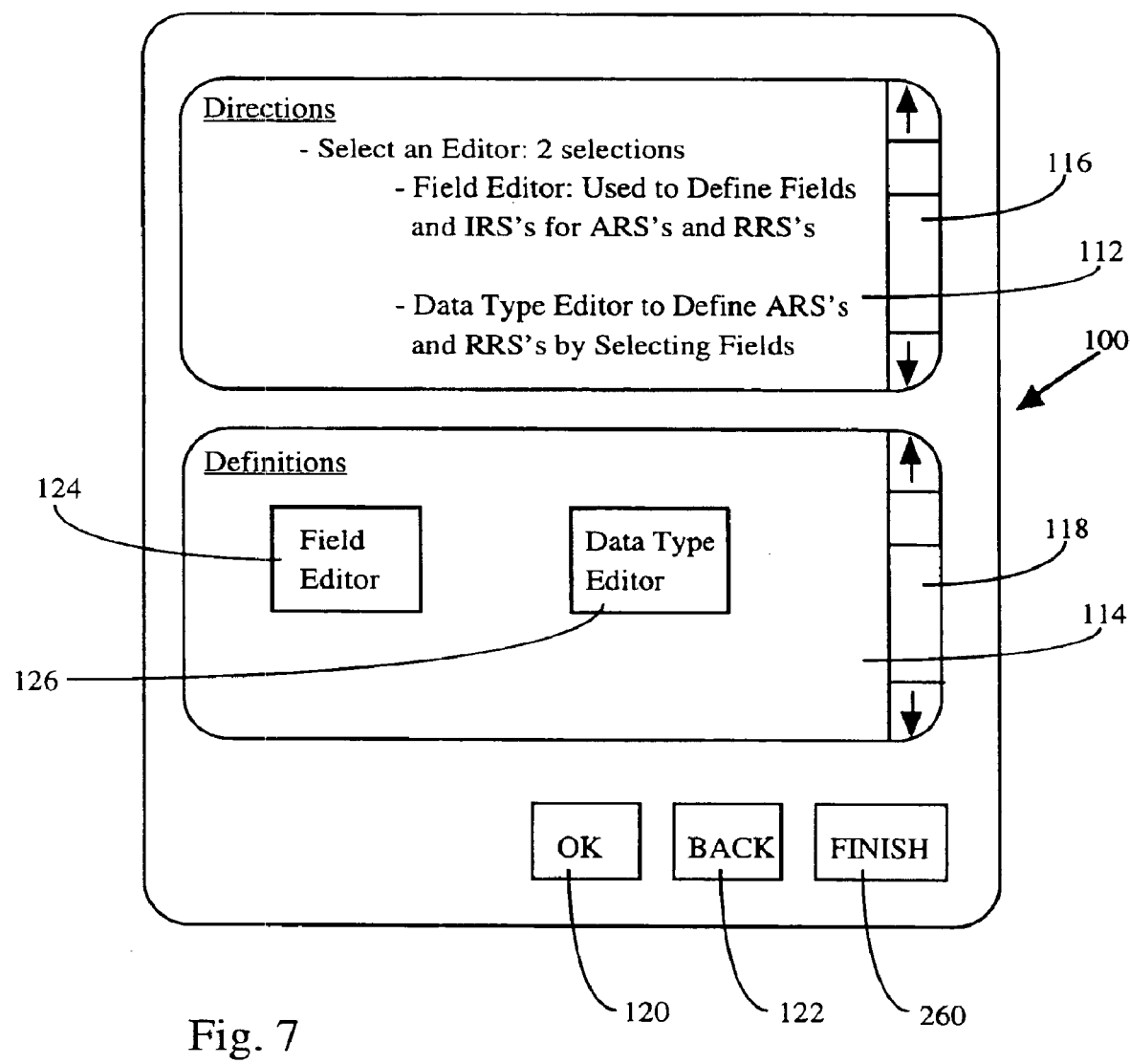
FIG. 7 is a schematic diagram illustrating an exemplary editor screen according to the present invention.

Referring now to FIG. 7, an exemplary display screen 100 according to the present invention is illustrated. Generally, each of the screens provided on display 88 includes two separate sections identified as a directions section 112 and a definitions section 114. Directions corresponding to a displayed screen and for guiding a user through the process of using the field and data type editors are provided in section 112. Interactive tools such as information boxes and selection icons for specifying field and format information are provided in section 114. Each of sections 112 and 114 includes a conventional scrolling bar along the right edge thereof for scrolling within the separate section. For example, the bar corresponding to section 112 is identified by numeral 116 while the bar corresponding to section 114 is identified by numeral 118. When instructions or defining tools which are required exceed the spaces within sections 112 or 114, associated scrolling bars 116, 118, respectively, can be used to scroll within each one of the separate sections 112, 114 to view portions of the directions and tools, respectively.

In addition to sections 112 and 114, each screen according to the preferred embodiment of the invention includes an "OK" icon 120 and a "BACK" 122. By selecting the OK icon 120, a work station user indicates to the editor that the information specified within definitions section 114 is complete. By selecting the BACK icon 122, the work station user is indicating that the user would like to step back to the previously displayed editor screen to either check a selection or modify a selection. Moreover, certain screens also include other useful icons. For example, screen 100 includes a "FINISH" icon which can be selected when a user is done using the editors and to exit the program.

Referring still to FIG. 7, the first screen 100 which is provided to a work station user when a user wishes to use the inventive editors is illustrated. In section 112, screen 100 directs the user to select one of the field or data type editors and provides basic instructions which indicate the differences between each of the field and data type editors. To this end, the exemplary instructions indicate that the field editor is used to define fields and instantiation rule sets (IRSs) for fields and the data type editor is used to define address rule sets and record rule sets by selecting already defined and pre-defining field IRSs.

In section 114, screen 100 provides a "FIELD EDITOR" icon 124 and a "DATA TYPE EDITOR" icon 126. When one of icons 124 or 126 is selected, the appearance of the selected icon changes. In this explanation, it will be assumed that when an icon is selected the icon appearance changes color to indicate selection. After one of icons 124 or 126 is selected, OK icon 120 is selected to proceed to the next editor screen.

Although each of the field and data type editors are accessible via screen 100 and the editors are meant to be used together, each of the field and format editors will be described in detail below separately. Most of the screen images which follow reflect some level of user selection or data entry corresponding to one or another specific field or format which is being defined in the example. Nevertheless, it should be understood that some of the images are subsequently used to explain additional field and format defining steps and that, during subsequent defining, while image features would be similar to the features illustrated, some of the displayed information would change to accommodate the specific defining steps. For example, in the process of defining a pre-defining field IRS, a user specifies a field name such as "facility/server" which thereafter is used in subsequent images to orient the system user. To this end, some of the images include the phrase "facility/server". However, subsequently, when defining another field IRS corresponding to, for instance, a field named "medication given", the phrase "medication given" would replace the phrase "facility/server" on the illustrated screens. In most cases, screen features which change during system operation to reflect current instantiation are provided in quotation marks.

B. Field Editor

Referring again to FIG. 3, ARS 44 includes six fields 56, 58, 60, 62, 64 and 66. Prior to defining ARS 44, according to the present invention, each field 56–66 and a corresponding IRS must be defined using the field editor. Generally the processes of defining each field 56–66 and corresponding IRSs are similar and therefore the field defining process is only described below in the context of a sub-set of fields 56–66. However, there are some differences in the field defining process which are made clear by the following examples. Below, the field defining or editing process is described in the context of fields 56, 58 and 62.

Referring to FIGS. 3 and 3A, an exemplary address 71 corresponding to ARS 44 in FIG. 3 is illustrated. Similarly numbered fields in FIGS. 3 and 3A correspond to each other. As indicated in FIG. 3, fields 56, 58 and 66 are fixed while fields 60, 62 and 64 are variable. Field 56 corresponds to a facility/server and includes a character string which specifies a specific facility/server. To this end standard URL addressing protocol is used to form the string "http://hww.st_mary.springfield". Every record stored on system 10 will include this first fixed field character string.

Second field 58 corresponds to administration of a medication and must include fixed character string "medication/given". Similarly, field 66 corresponds to a report type and includes fixed string "report.html" indicating that the corresponding report or record is in html format. Variable fields 60, 62 and 64 are described in more detail below.

Figure 8:
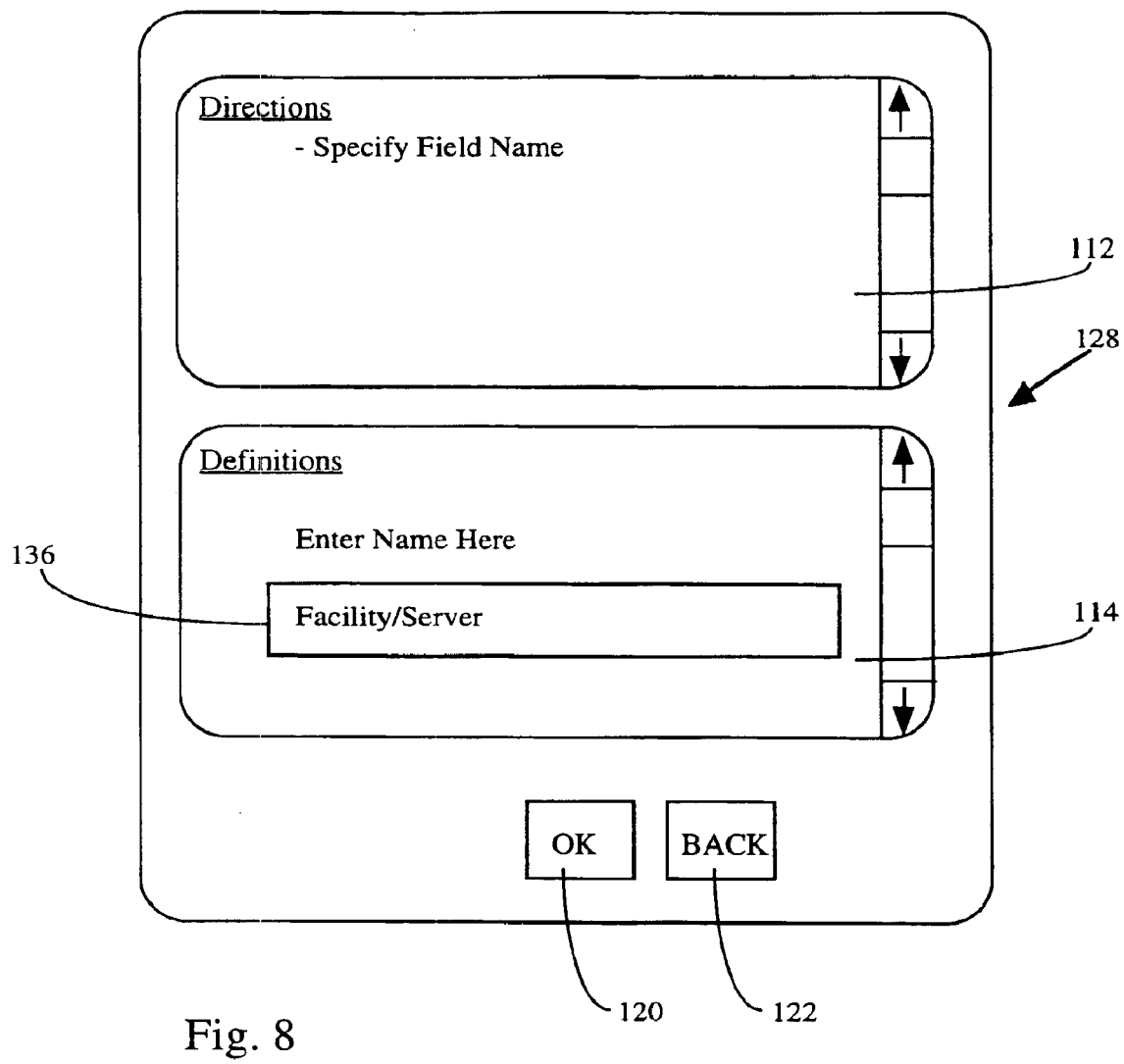
FIG. 8 is similarly to FIG. 7, albeit illustrating another screen.

Referring now to FIGS. 6, 7 and 8, after FIELD EDITOR icon 124 and OK icon 120 have been selected, work station 86 provides screen 128 on display 88. In section 112, screen 128 instructs the user to specify a name for the field which is currently being defined. In section 114, screen 128 provides an information box 136 for entering the name of the field being defined. Name choice is left to the system user but should typically be a name which reflects the type of field corresponding thereto so that subsequently the user and other system users will easily be able to recognize the nature of the field. For example, a field which will include a date may be name "Date", a field which will include a patent I.D. may be named "Patent ID", a field which will include a text report may be named "text report" and so on. Referring also to FIG. 3 and specifically to field 56, the name provided for field 56 is "facility/server".

In addition, name choice is unique in that the system will not allow a field name to be used more than once to allow more than one field to be referenced by the same name. Thus, where the name "Date" is provided for a field, the field editor will not allow subsequent use of that name. If a duplicative name is provided the editor will request entry of a new name.

Figure 9:
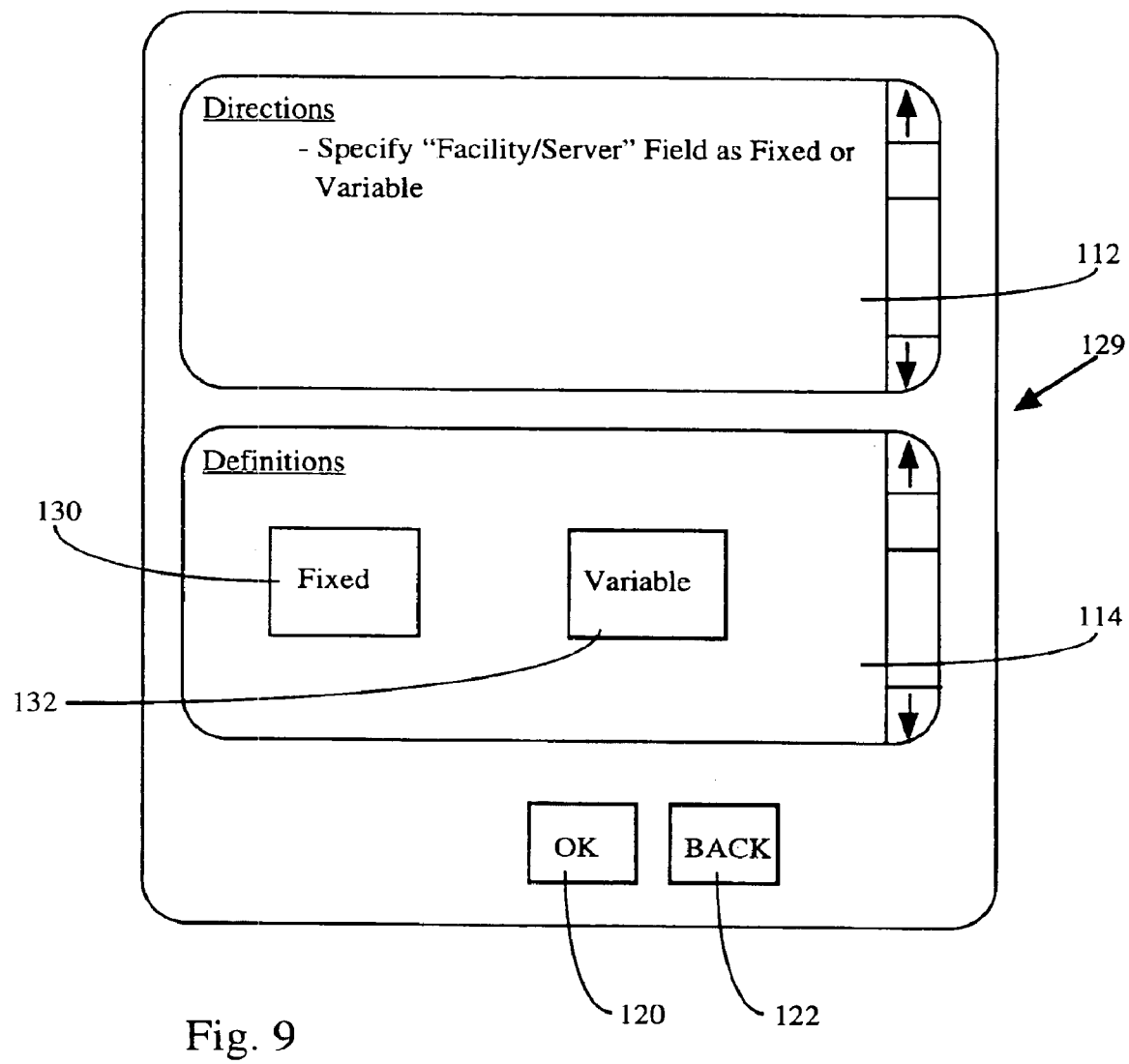
FIG. 9 is similar to FIG. 7, albeit illustrating yet another screen.

Referring to FIGS. 6, 8 and 9, after a user provides a name in box 136 and selects OK icon 120, work station 86 provides screen 129 on display 88. In section 112, screen 129 instructs a user to specify if the facility/server field is fixed or variable. As described above, fixed means that the character string which will be used to instantiate the field being defined will constitute a fixed character string while variable means that the character string which will be used to instantiate the field being defined may vary from address to address or record to record.

Figure 10:
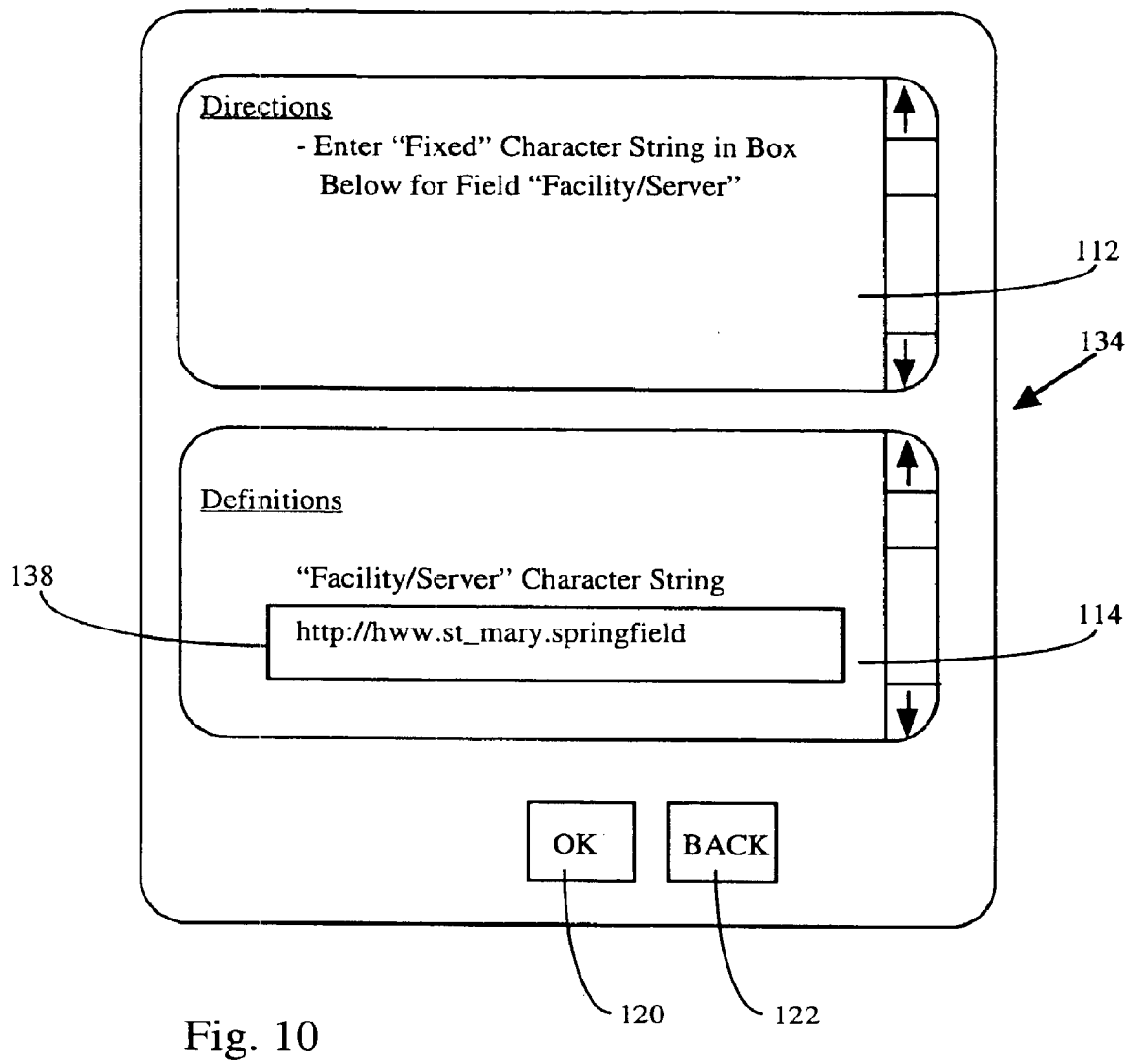
FIG. 10 is similar to FIG. 7, albeit illustrating yet another exemplary screen.

In section 114, screen 129 provides a "FIXED" icon 130 and a "VARIABLE" icon 132. To indicate that the facility/server field is fixed, the user selects icon 130 and to indicate that the field is variable, the user selects icon 132. Referring to FIGS. 6, 9 and 10, in the present example user selects FIXED icon 130 and OK icon 120 and work station 86 provides screen 134 on display 88. In section 112, screen 134 instructs the user to enter a fixed character string in the information box below for the facility/server field. In section 114, screen 134 provides an information box 138. The user may place a cursor within box 138 and type in the fixed character string for the facility/server field. In the present example, the fixed field string "http://hww.st_mary.springfield" is provided and corresponds to a field format (e.g. 76 in FIG. 3) for first field 56.

At this point it should be noted that, while the present invention minimizes the amount of programming training required, some minimal amount of DB addressing training and knowledge about specific facility servers is still necessary. For example, during field definition using the field editor, a user must know how to address a facility server using a DB supported URL segment like character string "http://hww.st_mary.springfield". In the alternative, where the DBs can only be accessed via specific supported designated character strings, the field editor may be programmed to automatically provide supported DB designating character strings from the systems DBs and provide DB designating IRSs based thereon. In the present example, as it is assumed system 10 DBs are all referenced by the same designating string (i.e. http://hww.st_mary.springfield), the field editor would automatically provide the designating string as a field format for the first field in each ARS. While this automating feature is contemplated, it will be assumed in the present example that such a feature is not provided.

Figure 11:
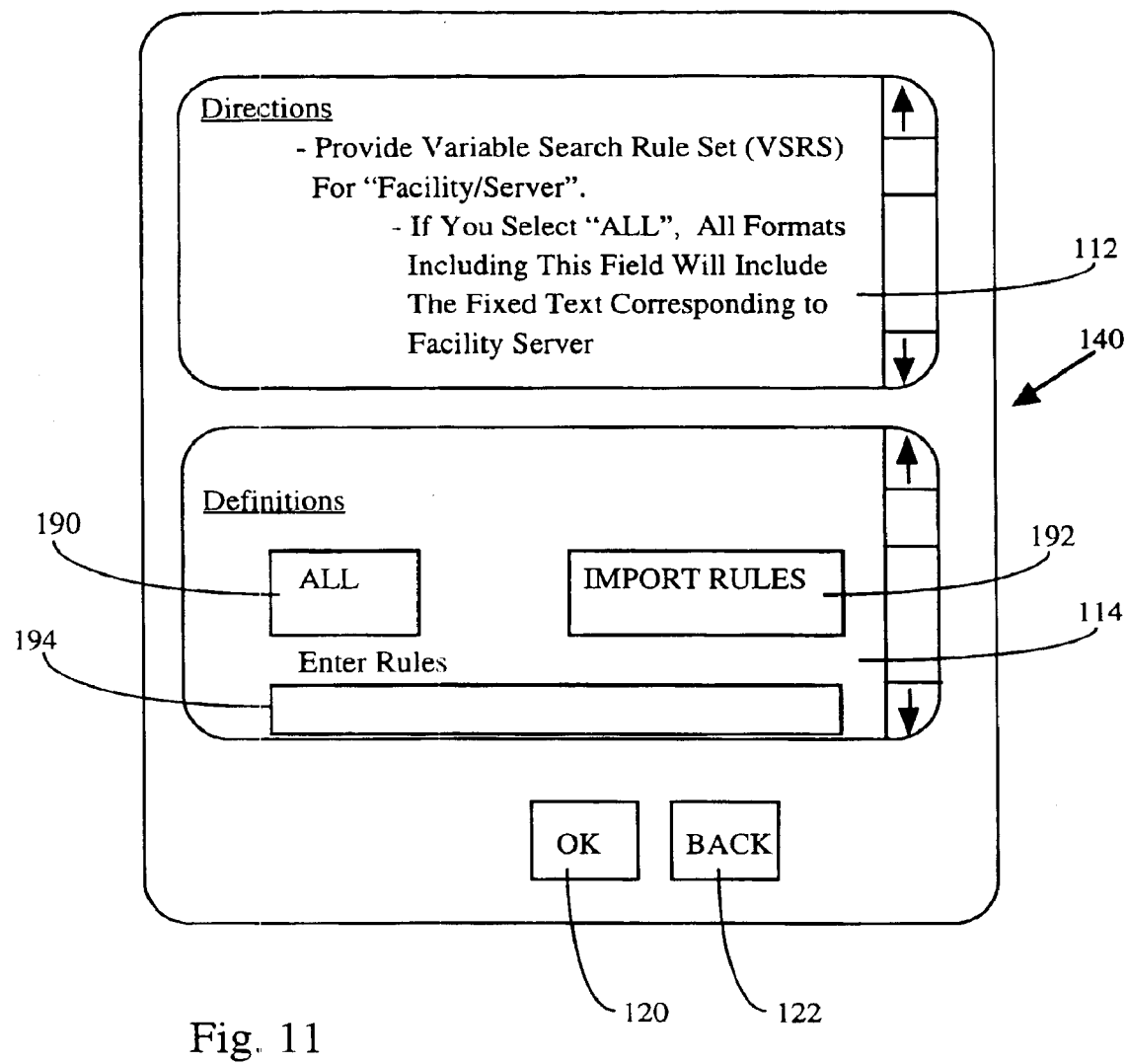
FIG. 11 is similar to FIG. 7, albeit illustrating yet another exemplary screen.

Referring to FIGS. 7, 10 and 11, after the fixed character string has been provided in box 138 and icon 120 has been selected, work station 86 provides screen 140 on display 88. In section 112, screen 140 instructs the user to provide a variable search rule set for the facility/server field. In addition, the directions indicate to the user that if an "ALL" icon is selected, all formats which include the facility/server field will include the fixed character string corresponding to the facility server. In other words, when an ALL icon is selected, the VSRS (e.g. 78 in FIG. 3) corresponding to first field 56 specifies that all formats including the corresponding field, independent of record information, meet the VSRS criteria. Thus, if the ALL icon is selected, all formats which include the facility/server field will include the character string "http://hww.st_mary.springfield".

In section 114, screen 140 provides an "ALL" icon 190, an "IMPORT RULES" icon 192 and an information box 194. If icon 190 is selected, all of the information corresponding to the facility/server field has been defined. In the present example, all records stored on system databases are presumed to be related to the system facility and server and therefore, with respect to the facility/server field, a user selects ALL icon 190 and then icon 120. Icon 192 is explained in more detail below.

Referring to FIGS. 6, 7 and 11, after icons 190 and 120 have been selected on screen 140, work station 86 again provides screen 100 on display 88. Again, the user has the option to select FIELD EDITOR icon 124 or DATA TYPE editor icon 126.

At this point it is assumed that the user wishes to define additional fields and therefore selects icon 124 and OK icon 120. Referring to FIG. 8, when icon 120 is selected, control passes to screen 128 where the user provides another unique field name in information box 136. Referring also to FIGS. 3 and 3A, the next field and associated IRS to be defined are field 58 where, when medication has been administered, field 58 must include fixed character string "medication/given". An exemplary name which is selected by the user for the new field will be "medication given" (not illustrated) which is provided in box 136. When icon 120 is selected, referring to FIG. 9, control again passes to screen 129 where, in section 112, screen 129 instructs the user to specify whether or not the medication given field is fixed or variable. Once again, because this field is fixed, the user selects icons 130 and 120 and control passes to screen 134 as illustrated in FIG. 10. In section 112, screen 134 instructs the user to enter a fixed character string in the box below for the medication given field. To this end, the user places a mouse controlled cursor within box 138 and types in the desired fixed character string "medication/given" (not illustrated). Referring again to FIG. 3, the text provided in box 138 is the field format 76 for the medication given field.

Referring to FIGS. 10 and 11, after OK icon 120 is selected on screen 134, control passes to screen 140 where, in section 112, the user is instructed to provide a variable search rule set for the medication given field. In this case, the user may do one of three things. First, the user may again select ALL icon 190 indicating that all records including the field being defined will include the fixed character string medication/given.

Second, the user may place a mouse controlled cursor within information box 134 and, using some special type of syntax, specify rules for determining whether or not a medication has been given to a patient. In this regard, although not illustrated, the special syntax would be relatively simple to learn and would be universal with respect to system 10. Preferably syntax rules could be specified in section 112.

Third, the user may select IMPORT RULES icon 192. When icon 192 is selected, it is contemplated that the user could use work station 86 to access already specified information or rules stored on one or more system databases for determining whether or not a medication has been given. For example, although not illustrated, a pharmacy database may be linked to system 10 which includes a list of medication bar codes corresponding to every type of medication which may be given within a medical facility. In this case, by accessing the pharmacy's database, all of the medication bar codes or indicators corresponding to each bar code may be imported into the variable search rule set which is currently being defined. Then, if any of the bar codes or indicators associated therewith are identified within a searched information set, it would be assumed that the medication indicated thereby has been administered.

In the present example, it is assumed that such a pharmacy database exists and that the user selects the import rules icon 192. Thereafter, although not illustrated, the user selects the medication bar codes from the pharmacy database as the VSRS corresponding to the "medication/given" field format 76 (see FIG. 3).

It should be noted that the tools and methods for specifying rule sets, although important, are not at the heart of the present invention. Instead the invention is meant to cover the general concept of specifying DB structures, address and record formats and corresponding IRSs once for use by an entire information system and reusing the specified information time and again in a repetitive fashion to streamline DB definition and maintenance.

Referring to FIGS. 3 and 11, after the variable search rule set has been provided for field 58, icon 120 is again selected and control passes again to screen 100. It is assumed that the system user next wishes to define variable date field 62 and corresponding IRS 45. To this end, in FIG. 7, the user selects FORMAT EDITOR icon 126 and OK icon 120 and control again passes to screen 128 as illustrated in FIG. 8. The user provides a field name "date" in box 136 and again selects icon 120 so that control passes to screen 129 in FIG. 9.

Using screen 129, the user indicates that the date field is variable. Referring also to FIG. 10, in section 112 the user is instructed to enter a variable field character string for the date field. The instruction is essentially as it appears in section 112 except that the word "variable" is substituted for "fixed" and the name "date" is substituted for "facility/server". In addition, although not illustrated, the directions may also indicate a system syntax for specifying a variable character string. In box 138, the user provides a variable character string field format corresponding to the date. In this case, referring again to FIG. 3, it is assumed the user provides the string "DD_MM_YYYY".

Figure 12:
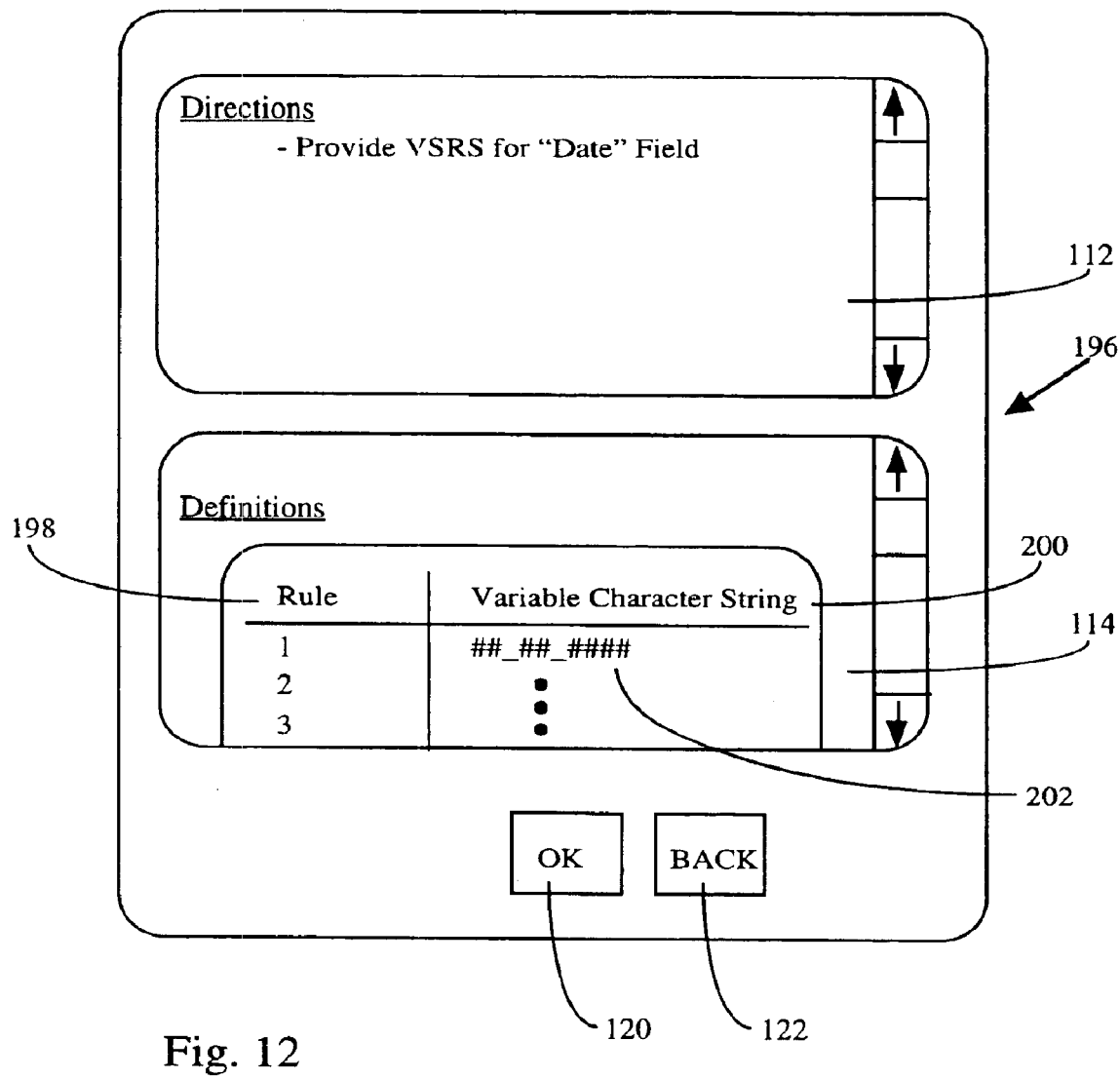
FIG. 12 is similar to FIG. 7, albeit illustrating yet another exemplary screen.

After OK icon 120 is selected on screen 134, referring also to FIG. 12, control passes to screen 196. In section 112, screen 196 instructs the user to provide a VSRS for the date field. Typically, information corresponding to a variable field may take any of several different character string forms and therefore, in section 114, screen 196 provides a rule list to be defined by the system user. The rule list includes a rule number column 198 and a variable character string column 200. Initially, column 200 is completely blank. The user places a mouse controlled cursor within column 200 and begins specifying variable character strings for each of the rule numbers in column 198.

It is contemplated that variable numbers would be represented by a "#" (i.e. # may be any of 0–9), specific numbers would be identified by the specific numbers (e.g. 9 is 9), variable letters would be defined by "★" (i.e., ★ may be any of a–z) and specific letters would be defined by the specific letters (e.g. x is x). Directions to this effect may be provided in Section 112. FIG. 12 reflects specification of a single variable character string 202. However, a large number of variable character strings are contemplated.

After all of the variable character strings have been specified in column 200, the user selects OK icon 120 indicating that the VSRS has been completely defined. Referring to FIG. 3, at this point, each of the field format 70 and VSRS 72 corresponding to variable date field 62 have been specified.

Figure 13:
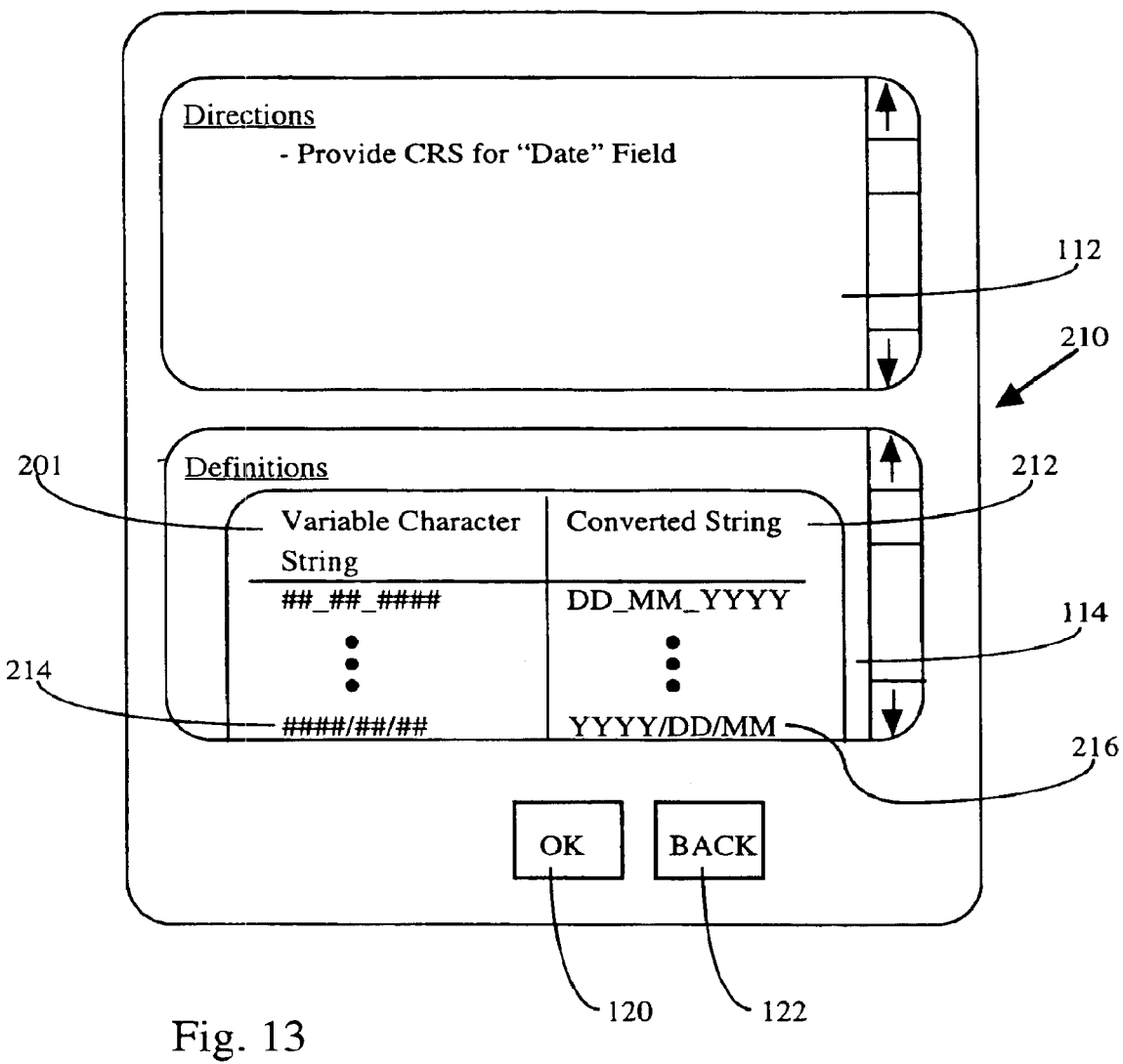
FIG. 13 is similar to FIG. 7, albeit illustrating yet another exemplary screen.

Next, the CRS 74 corresponding to date field 62 has to be specified. To this end, when icon 120 is selected in FIG. 12, control passes to screen 210 in FIG. 13. In section 112, screen 210 instructs the user to provide a CRS for the date field. In section 114, screen 210 provides a CRS table list to be defined by the system user. The table includes a variable character string column 200 and a converted string column 212. Referring also FIG. 12, column 200 in FIG. 12 is identical to column 201 in FIG. 13 and includes the variable character string list specified by the system user. Column 212 is initially completely blank. The user may place a mouse controlled cursor within column 212 and begin specifying converted strings for each of the variable character strings in column 201. To this end, referring also to FIG. 3, in this example, each converted string in column 212 must include characters which correspond to field format 70, although the characters in each converted string may be in a different order than the characters in field format 70. For example, an exemplary variable character string 214 is "####/##/##". As field format 70 is "DD_MM_YYYY", each of the Ds, Ms and Ys must be associated with one of the #s in variable character string 214. The corresponded converted string 216 has the form "YYYY/DD/MM". Thus, information in the variable character string 214 is linked to specific information in field format 70 via converted string 216. Obviously additional rules would be specified in the case of a date field, the illustrated rules being minimal in an effort to simplify the present explanation.

In operation, referring to FIG. 3, and specifically to IRS 45, if any one of the character strings in VSRS 72 is identified, a two step conversion process occurs. First, the string is converted via a corresponding CRS 74 to a D, M and Y format. Second, the D, M and Y information in the CRS is converted to the D, M and Y information in the field format.

After all of the CRS rules have been defined, the user selects OK icon 120 on screen 210 and control again passes to screen 100 in FIG. 7. This process of stepping through field editor screens is repeated for every field in ARS 44. Similarly, referring also to FIG. 4, this process is repeated for every field in RRS 46. Where fields in RRS 46 are identical to fields in ARS 44, the fields and corresponding IRSs are only defined a single time. Furthermore, many other fields and corresponding IRSs are defined using the field editor screens as described above.

Referring again to FIG. 6, all of the defined fields and corresponding IRSs are stored in DB 26 for access by work station 86 to define ARSs and RRSs for use by system 10 using the data type editor described next.

Once again, it should be recognized that, while the rules sets described herein are relatively simple, other more complex rules are contemplated. To this end, the rules can be in the form of a sequence of program sets which are written in the JAVA program language, in Visual Basic programming code or in some other common programming language. In addition, the rules may include Boolean operations, statistical computations or natural language processing to determine relationships among data items.

C. Data Type Editor

Referring to FIGS. 2, 3, 4 and 5, the data type editor will be described in the context of a process for defining ARS 44, RRS 46, DR 54, a D/A list 69 for data type j and a DTR 13 for data type j.

Referring also to FIGS. 1 and 7, after all of the fields which will be required to construct ARSs and RRSs have been defined and stored in DB 26, the user selects DATA TYPE editor icon 126 and OK icon 120 to access the data type editor function. To this end, when icon 120 is selected, referring also to FIG. 14, control passes to screen 218.

In section 112, screen 218 instructs the user that address formats, record formats, data references, applicable devices/applications and DTRs should be specified together for a specific data type. In addition, the directions request that, initially, the user provide a unique data reference (DR) for the data typed to be defined. In section 114, screen 218 provides an information box 220 in which the user specifies a DR. In the present example, the provided DR is "medication given." As indicated above, the DR is user-chosen and should be selected such that the DR is a phrase or a word which the user or some other system user would likely use when referring to a specific data type.

Figure 14:
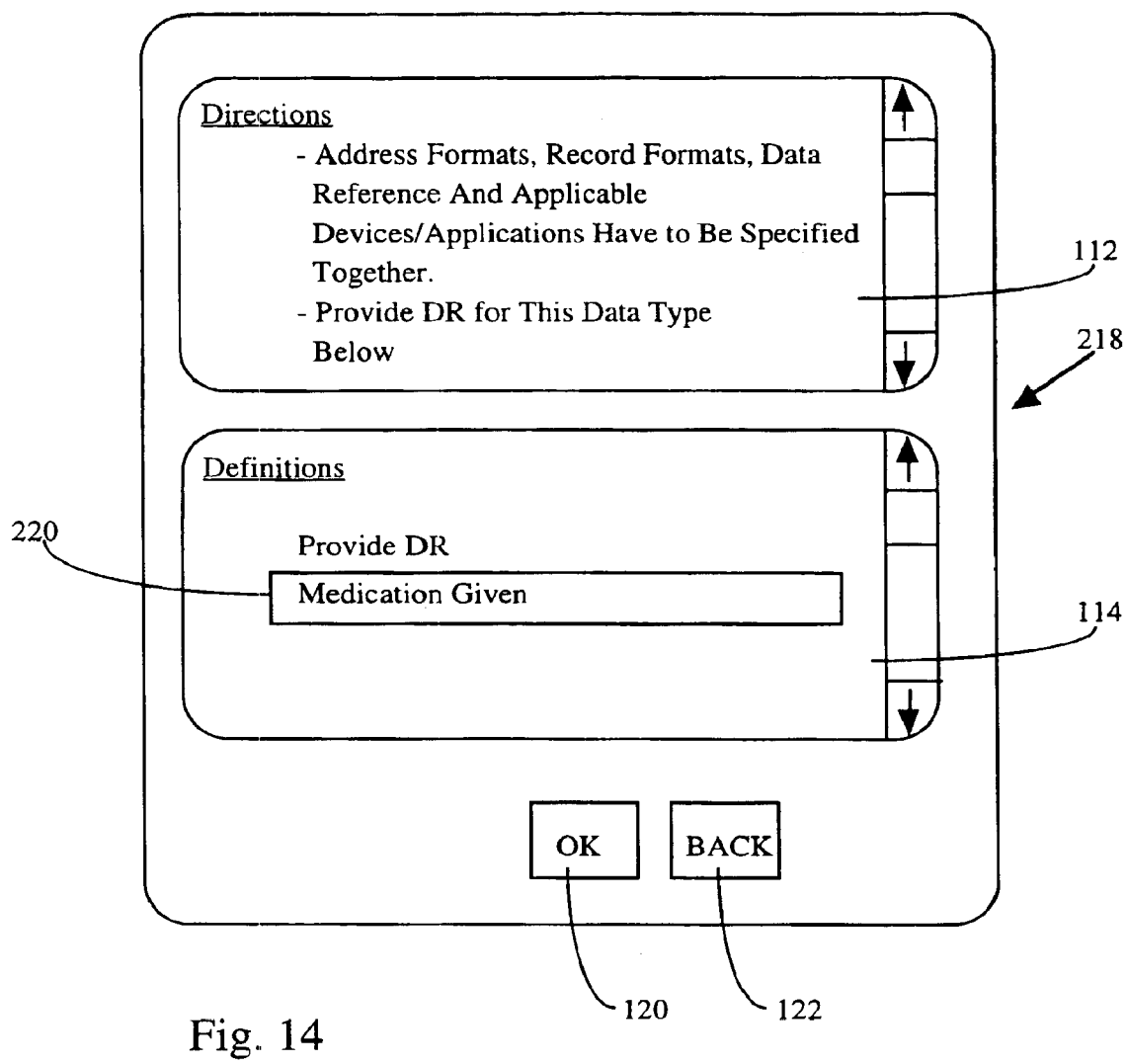
FIG. 14 is similar to FIG. 7, albeit illustrating yet another exemplary screen.
Figure 15:
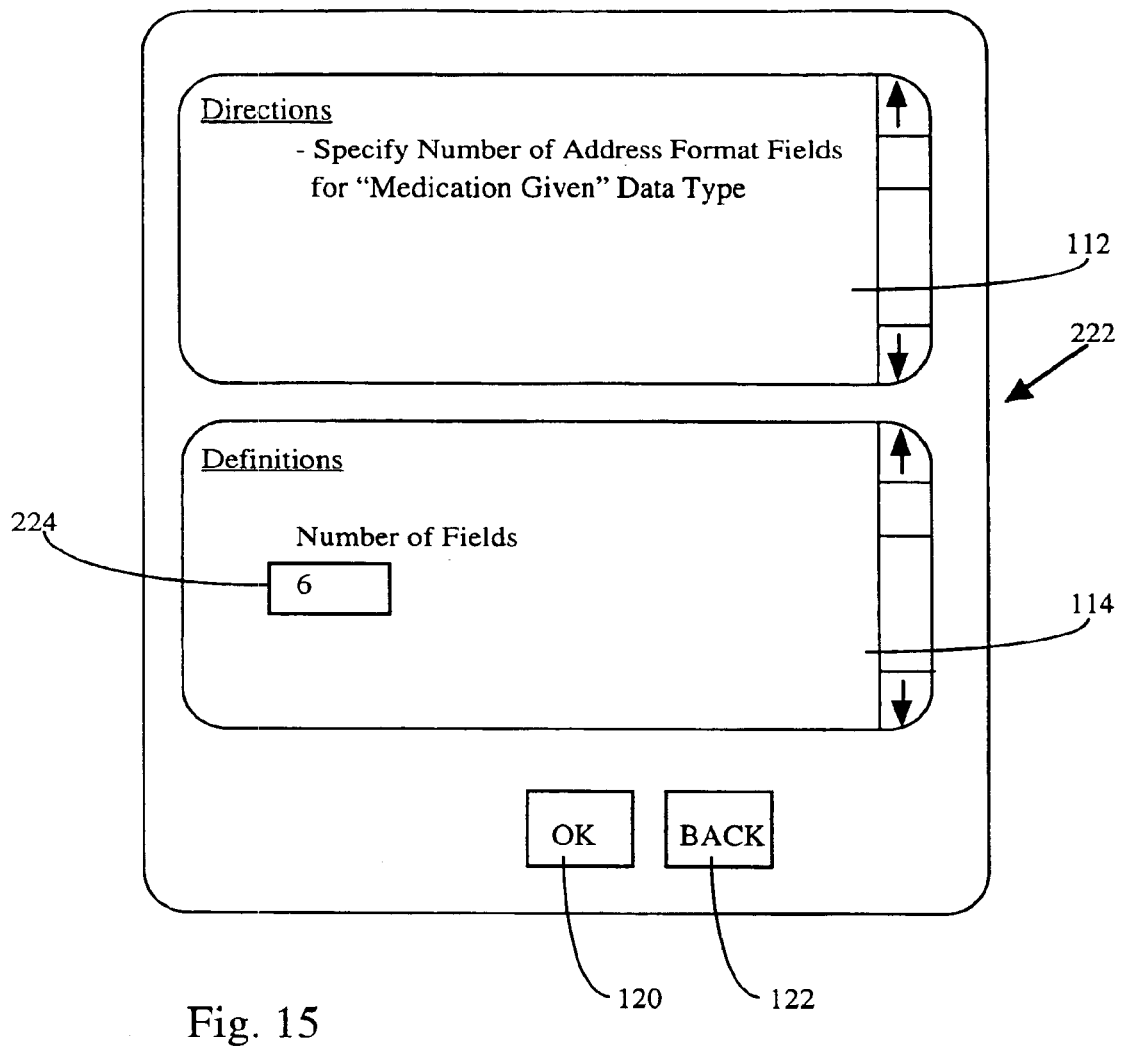
FIG. 15 is similar to FIG. 7, albeit illustrating yet another exemplary screen.

Referring to FIGS. 14 and 15, after the user provides a DR and selects icon 120 in FIG. 14, control passes to screen 222. In section 112, screen 222 instructs the user to specify the number of address format fields which the user would like to have in an address corresponding to the medication given data type. In section 114, screen 222 provides an information box 224. In the present example, referring also to FIG. 3, because ARS 44 includes six fields, the user enters the number 6 in box 224 and then selects icon 120. When icon 120 is selected, referring also to FIG. 16, control passes to screen 226.

In section 112, screen 226 instructs the user to, with respect to the first field in the medication given data type, select a field type from the field type list in section 114. In addition, section 112 instructs the user that, if a desired or required field type does not appear within the list in section 114, the user should select a FIELD EDITOR icon 232 which is provided in the lower right-hand corner of screen 226. Referring also to FIG. 8, when FIELD EDITOR icon 232 is selected, control passes to screen 128 and the user steps through field-specifying screens to define a new field and corresponding rules.

Figure 16:
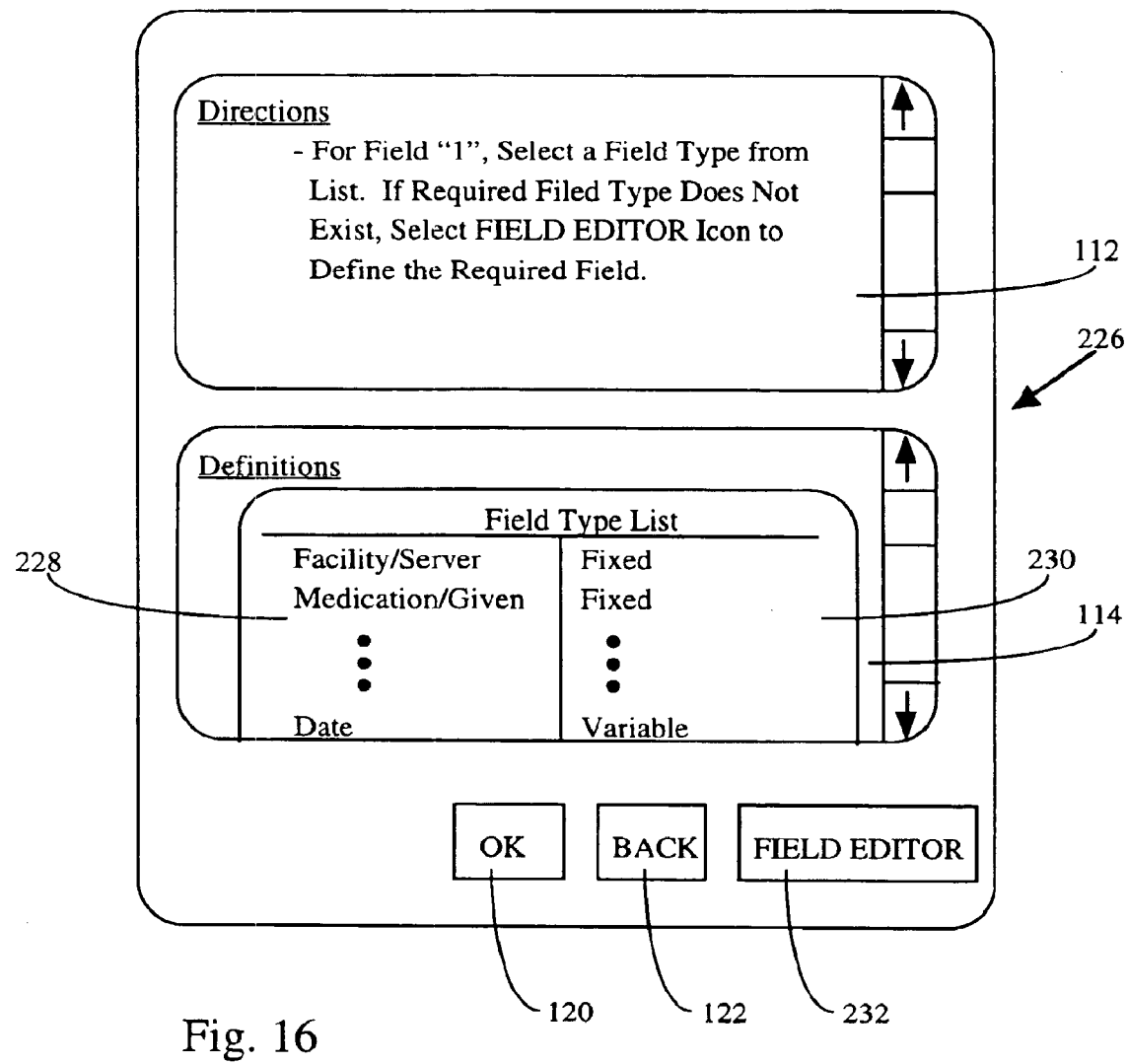
FIG. 16 is similar to FIG. 7, albeit illustrating yet another exemplary screen.

Referring still to FIG. 16, section 114 includes a field type list table having a field column 228 and a type column 230. All of the fields which were specified earlier using the field editor and which are stored on DB 26 are provided in list 228. Exemplary-listed fields include "facility/server," "medication/given" and "date." The general nature of each field in column 228 is provided in column 230. To this end, column 230 indicates whether or not a corresponding field is fixed or variable. Assuming that a required or desired field type is listed in section 114, the user uses a mouse-controlled cursor to select the field and then selects icon 120.

In the case of the first field in any ARS address format, the first field will typically be reserved for a server designating fixed character string. Therefore, in the case of the first field, when screen 226 is provided, it is contemplated that the data type editor may only provide a short field type list comprising system supported server(s) designating fixed character strings. For example, where the system only supports two server designating strings, column 228 only provides the two strings for selection to instantiate the first field.

Similarly, where the system supports only one server designating string, the data type editor may automatically select the supported string for first field instantiation in each address format. For instance, in the present case it is assumed that the only system supported server designating character string is "http://hww.st_mary.springfield" and therefore, the data type editor may be programmed to provide that string in the first field for each address format. In this case, the first time screen 226 is provided, the user is instructed that the first field for the ARS has already been designated by default and that the user should next designate field type for the second ARS field (i.e. field 58 in FIG. 3).

Referring still to FIG. 16, after a field type has been selected or provided for the first field, control passes again to screen 226 which instructs the user to select a field type for the second field in the medication given data type address format. The user again uses a mouse-controlled cursor to select one of the field types in section 114 or, if a desired or required field type does not appear in section 114, selects FIELD EDITOR icon 232 to access the field editor for field defining purposes. This process is repeated for each of the six address format fields in ARS 44. After a field type has been selected for the sixth field and icon 120 is selected in FIG. 16, control passes to screen 233 in FIG. 17.

In section 112, screen 233 indicates that all of the ARS fields for the medication given data type have been specified and instructs the user to specify the number of record format fields for the medication given data type. To this end, in section 114, screen 233 provides an information box 234. The user specifies the number of record format fields in box 234 and then selects icon 120. Referring once again to FIG. 4, because the RRS 46 includes six fields, the user specifies the number 6 in box 234.

Figure 17:
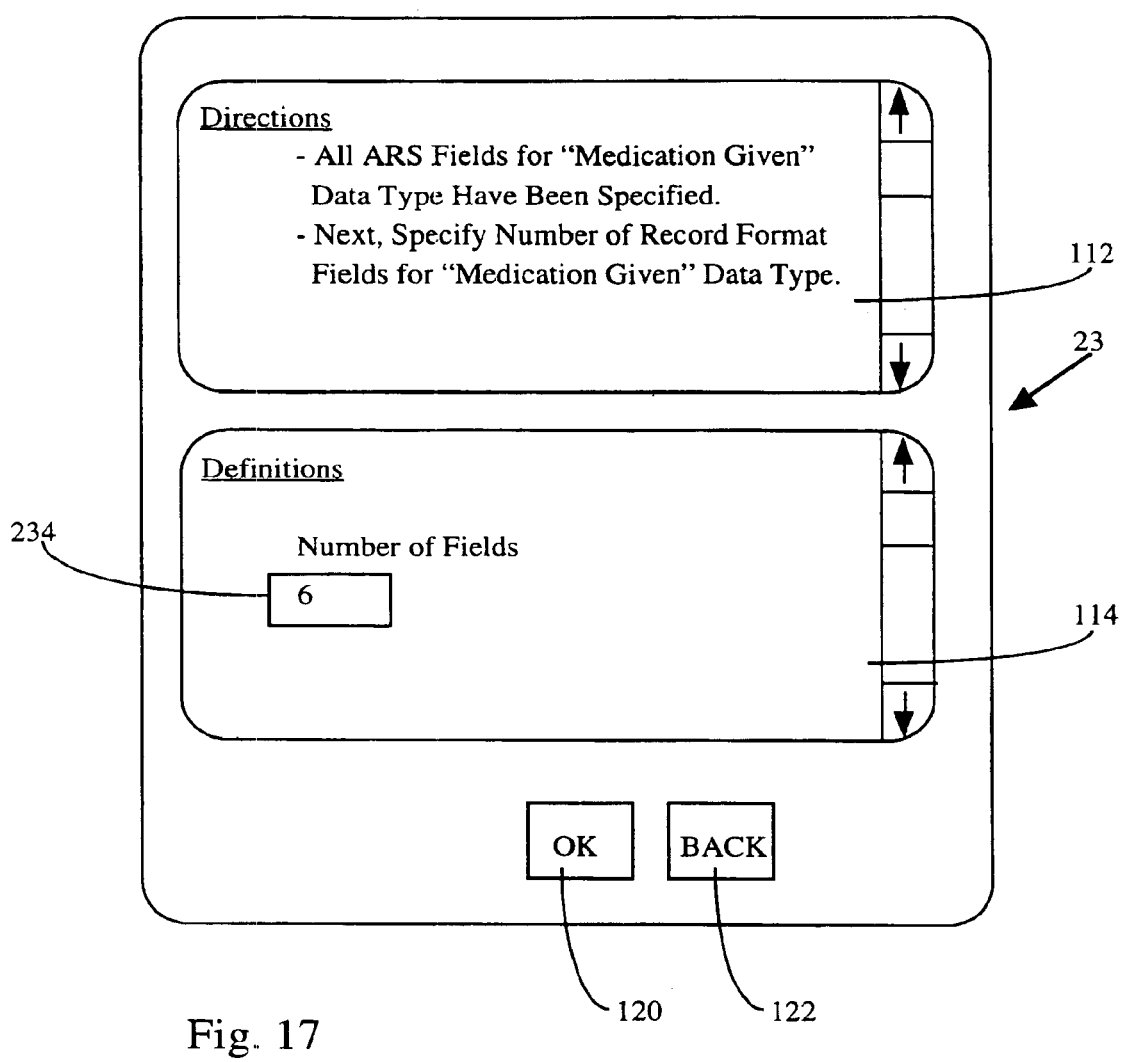
FIG. 17 is similar to FIG. 7, albeit illustrating yet another exemplary screen.

Referring to FIGS. 16 and 17, after the number of fields have been specified in box 234, the user selects a specific field type for each of the six record format fields, one field at a time. Again, if a required or desired field does not exist, the user may select icon 232 to access the field editor and define the required or desired field.

Figure 18:
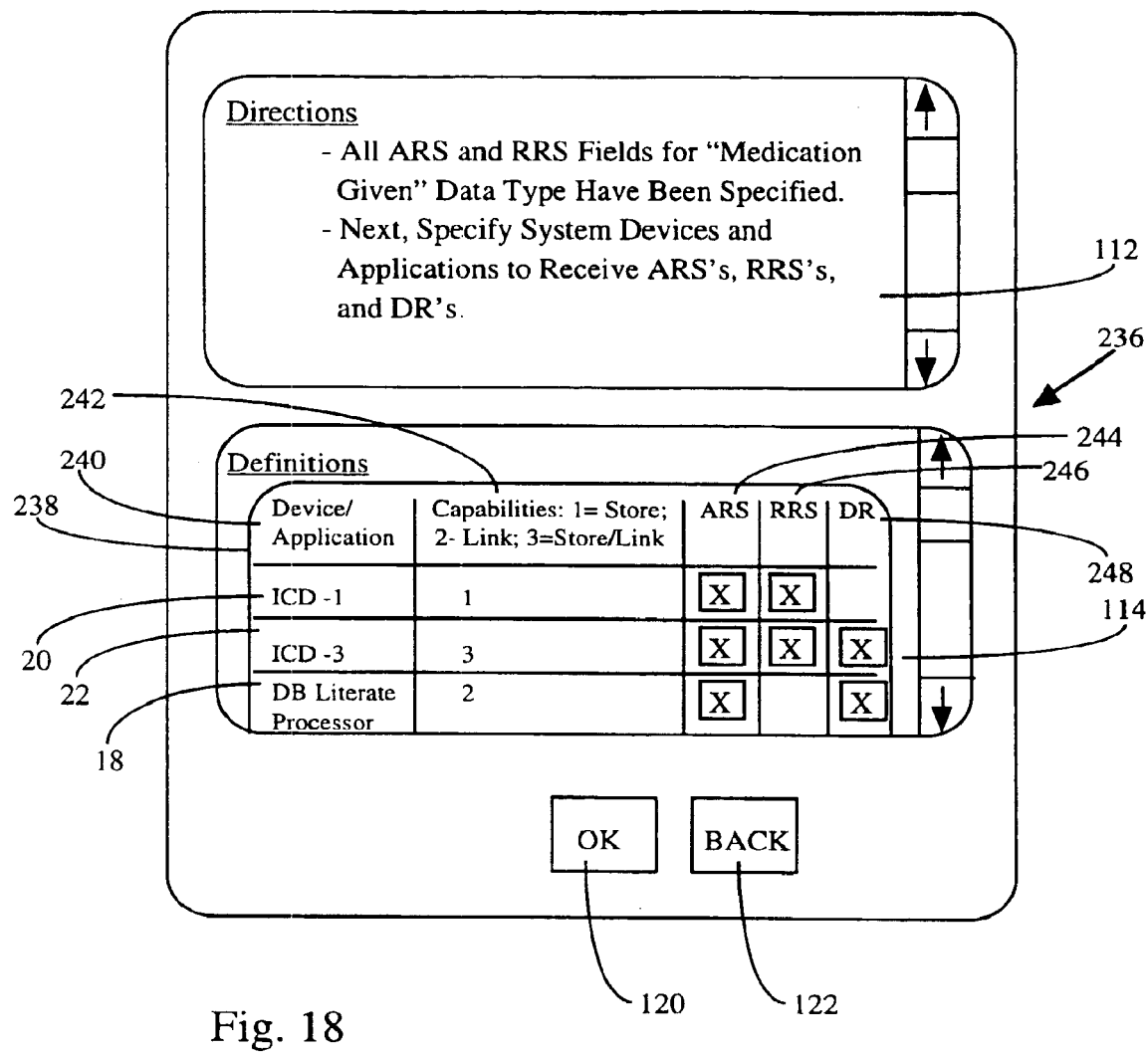
FIG. 18 is similar to FIG. 7, albeit illustrating yet another exemplary screen.

Referring to FIGS. 16 and 18, after field types have been selected for all six record format fields, when icon 120 is selected on screen 226, control passes to screen 236. In section 112, screen 236 informs the user that all the ARS and RRS fields for the medication given data type have been specified and instructs the user to specify system devices and applications which are to receive the ARSs and RRSs and DRs corresponding to the medication given data type. In section 114, screen 236 provides a device specifying table 238 which includes a device/application column 240, a device capabilities column 242 and ARS, RRS, and DR selection columns 244, 246 and 248.

Referring also to FIG. 6, every device and every application included in system 10 which may require any of the ARS, RRS or DR information is listed in column 240. To this end, exemplary listed devices and applications include ICD-1, ICD-3 and DB literate processor 18 (others would be included but are not illustrated). As indicated above, in the present example, ICD-1 is capable of the single database function of storing received information while ICD-3 is capable of both storing received information and forming links between data references in a record and other records corresponding to the data references. Similarly, processor 18 is only capable of forming links between data references in one record and other records corresponding to the data references and, in the present example, cannot generate addresses and records for storing purposes.

To indicate device and application capabilities, column 242 includes a capabilities indicator corresponding to each device in column 240. A key at the top column 242 specifies that a "1" indicator indicates that a corresponding device or application is only capable of storing received information, a "2" indicator indicates that a corresponding device is only capable of linking data references to corresponding references and a "3" indicator indicates that a corresponding device or application is capable of both storing and linking. As illustrated, indicators in column 242 indicate that ICD-1 is only capable of storing, ICD-3 is capable of storing and linking and processor 18 is capable of only linking.

Selection columns 244, 246 and 248 are initially blank in a preferred example of the invention. Depending upon the capabilities of devices and applications, a user will only be able to select a specific subset of the ARS, RRS and DR for provision to each one of the devices and applications. For example, where a device or application is only capable of storing information and cannot link, the device or application is only capable of storing information and cannot link, the device or application would only require an ARS and RRS and would not require a DR. Therefore, with respect to ICD-1, boxes in columns 224 and 246 are highlighted, indicating potential selection while the box in column 248 is not highlighted, indicating unselectability.

Similarly, devices or applications which can both store and link require each of the ARS, RRS and DR. Therefore, each of the boxes in columns 244, 246 and 248 corresponding to ICD-3 are highlighted, indicating possible selection.

With respect to processor 18, because processor 18 can only link, only an ARS and a DR are required and therefore boxes, columns 244 and 248 corresponding to processor 18 are highlighted, indicating possible selection while the box in column 246 corresponding to processor 18 is not highlighted.

Using a mouse-controlled cursor, the user can click on any of the highlighted boxes in columns 244, 246 and/or 248 to indicate that the corresponding information should be provided to associated devices and applications. When a box is selected, a flag is placed therein. The flag can be removed by again selecting the box.

The editor may include rules which insure that, when one type of information is provided to a device or application, other required types of information for that device or application to work properly are also provided. For example, referring still to FIG. 18, if a flag is placed in the box corresponding to column 244 and ICD-1, a flag may also automatically be placed in the box corresponding to column 246 and ICD-1. Other similar rules are contemplated.

Although some devices and applications are capable of both storing and linking (e.g., ICD-3), where a user selects only a subset of ARS, RRS and DR for provision to the device or application, it is contemplated that when the device or application receives the subset of information, the device or application will only perform database functions for which it has sufficient IRS information. For example, in the case of ICD-3 which can both store and link, if a user selects only the ARS and RRS information to be provided to ICD-3, and does not select a corresponding DR for provision to ICD-3, during operation, ICD-3 will not only perform storing database functions and will not perform linking database functions. Similarly, if, upon selection, a user only provides an ARS and a corresponding DR to ICD-3 and fails to provide the corresponding RRS, ICD-3 will only perform linking functions and will not perform record formatting functions and address formatting functions. In this case, it is contemplated that some other system device, upon receiving the corresponding record with links therein, would reorder the information into a proper record format and provide an address which is consistent with a database address format for storage purposes.

Figure 26:
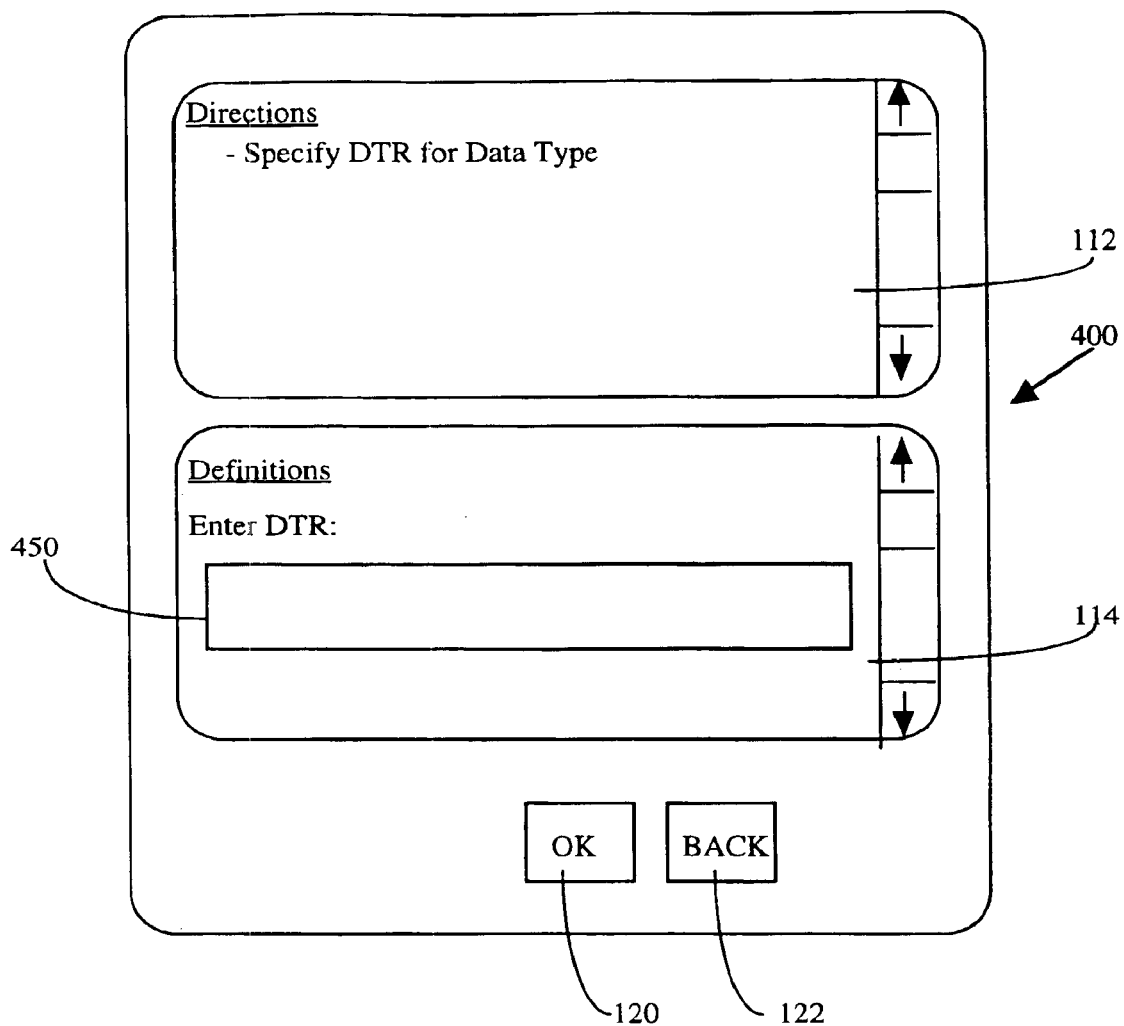
FIG. 26 is an illustration of a screen similar to FIG. 22.

After defining information to be provided to each system, device and application, when the user selects OK icon 120, control passes to screen 400 illustrated in FIG. 26. In section 112, screen 400 instructs the user to provide a DTR. In section 114 screen 400 provides an information box 450 for providing the DTR for data type j. To simplify this explanation it is assumed that the administrator will have a code book which includes reference character strings which can be used as DTRs indicating specific events/procedures, etc. Nevertheless, as indicated above DTR 13 may take more complex forms such as a variable character string (e.g. in the case of a patient ID) or a variable search rule set (e.g. in the case of a medication bar code). In addition, the DTR 13 may include Boolean logic, natural word recognition technology and so on. In any of these cases the data type editor would have to be useable to specify the more complex DTR rules and, in this regard, would have some features similar to the field editor features described above.

Figure 19:
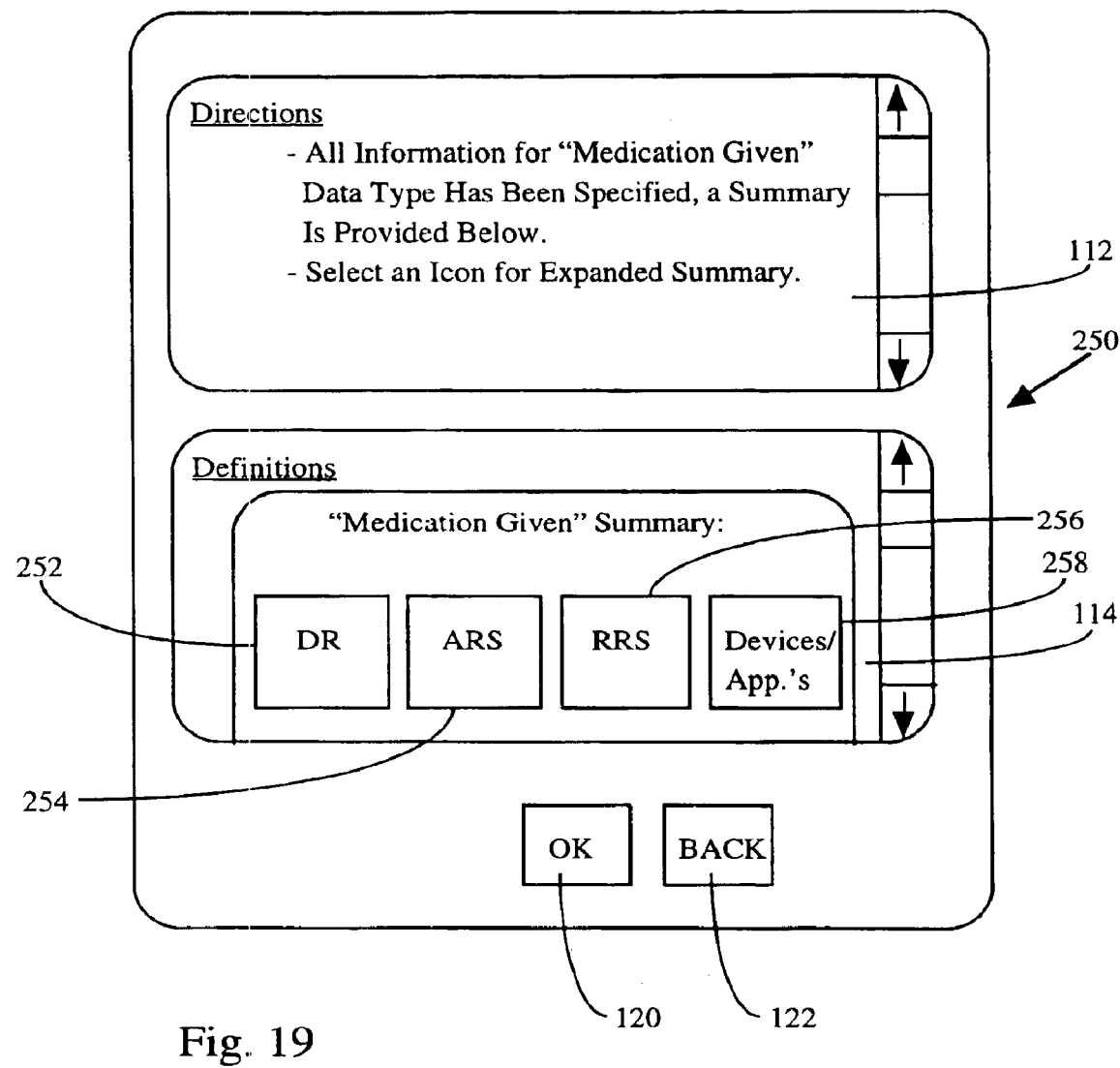
FIG. 19 is similar to FIG. 7, albeit illustrating yet another exemplary screen.

Referring again to FIG. 26, the user provides a suitable DTR in box 450 and then selects icon 120. Referring to FIG. 19 control passes to screen 250. In section 112, screen 250 indicates that all of the information for the medication given data type has been specified and that a summary is provided below in section 114. In addition, section 112 instructs the user to select an icon in section 114 for an expanded summary.

In section 114, screen 250 provides a DR icon 252, an ARS icon 254, a RRS icon 256 a DEVICES/APPLICATIONS icon 258 and a DTR icon 259 corresponding to the medication given data type. Referring also to FIG. 2, icons 252, 254, 256 and 258 correspond to each of the five components 54, 44, 46, 49 and 13, respectively, of RSS 42. Although not illustrated, it is contemplated that by clicking on any of icons 252, 254, 256, 258 or 259, an expanded summary window corresponding to the specific type of information related to the icon is provided. For example, by selecting DR icon 252, the expanded window clearly indicates the DR corresponding to the medication given data type. Similarly, by selecting ARS icon 254, referring to FIG. 3, an image similarly to the ARS image presented in FIG. 3 would be provided on display 88 which graphically depicts the fields in ARS 44, and, possibly, all of the information in field IRSs. Referring to FIGS. 4 and 19, if icon 256 is selected, it is contemplated that an image like the image illustrated in FIG. 4 would be provided, which graphically depicts the fields in RRS 46, indicates the type of field, and, possibly, provides corresponding IRSs for each field. If icon 258 is selected, referring also to FIG. 5, it is contemplated that an image similar to the image illustrated in FIG. 5, would be provided, which indicates system devices and applications and IRS information to be provided to each one of the devices and applications. If icon 259 is selected, then window indicates the DTR (or DTR VSRS).

Referring to FIGS. 7 and 19, after reviewing the medication given data type summaries, the user selects OK icon 120 on screen 250 and control passes again to screen 100. Using screen 100, the user can again select DATA TYPE editor icon 126 to define another data type definition as illustrated in FIG. 2. After all data type definitions have been defined, the user can select FINISH icon 260 in the lower right hand corner of window 100 to indicate that all data type definitions have been specified for system 10.

Referring again to FIG. 6, after data type definitions have been specified using work station 86, each data type definition is stored on one of databases DB-1, DB-2 or DB-3. In addition, subsets of each data type definition are provided to each system device and application to facilitate storing and linking database functions. For example, with respect to the medication given data type in the present example, referring to FIGS. 3 and 6, the ARS and DR are provided to database literate processor 18. Similarly, the ARS and RRS for the medication given data type are provided to ICD-1 and also to ICD-2 via transceiver 94 and are provided to PC-1 via network 84. The ARS, RRS and DR are provided to ICD-3 via transceiver 94 and are provided to PC 14 via network 84.

After receiving required data type definition information, each of the system devices and applications perform storing and linking functions as described above.

D. Topic Specific Record Indication

The field and data type editors described above provide data type definitions which can be used to quickly and easily facilitate system-wide information compatibility providing a comprehensive addressing and recording scheme for both storing and linking DB functions. Nevertheless, despite their advantages, the field and data type editors as described above still have several shortcomings.

First, despite a database administrator's attempts to define all possible data types for storage and linking using an information system, inevitably, there will be some desirable data types which are not recognized during the administrator's defining efforts and therefore are not supported by the administrator's defining efforts described above. For example, a physician may be in the process of analyzing a 3D MRI image of a patient's heart on a workstation screen. The physician may identify a particularly advantageous arterial occlusion view which the physician would like to reference in a subsequently drafted MRI report. It will be assumed the desirable view is a 42° view (i.e. the 3D image has been rotated through a 42° arc about the vertical axis). While the physician may want to reference the view subsequently in the MRI report via a suitable DR, herein it is assumed that a "42° view" DR is not supported by the data specifications previously defined by the administrator and therefore the storing DB function does not facilitate the subsequent linking function.

Second, while the editors described above can be used to define a new data type definition including a "42° view" DR and other RSS information (e.g. see FIG. 2), in cases where a DR may only be used once or a small number of times, the additional benefits associated with defining a required RSS for such cases would likely not justify the time and effort needed to perform such definition. For example, to label the 42° view, generate an address to store the 42° view and provide rules for linking to the 42° view in subsequent documents, a complete address rule set (ARS) (e.g. see FIG. 3) would have to be defined for the 42° view. While the ARS defining process is streamlined using the editors above, the process is still simply too tedious in such a case and would likely be foregone in the present example.

Third, within any given record or information set there may be some subset or segment which is particularly desirable for linking purposes. The 42☐ MRI view described above fits this description. Unfortunately, the editors described above provide no way to earmark sub-set or segment information for linking.

Fourth, it is contemplated that a physician may, when using any system device or application, encounter a data or record segment which, although deemed useful for subsequent linking purposes, is not associated with enough segment distinct information to form a suitable DB address for linking purposes or which may include information which is too specific for an intended use. For example, a physician may be examining a 3D heart MRI image corresponding to a first patient when he encounters a particularly good image of a specific occlusion type. While the image is associated with the first patient, the physician may want to link to the image in a text report corresponding to a second patient. Even if an address could be assigned to the image as described above, the image would only be associated with the first patient, not the second, and would not be liable in the second patient report.

One solution to this problem would be to provide a system wherein any data segment can be highlighted or selected and given a unique DR for subsequent linking purposes. Unfortunately, such a system would quickly become DR saturated as DRs would have to remain unique. In other words, once the phrase "42☐ view" is used for one patient's image, the phrase "42☐ view" could never again be used to refer to any other segment or information sub-set without causing system confusion.

To facilitate a more user friendly system for earmarking records and record segments with DRs for linking purposes in cases where a DR may only be used seldomly, may only be used with a small number or subset of other records, or may only be recognized as advantageous during a post-defining process, the present invention contemplates yet another software application which operates in conjunction with other workstation software and one or more special "general" data types and corresponding RSSs. Hereinafter this application will be referred to generally as a "designator" application. To support the designator application, each of the data type editor described above and the DB literate processor described above and in other patent applications which have been incorporated herein by reference have to include additional features described below.

Next, the general data type will be described. Then, an exemplary technique for using the data type editor to define the general data type is described followed by a description of how the general data type can be used to earmark records or data segments with unique DRs for subsequent linking purposes.

Figure 20:
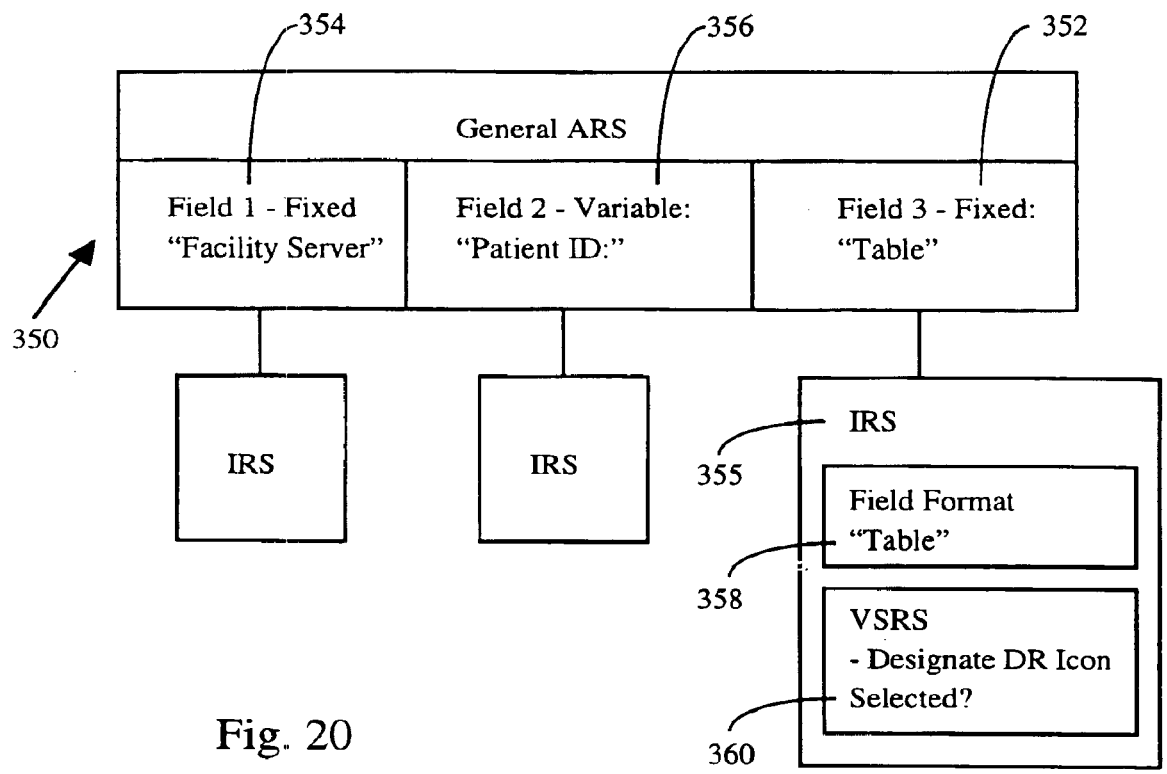
FIG. 20 is a schematic diagram illustrating a general ARS according to the present invention.
Figure 21:
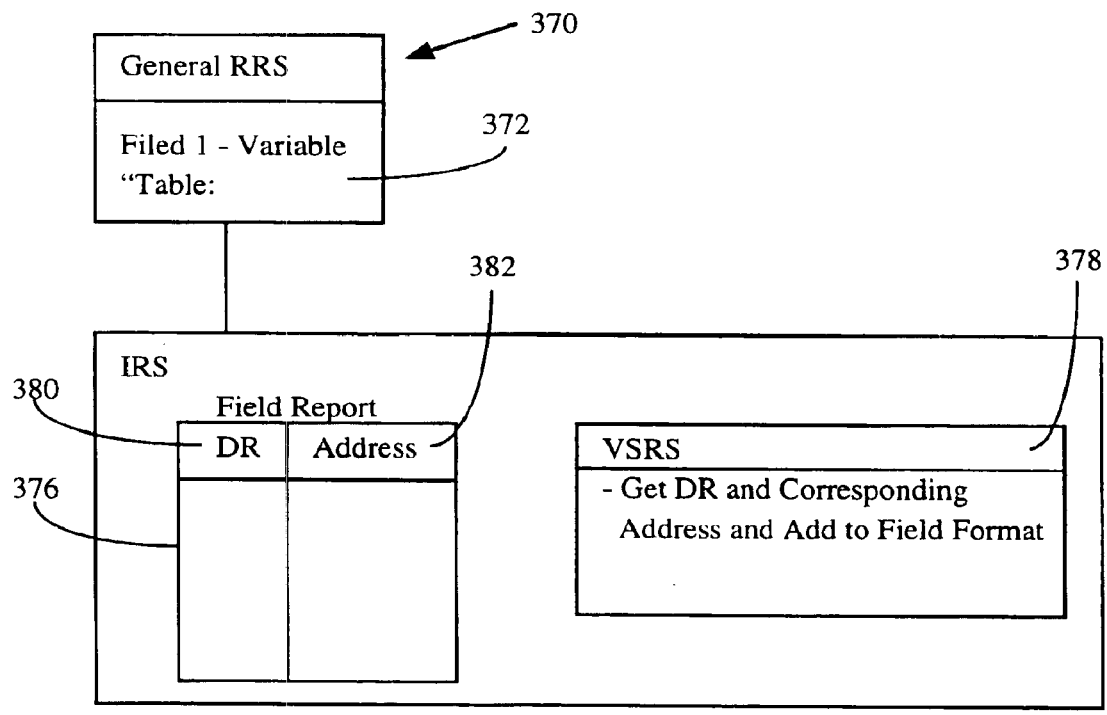
FIG. 21 is a schematic illustrating a general RRS which corresponds to the ARS of FIG. 20.

Referring now to FIGS. 20 and 21, an exemplary general ARS 350 and corresponding RRS 370 are illustrated which constitute a general data type. Referring also to FIG. 3, ARS 350 is similar to ARS 44 except that ARS 350 has a reduced field set and includes a different field combination. Fields in ARS 350 and ARS 44 having identical names have identical IRSs. Thus, fields 354 and 356 and corresponding IRSs are identical to fields 56 and 60 and corresponding IRSs, respectively.

IRS 355 corresponding to field 352 includes a fixed field format comprising a character string "table" 358 and a VSRS 360 which indicates that ARS 350 should be accessed when a "DESIGNATING DR" icon is selected. An exemplary DESIGNATING DR icon is described below.

Referring still to FIGS. 20 and 21, exemplary RRS 370 corresponding to general ARS 350 includes a single variable table field 372 and a corresponding IRS 374. IRS 374 includes both a field format 376 and a VSRS 378. Format 376 defines a simple table having both a DR column 380 and an address column 382. Hereinafter format 376 may be referred to as table 376. As explained in more detail below, as DRs are provided by a system user which are not supported by specific data types, the DRs are added to column 380. In addition, as a specific record, data set or data segment is earmarked with a distinct DR, the system address corresponding to the record data set or segment is provided in column 382 in a row corresponding to the earmarking DR.

Exemplary VSRS 378 includes a single rule for instantiating format 376. The rule specifies that a DR provided by a user to earmark a record and a corresponding record address should be retrieved and used to instantiate table 376.

Referring to FIGS. 3 and 20, ARS 350 is defined using the data type editor in a manner similar to the manner described above in conjunction with ARS 44 with a few distinctions. The distinctions are highlighted by the following example. In the following example it is assumed that during data type definition a system administrator at the St. Mary's facility would like to define only one general data type and that the general type should take the form illustrated in FIGS. 20 and 22. Thus, DRs and corresponding addresses are to be grouped into tables (e.g. see 376 in FIG. 21) corresponding to individual patients for subsequent linking.

In this example, in the interest of simplifying this explanation, many of the screen illustrations described above are again used to describe the general data type defining process. However, additional useful screen illustrations are also described. The intermittent additional screens described hereinafter do not affect operation of the data type editor as described above but rather supplement that operation.

Figure 22:
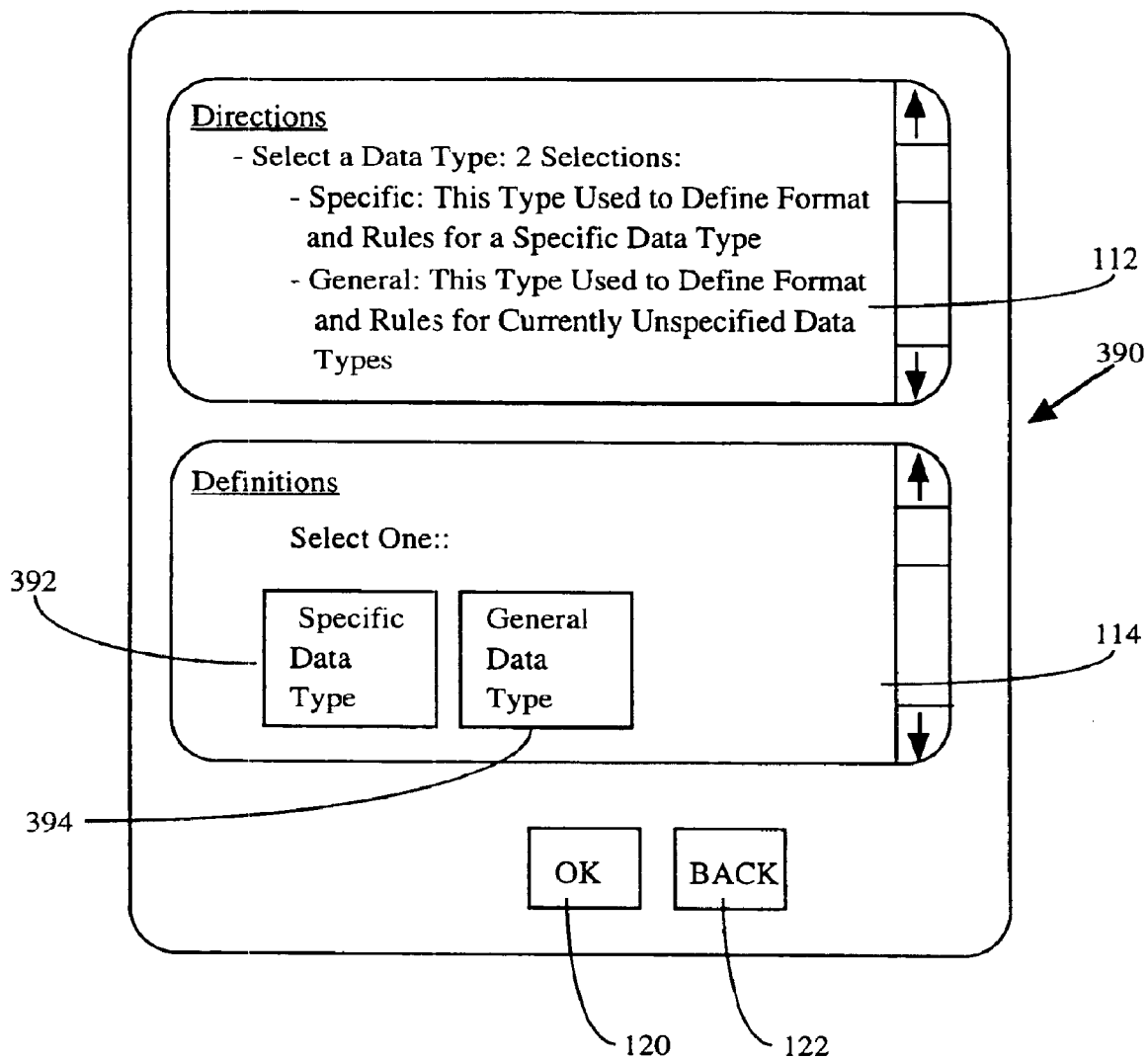
FIG. 22 is an illustration of an editors screen similar to the screen of FIG. 7.

Referring again to FIG. 7, in this example, after DATA TYPE editor icon 126 is selected, control passes to screen 390 in FIG. 22. In section 112, screen 390 instructs the user to indicate if a data type to be defined is a specific type or a general type. Specific means a type which will be fully supported by a distinct data type definition. For example, the data type j (i.e. medication given) described above is a fully supported specific data type. General means a data type for which a DR has not yet been provided.

In section 114, screen 390 provides a "SPECIFIC DATA TYPE" icon 392 and a "GENERAL DATA TYPE" icon 394. If icon 392 is selected, referring to FIG. 14, control passes to screen 218 which begins the process of defining a specific data type definition. Referring to FIG. 15 and 22, if icon 394 is selected, control passes to screen 222.

In section 112, screen 222 instructs the user to specify the number of fields for the "general" address format (i.e. the phrase "medication given" in section 112 is replaced by the word "general"). In addition, section 112 may also provide additional instructions for the user. For example, it is contemplated that a general address format will require at least three fields and this instruction may be provided.

In section 114 the user provides the number in box 224. In this case, referring again to FIG. 20, ARS 350 includes three fields and therefore the user provides "3" in box 224 and selects icon 120.

Referring to FIGS. 15 and 16, when icon 120 is selected on screen 222, control passes to screen 226. Referring also to FIG. 20, using screen 226 and subsequent screens, the user selects field types for fields 354 and 356 in the manner described above. In the case of a system including only one server, field 354 may automatically be defined by the editor.

In the case of a general data type at least one field in an ARS, in the present example field 352 in ARS 350, is always automatically defined by the editor as a table field corresponding to fixed IRS 355. Thus, after defining fields 354 and 356, all fields for general ARS 350 have been defined.

Referring to FIG. 21, in the case of a general data type the RRS 370 is also automatically defined by the data type editor and has the form illustrated. There is no DR or DTR for the general data type and, in the present example it will be assumed that the general data type is provided to all system devices and applications so that the D/A list (see 69 in FIG. 2) does not have to be specified. Thus, after defining ARS 350 fields, control passes again to screen 100 in FIG. 7.

Operation of the designator application software will now be described. The designator application will be described in the context of an MRI viewing workstation. For the purposes of this explanation, it will be assumed, referring again to FIG. 6, that station 86 is an MRI station and that MRI image viewing and manipulation software is loaded onto processor 90.

Figure 23:
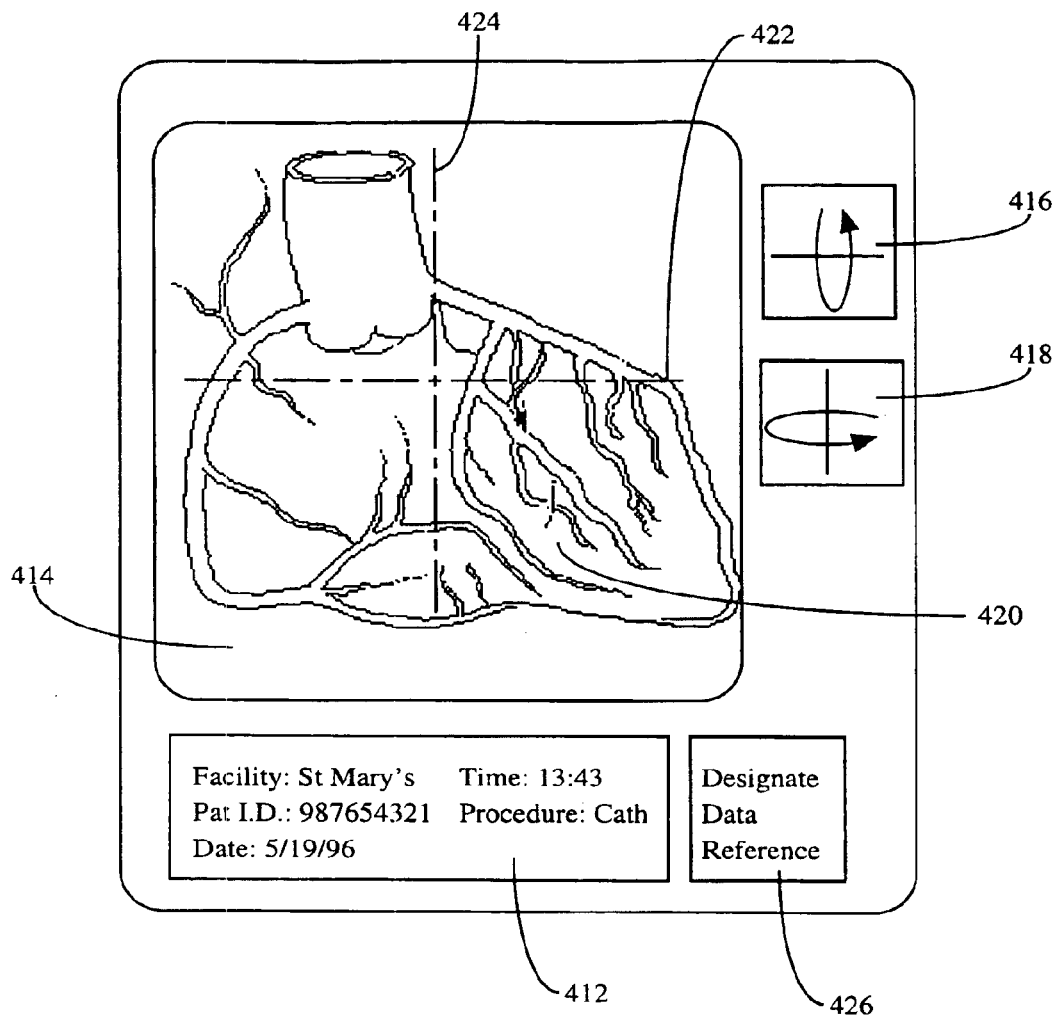
FIG. 23 is an illustration of an imaging screen.

Referring also to FIG. 23, an exemplary MRI imaging screen 410 which includes an information window 412, an image window 414 and manipulation icons 416 and 418 and which is provided on screen 88 is illustrated. Consistent with the example above, the designating editor will be described in the context of a 3D MRI heart image 420 provided in window 414.

Window 412 specifies information about the image being displayed including the medical facility "St. Mary's, Springfield", patient ID # "987654321", the date the image was generated "5/19/96", the time of generation "13:42" and the type of imaging procedure, "MRI". Icons 416 and 418 are useable to rotate image 420 about horizontal and vertical axis 422, 424, respectively. Icons 416 and 418 are individually selectable using a mouse controlled cursor. Other tool icons are contemplated but not illustrated.

The designating application is minimally invasive and preferably only includes a "DESIGNATE DATA REFERENCE" icon 426 in a peripheral screen area (e.g. in the lower left-hand screen corner). During image examination, when a physician observes a particularly interesting heart view in window 414, the physician can earmark the view for subsequent linking purposes by selecting icon 426.

Figure 24:
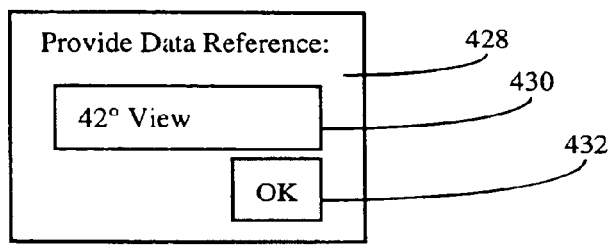
FIG. 24 is an illustration of a window used in conjunction with an exemplary designating application according to the present invention.

In the previously described example, assuming the physician notices an occlusion which is advantageously observable in a 42° view, referring to FIGS. 23 and 24, with the 42° view displayed in window 414, when icon 426 is selected, the designator application opens window 428. In window 428, the designator application instructs the physician to provide a data reference for the displayed image and also provides an information box 430 and an "OK" icon 432. Again, the DR provided should be indicative of the data which the DR references. The physician enters a DR in box 430. In the present example, the DR is "42° view" which is consistent with the displayed image.

When icon 432 is selected, screen 410 is again provided. The physician may identify a second image view of interest for subsequent linking purposes. Once again, the physician may select icon 426 to provide a unique DR for the second image and so on.

Referring to FIGS. 20, 21, 23 and 24, when icon 426 is selected on screen 410, in addition to providing screen 428 to the user, the designator application also uses ARS 350 to build an address which corresponds to a DR table for the specific patient identified in information window 412. To this end, the application fills in fields 354 and 352 generically, gleans the patient ID# from window 412 and then fills in the patient ID# in field 356. Moreover, when icon 426 is selected the application uses the table address to access a record corresponding thereto or, if a record does not yet exist, uses RRS 370 to form a record for receiving the DR when provided.

After a record address has been formed and a corresponding record has either been accessed or formatted, the application waits for the user to provide a DR in box 430 (see FIG. 24). When a DR is provided in box 430 and OK icon 432 is selected, the application performs two functions. First, the application provides the DR in table 376. Second, the application identifies the current system address at which the 42° view is stored and provides that address in column 382 in a row along with the earmarking DR.

Hereinafter it will be assumed that, among other data segments and information sub-sets, the physician selected a 42° view, a 68° view and a 135° view and earmarks those views with distinct DRs. An exemplary DR table 440 corresponding to patient ID #987654321 is illustrated in FIG. 25.

Although not illustrated, when a DR is assigned to a specific data set via DR table 440, a flag is stored in a record table which earmarks the corresponding address and record for "continued storage". In this regard, data marked for continued storage remains stored even when a larger data set of which the marked data is part is deleted. For instance, in the above example, assuming the physician earmarked the 42° view as a DR included in table 440, the view and its address at ADD-P are flagged for storage even if the larger data set including the 42° view is purged from the corresponding database or is achieved for long term storage.

After a DR table 440 has been generated for patient #987654321, when other system DB literate applications are used to generate or review records and database constructs corresponding to patient #987654321, the applications automatically form links to records corresponding to table DRs.

For example, when a physician enters a DB literate word processor to generate a report concerning patient #987654321, it is contemplated that the processor will require entry of the patient ID # in a specific field. Referring again to FIG. 20, when the patient ID number is provided, the processor automatically accesses ARS 350 and uses ARS 350 to build the address for table 440 (see also FIG., 25). Then the processor copies table 440 into its own memory for use during data entry by the physician.

As the physician enters data, if one of the DRs in table 440 is entered, the processor forms a link to the record at the corresponding address. To this end, the processor provides the DR as a selectable segment in the record text which is linked to the address. When the selectable segment is selected, the processor retrieves the record at the linked address and provides the record to the physician for review. If desired, the processor may provide an expandable window to the physician which includes a list of DRs from table 440 to help the physician remember earmarking DR syntax.

It is contemplated that, instead of providing only one general data type, some systems may facilitate use of two or more general data types. For instance, referring again to FIGS. 20 and 21 in the example above, in addition to the patient specific ARS 350 and RRS 370 which groups DRs and corresponding data segments and information sub-sets according to patient ID #s, a second general data type may include an ARS and RRS which group DRs and corresponding data segments/sub-sets according to procedures. For example, in FIG. 20, instead of providing a variable patient ID field 356, field 356 may include a variable "procedure" field.

In a system capable of supporting more than one general data type, the data type editor would require at least one additional screen (not illustrated) to enable a user to name the different general data types. This screen would be provided between screens 390 and 222 (see FIGS. 15 and 22). Hereinafter it is assumed that the administrator has defined two general data types named "patient" and "MRI".

In addition, the designator application also requires an additional wrinkle. To this end, referring to FIGS. 23 and 27, when icon 426 is selected, the designator application provides an additional screen 500 which, in section 112, explains that there are two different general data types which group segments according to patient # and procedure (e.g. MRI, PET, post-op eval, etc.). In section 114 screen 500 provides both a "PATIENT" icon 502 and a "PROCEDURE" icon 504. The general data type is selected by selecting one of icons 502 and 504.

After one of icons 502 or 504 is selected and ok icon 120 is selected control passes to screen 428 in FIG. 24 where a suitable DR is provided. Thereafter, when control returns to FIG. 23, if desired, the physician may again select icon 426 to earmark the displayed image for inclusion in the previously unselected general data type. Thus, one image may be earmarked for inclusion in two general data types.

In this regard, however, and generally, it should be understood that whenever two DRs may be subsequently simultaneously accessed by a single DB literate processor, the DRs must be unique so that links are not caused between a selectable segment and more than one stored record. Thus, each DR must be unique as DRs in tables corresponding to general data types are accessible to DB literate processors along with DRs corresponding to specific data types. In addition, to use such a system, a DB literate processor would require a system user to provide, in addition to a patient ID #, a procedure indication so that, prior to identifying DRs, the processor could access and retrieve the procedure DR table. Moreover, the user may also be required to provide a date for use by the processor where more than one of a specific procedure type is stored.

Where a general data type which groups data and information in tables corresponding to procedures is provided, it should be appreciated that records and data can easily be shared among various patient reports if desired. Thus, if it is described to link to an image corresponding to a first patient's MRI in a second patient's MRI report, such listing can be supported.

E. Other Preferred Embodiments and Features

1. Temporal Modifiers

The address defining, storing and linking tools and methods described above facilitate many useful functions and are particularly advantageous in cases where all of the information required for a particular address format is known. For example, referring again to FIG. 3A, where both the specific date and specific time (i.e. information in fields 62 and 64, respectively) at which a medication was administered is known or can be gleaned. An address rule set (e.g. see FIG. 3) can be used to generate an address like address for storage and linking purposes. Resolving date and time for storage purposes is typically not problematic as the processor or ICD which receives an information set for generating a record often is able to independently identify date and time for the record or, in the alternative, will be provided with a corresponding date and time in the received information set.

Unfortunately for linking purposes, date and time is not so easily resolvable in many cases. For example, assume a physician is using a DB literate processor as described above to enter a text report corresponding to a particular patient. Also assume that the physician would like to reference, via a hyperlink, an ECG report which was generated several months ago when the patient was admitted to a medical facility for an extended stay. In this case, DB literate processors have a number of shortcomings. First, in this example it is likely that the physician will not remember the specific patient admission date. While a date may not be required by all ARSs. Clearly many and perhaps most ARSs will require some type of temporal modifier. For instance, whenever more than one record of a particular type may be generated for a particular patient, the likely differentiator will be based on time (i.e. date and time). In the case of an ECG, several ECG's may be performed on a patient during the patient's lifetime, during a particular facility stay or, indeed, even during a single day. For this reason, the physician would have to be able to identify at least an admission date in order to identify an admission ECG. This date requirement is burdensome and in many cases may cause the physician to disable the linking feature instead of requiring additional work by the physician.

Second, even if a physician determines an admission date for linking purposes, in some cases more than one ECG may have been performed on a patient on a specific admission date. In this case, the DB literate processor could become confused or could provide an undesired ECG report.

Third, sometimes an ECG report may be generated after or before an admission date. For example, a patient may be examined via an ECG one day prior to actual admission. For another example, a patient may be examined via an ECG two days after an admission date. In these cases, it would be difficult for a physician to quickly identify a desired ECG report for hyperlinking purposes.

One solution to this problem is described in U.S. Pat. No. 6,345,268 entitled "Method and System for Resolving Temporal Descriptions of Data Records in a Computer System" which issued on Feb. 5, 2002 which is commonly owned with the present application and which is incorporated herein by reference. According to that invention, time ranges and instructions are provided for each of several possible temporal descriptors associated with a record. When a temporal descriptor is identified, a processor applied the time range and instructions to the descriptor to identify the address of a record corresponding to the descriptor. While advantageous, unfortunately this solution has at least one shortcoming. Specifically, this solution requires pre-defined addresses associated with each temporal descriptor and cannot automatically construct addresses using address formats.

While described herein in the context of an ECG report, it should be appreciated that temporal resolution difficulties occur in most DB literate linking applications. As another example, if a physician would like to identify whether or not a particular medication was administered to a patient after an operation, the physician may use a DB interface tool which allows the physician to fill in a few fields and receive information corresponding to the patient. For example, the fields may require patient ID at a minimum. Entering just patient ID, however, would obviously generate a large number of related records, many of which have nothing to do with medication or post-op practices. To narrow the records identified another field may require an event (e.g. medication given) and another field may require a date restriction (e.g. a specific date or a date range). While this retrieval tool would be helpful, again the physician may not recollect the operation date and therefore would have a difficult time specifying a date or a date range.

To overcome the problems of resolving which record is identified by a specific DR, the present invention contemplates a system which, in addition to supporting the DRs, also supports temporal modifier references (MRs). An MR is a descriptor which is commonly used in conjunction with a corresponding DR to distinguish one record from another where the records are of the same type. A temporal MR distinguishes records based on time. For example, with respect to an ECG DR, one temporal MR is "admission." Other exemplary MRs include "post-op," "discharge," "most recent" and so on. In addition to specifying MRs, the invention also provides temporal rule sets (TRSs) for determining which records may be referenced by a particular DR/MR combination and, where more than two records fall into the referenceable category, to resolve which of the records should be linked to a specific reference.

To this end, referring again to FIG. 6, preferably system 10 further includes a temporal reference definition system (TRDS) 600 linked to network 84. Referring also to FIGS. 28 and 29, TRDS 600 generally includes a database for storing a temporal descriptor definition table 602 and a plurality of temporal descriptor definitions (TDDs) (one TDD illustrated as 604).

Table 602 includes a DR list 603 including all of the DRs supported by system 10. Consistent with the present example are of the listed DRs is "ECG" 606. In addition, table 602 includes a separate TDD (e.g. 604) for each DR listed.

Referring still to FIGS. 28 and 29, exemplary TDD 604 includes two columns, a modifier reference (e.g. temporal descriptor) column 608 and a temporal rule set (TRS) column 610. Column 608 lists all possible MRs which correspond to an associated DR. In the present example, exemplary MRs associated with the ECG DR include "admission" 612 and "discharge" 614. Many other MRs are contemplated.

Hereinafter it is assumed that all records for which a temporal reference may be required include at least a date field and perhaps also a time field in their DB addresses. In addition, it is assumed that dates and times of all major events which are likely to be used as DR temporal descriptors are stored in one of the system DBs. For example, an admit/discharge/transfer (ADT) system generates records for storage indicating admission, discharge and transfer times and dates. Other system devices are used to memorialize operation dates, examination dates and other important dates. Thus, referring still to FIG. 29, for a particular patient, a specific date (and perhaps time) is associated with admission MR 612 while another specific data is associated with discharge MR 614.

TRS column 610 indicates rules for identifying one record which is referenced by a specific DR/MR combination and therefore a separate TRS is provided for each MR in column 608. The TRS corresponding to MR 612 is identified by numeral 616. The TRSs in the present example have similar configurations and are used in similar manners and therefore only TRS 616 is explained here in detail.

TRS 616 includes three distinct rule subsets including a prior to event time range 618 (PRTR), a post event time range 620 (POTR) and a resolving rule 622 (RR). The PRTR indicates a time range prior to the specific date associated with a corresponding MR. Similarly, the POTR indicates a time range after the date associated with the corresponding MR. For example, with respect to admission MR 612, PRTR 618 may specify a time range of two days prior to the admission date while POTR 620 may specify a time range of three days after the admission date. These time ranges will be assumed hereinafter for the purposes of this explanation.

RR 622 includes a set of rules which can be used to, when more than a single record corresponds to a DR/MR combination and falls into the range specified by PRTR 618 and POTR 620, determine which record to select for linking purposes. RR 622 may be extremely simple such as selecting a record corresponding to a time which is temporally closer to the admission date and time than any other record or selecting a record having the aforementioned characteristics but which is subsequent to the admission date. In the alternative RR 622 may be extremely complex requiring weighting of various factors, accounting for the physician generating a report, accounting for the department of a particular physician (e.g. each department may have different temporal rule requirements) and so on. Many other rules are contemplated.

It has been recognized that, despite attempts to support all MRs which may be used with a specific DR, in some cases an unanticipated and therefore unsupported MR may be employed by a system user or, in some cases, a user may not provide an MR despite the requirement for an MR. To deal with these occurrences, column 608 (see FIG. 29) further includes a "no match" condition 624 and a corresponding set of "no match rules" 626. No match simply corresponds to a condition wherein, after a DR has been identified, none of the MRs in column 608 has been located and therefore, as the name implies, no MR match has been found.

Rules 626 provide processor rules to be followed when the no match condition occurs. Rules 626 may take any of several different forms. For example, where a DR is identified but no MR is identified, rules 626 may cause an information window to open on a display screen to indicate that an MR is required and may provide an MR list to the user for selection. In the alternative, rules 626 may simply specify that where a no match condition occurs, no link is made. As another example, rules 626 may specify that in the absence of an MR, the most recent record corresponding to the DR should be linked. Hereinafter, while various rules 626 are contemplated, it will be assumed that rules 626 specify that when no match occurs, no link is formed.

Referring still to FIG. 29, although not illustrated, TDD 604 may also include a rule set for each MR in column 608 which is similar to the instantiation rule sets described above. For example, the rule set may include various permutations of the corresponding MR for searching purposes. For admission MR 612, the rule set may include "admission," "admit," "adm.," etc. so that, during searching for an MR, virtually all possible permutations are sought. In addition, the rule set may also include rules for where to search for an MR. For instance, one rule may indicate that, when a DR is identified, a processor should search the three terms before and the three terms after the DR for any permutation of a specific MR. Other MR searching rules are contemplated.

Hereinafter, to simplify this explanation, it will be assumed that the rules for searching for an MR are extremely simple. To this end, first, it will be assumed that an exact MR must be located (i.e. no permutations are searched). Second, it will be assumed that only the word or character string immediately preceding a DR is searched to find an MR.

Although not illustrated here, it should be appreciated that additional editor features could be added to the editors described above for specifying temporal descriptor definitions and MRs for each DR and that much of the information required to support such specification could be pre-defined for repeated use during defining. For example, in many cases MRs for a specific facility will be identical or substantially identical for various DRs. For instance, each of an ECG and a PET DR may be modified by an "admission" MR. Similarly, each of the ECG and PET DRs may be modifiable via a "discharge" MR and so on. Thus, the advantages of predefining described above can be used to streamline TDD defining.

Referring still to FIGS. 28 and 29, assuming a complete temporal descriptor definition table 602 and corresponding TDDs (e.g. 604) have been stored on system 600, operation of processor 18 to form links between DRs in one document which reference other documents will be explained in the context of the following example.

Figures 27, 30:
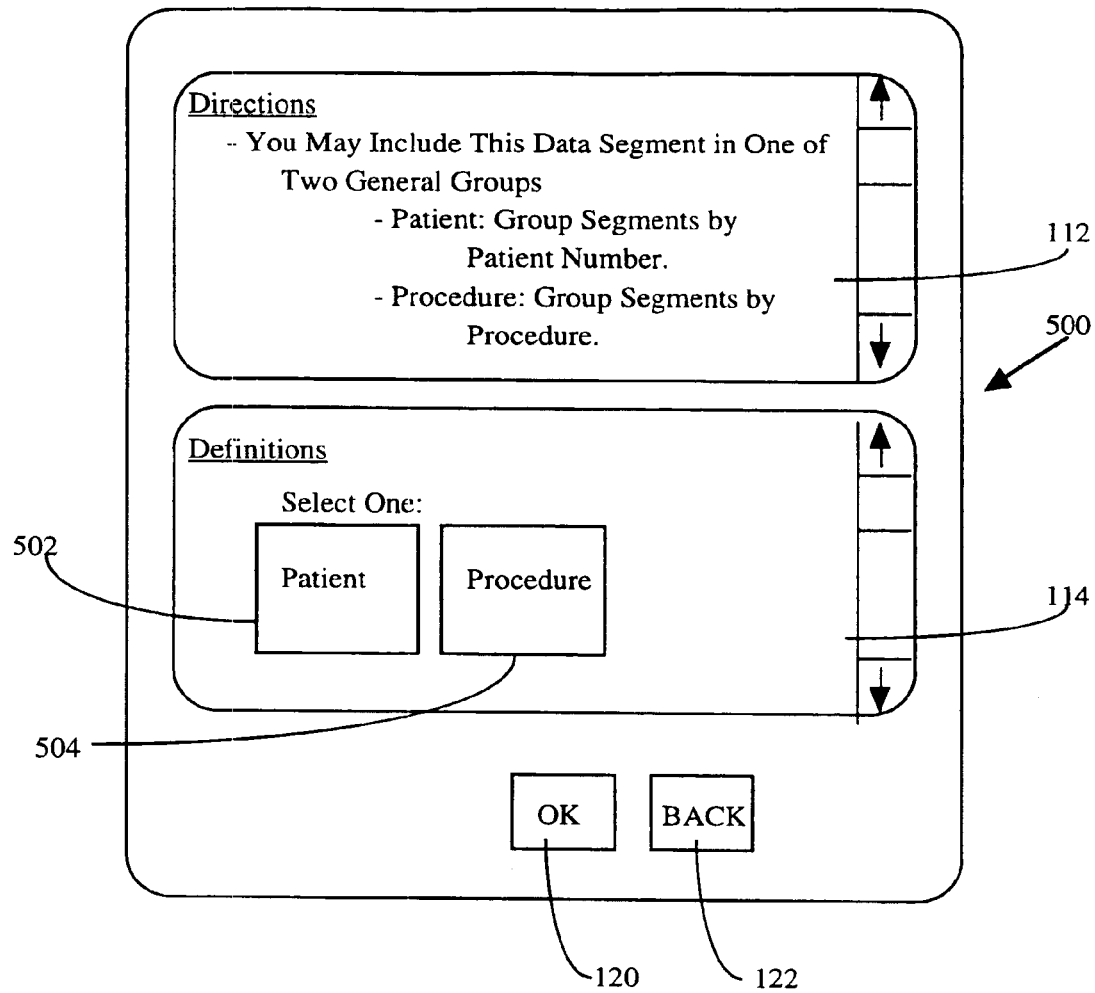
FIG. 27 is an illustration of a screen similar to FIG. 22.
FIG. 30 is a schematic diagram of an exemplary address rule set according to the present invention.

In this example, it will be assumed that a patient was admitted into the St. Mary's facility on Jan. 3, 1997 for some heart monitoring and testing. To this end, referring also to FIG. 6, an admission record memorializing the admission date has been stored on a system DB and is accessible by processor 18. An exemplary ARS 631 corresponding to an ECG DR and the address above is illustrated in FIG. 30 and includes a fixed facility/server field 630, a patient ID field 632, a date field 634, a time field 636 and a fixed report type field or ECG.html field 638.

In addition, it will be assumed that the patient's ID # is "123456789" and that an ECG was performed and a corresponding report was generated on Jan. 5, 1997. Moreover, it is assumed that, prior to admission, several other ECG reports for the same patient were generated and stored on a system DB. Specifically, the prior reports include one report which was generated 20 days prior to admission and another report generated the day before admission (e.g. on Jan. 2, 1997). The ECG report of Jan. 5, 1997 is stored at DB address:

http://hww.st_mary.springfield/123456789/05 01 1997/10:25/ecq.html

Furthermore, referring also to FIG. 29, it is assumed that RR 622 specifies the following rules. First, if an ECG report occurs on the admission date, the ECG report is assumed to be the report to be linked. Second, if more than one ECG report occurs on the admission date, the last of the reports on the admission date is assumed to be the report to be linked. Third, if no ECG reports occur on the admission date, then the temporally next ECG report after the admission date is assumed to be linked if within the POTR (see 620 in FIG. 29). Fourth, if none of the above criteria are met, the temporally subsequent ECG report prior to the admission date is assumed to be linked if within the PRTR. Furthermore, it is assumed a physician is presently using DR literate processor 18, in this case a word processor, to enter text to generate another report corresponding to patient ID #123456789 and that, during data entry, the physician enters the phrase "admission ECG".

Figure 31:
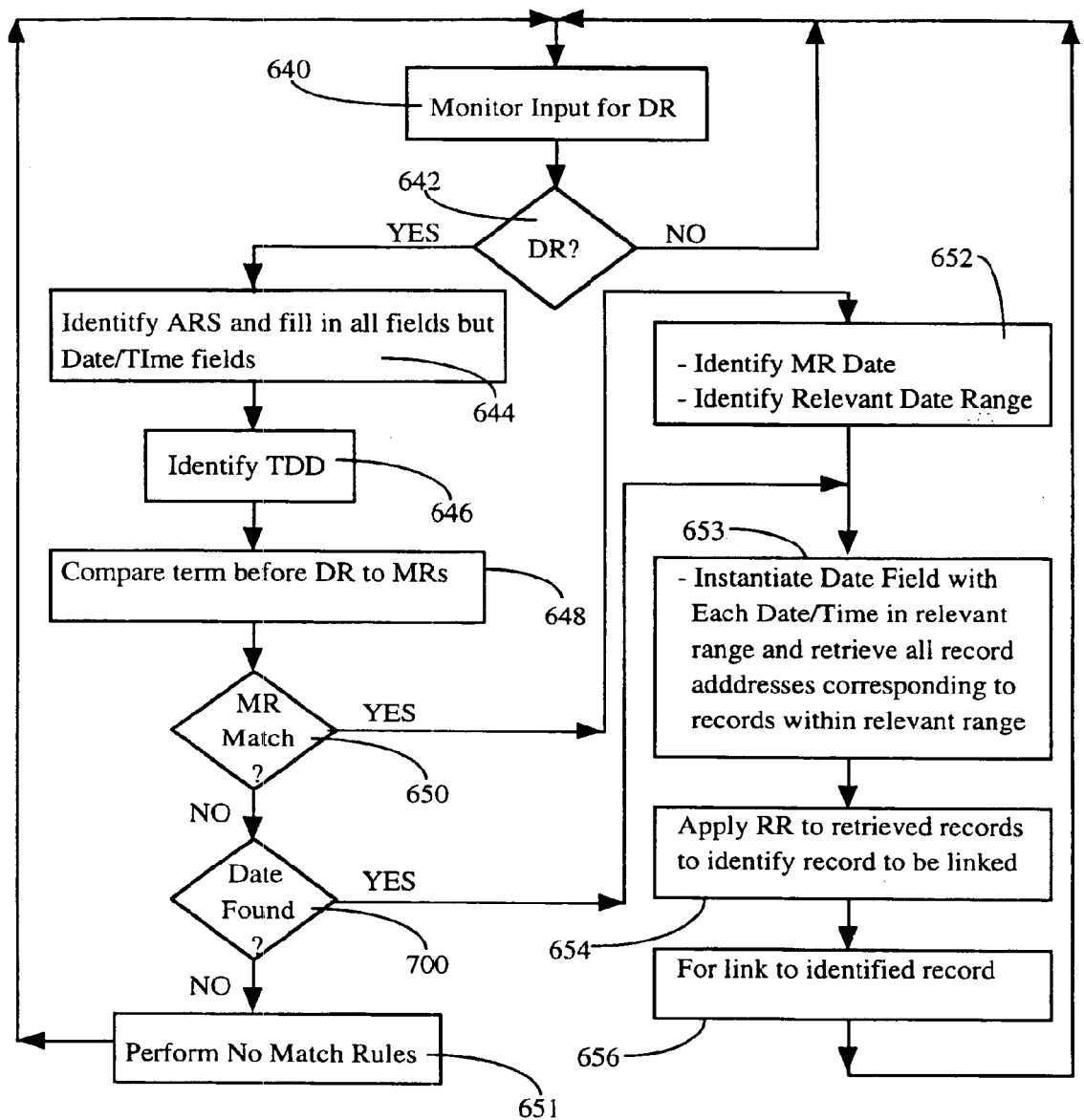
FIG. 31 is a flowchart illustrating operation of a database literate processor which supports modifier references and, which specifically supports temporal modifier references.

Referring also to FIG. 31, a flowchart illustrating exemplary DB literate processor 18 operation as text is entered by the physician is illustrated. At process block 640 processor 18 monitors text entered by the physician searching for any of several supported DRs including the ECG DR. Control loops through blocks 640 and 642 until a DR is identified. At decision block 642, when the ECG DR is entered, processor 18 identifies the ECG DR and performs two distinct but related functions. First, at block 644, processor 18 identifies an ARS corresponding to the ECG DR. In the present example ARS 631 in FIG. 30 is illustrated. In addition, at block 644 processor 18 gleans ARS information and instantiates all ARS fields except for the date and time fields 634 and 636, respectively.

Second, referring also to FIGS. 28 and 29, at block 646 processor 18 accesses table 602 in TRDS 600 (see FIG. 6) and, based on the ECG DR, identifies the corresponding TDD 604. Next, at block 648 processor 18 compares the term or character string immediately preceding the ECG DR in the entered text to each of the MRs in column 608 or until a match is identified.

At decision block 650, if no match is identified (i.e., the term prior to the ECG DR does not match an MR), control passes to block 700.

At block 650 where the term previous to the ECG DR matches an MR, control passes to block 652. In the present example, the term previous to the ECG DR is "admission" which, referring to FIG. 2A, matches MR 612 and therefore control passes to block 652.

At block 652 processor 18 first identifies the date corresponding to admission MR 612 for the particular patient prior to the date of the current report. In the present example, processor 18 identifies the admission date by identifying another ARS corresponding to an admission report, gleaning information for the admission ARS from the record being entered, forming an address to an admission report, accessing the report and gleaning the admission date from the admission report. Although not illustrated, this process is essentially identical to all other address generating methods described above and in previous related applications. In the alternative, the admission address may be sought by accessing an ADT system (not illustrated) which may more readily be able to provide the required date. In the present example, the admission date is identified as Jan. 3, 1997.

In addition, at block 652, processor 18 identifies the PRTR and POTR ranges 618, 620, respectively, and uses ranges 618 and 620 and the admission date to identify a relevant date range for the admission ECG report. In the present example, the date range is three days before and three days after the admission date and therefore is Dec. 21, 1996 through Jan. 6, 1997. After block 652 control passes to process block 653.

Referring still to FIG. 31, at block 700 processor 18 searches the previous input to identify if a specific data for the record to be linked has been provided. If a specific date is identified control passes to block 653. If a specific date is not identified control passes to block 651 where the "no match" rules 626 (see FIG. 29) are performed. In the present example, rules 626 specify that without an MR or specific date, no link should be made and therefore control passes back to block 640 to continue text monitoring.

At block 653 processor 18 sweeps through every date and time combination within the relevant date range and instantiates the ECG address format with each of the date/time combinations to check system DBs for ECG reports for the particular patient which were generated during the relevant date range. Each report address corresponding to an ECG report which is identified as being for the patient within the relevant date range is retrieved and stored in a processor 18 memory. In the present example, one ECG report was generated 20 days prior to admission, a second report was generated one day before admission and the third report was generated two days after admission on Jan. 5, 1997. Thus, of the three ECG reports, processor 18 retrieves addresses corresponding to the January 2 and January 5 reports.

Continuing, at block 654, processor 18 applies the RR 622 to the dates and times of the retrieved records in order to identify one of the retrieved records for linking purposes. To this end, because no ECG reports were generated on the admission date, according to RR 622 the temporally next ECG report after the admission date which is within the relevant date range is assumed to be the report to be linked. In the present case, the ECG report dated Jan. 5, 1997 is the only report having a date which fits this description and therefore, the address corresponding thereto is selected for linkage.

At block 656 a link is formed between the ECG DR and the Jan. 5, 1997 ECG report via the selected address. The link is preferably in the form of a hyperlink wherein the term "ECG" or the phrase "admission ECG" is highlighted within the text and is linked to the selected address such that when the highlighted term is selected (e.g., via a mouse-controlled cursor), the processor accesses the ECG report and provides the report via a display for user observation.

Although a preferred embodiment of the invention for supporting MRs is described above, other embodiments are contemplated. For example, in the present example, when an ECG record is initially stored as soon thereafter, a tag may be provided for the record which indicates the relationship between the record and one or more of the MRs. For instance, when the Jan. 2, 1997 ECG report is initially created, it is contemplated that a processor would not tag the report with respect to an admission MR as no admission date would exist (i.e., in this example admission is on Jan. 3, 1997). However, on Jan. 3, 1997 when the patient is admitted, when an admission record is generated which includes an admission date, the processor would automatically search for patient reports which could be tagged. During this process, referring again to FIG. 29, the processor would apply the TDDs to the Jan. 2, 1997 date of the ECG report. Upon admission the Jan. 5, 1997 report does not exist and therefore, the Jan. 2, 1997 report would be the admission ECG report. Thus, when the admission date is provided, the processor tags the Jan. 2, 1997 report as the admission ECG report. Thereafter, until another ECG report is generated which, based on the RR (see 622 in FIG. 29), supersedes the January 2 report as an admission ECG report when an "admission ECG" DR/MR combination is identified in text, the processor automatically identifies the January 2 report for linking purposes.

Continuing, on Jan. 5, 1997, when the next ECG report for the particular patient is generated, the processor would again apply the ECG TDD (see 604 in FIG. 29) to determine if the new ECG report should be tagged with any of the MRs. In the present example, indeed, based on RR 622 the January 5 report should replace the January 2 report as the admission ECG report and therefore tag correction would occur (i.e., the January 2 report is de-tagged while the January 5 report is tagged as the admission ECG report for the particular patient). Thereafter the January 5 report is used by processor 18 for linking purposes when the "admission ECG" DR/MR combination is identified in entered text.

It should be understood that the methods and apparatuses described above are only exemplary and do not limit the scope of the invention, and that various modifications could be made by those skilled in the art that would fall under the scope of the invention. For example, while the system described above includes only one general data type, clearly systems could be provided which include more than a single general data type. For example, in addition to grouping table entries around patient ID number for linking purposes in related records, table entries may also be grouped around events or procedures such as MRI, PET, NM, etc. procedures. In this case additional general data type definitions would have to be provided.

In addition, while the general data type ARS (see 350 in FIG. 20) is described as including only three fields, the invention contemplates general ARSs which include more than three fields. For example, ARS 350 in FIG. 20 may also include a date field so that a corresponding DR table will only include records or data segments corresponding to a particular patient on a particular date. Then, during DB literate processing, the user would be required to indicate both patient ID and date prior to data entry for linking purposes.

In addition, the invention also contemplates some peripheral aspects related to the general invention. For example, where a DR is identified in information being entered into a document, after a corresponding address is generated, an additional feature causes the address generating processor to search the database for the existence of a record at the generated address and, if the address does not exist, the processor may perform any of several different functions. For instance, where a referenced record does not exists, the processor may indicate to the person entering the data that the record does not exist. In the alterative the processor may simply not cause a link to be formed or may be programmed to provide a list of similar links for user consideration.

Similarly, if, upon generating an address for storage purposes the processor generates an address which is already occupied by a record, the processor may be equipped to recognize this addressing overlap and take any of several different steps to deal with the incongruity.

As another example a billing feature is also contemplated. For instance, assuming a database of specific records which are often useful to facility users is maintained by an outside provider and which is accessible via the internet on a per reference basis. This may be the case, for example, in a law firm which routinely forms links to on-line full text opinion sites in briefs, motions and other documents. In this case, then an opinion is referenced in a brief, a database literate processor forms a link between the reference and the opinion. Therefore, each time the opinion is accessed via a hyperlink, a server which stores the full text opinion automatically generates a bill for the specific access. Referring to FIG. 6, an exemplary billing server 708 is illustrated.

One other peripheral example is that while temporal MRs are described above, the invention contemplates other MR types which can be used to more specifically reference records. For example, a descriptive MR for an "ECG" DR may be "waveform". In this case, when the DR ECG is identified, prior to forming an address, the processor first searches for the "waveform" MR according to specific search rules. If the MR is identified the processor then constructs an address to a record corresponding to the more specific "ECG waveform" combination. The descriptive MRs are similar to the temporal MRs described above except that the descriptive MRs are not time based.

Moreover, while the general data type is described above as being used with a real time DB literate processor, the general data type may also be used with a batch type DB literate processor which receives a complete record and creates links for DRs in the record. In this case when the processor receives a record, the processor initially uses the general data type ARS to identify record information for forming a record address for the DR table record corresponding to the received record, accesses the DR table and then uses the DR table to form links.

Furthermore, it is contemplated that the designating application can be used with all facility applications which are used to view, listen to, generate, etc., date records and segments and to form links to many different data types. To this end, referring again to FIG. 23, icon 426 can be provided as an overlay on virtually all facility screens. For example, when in one text document, if a physician encounters some text the physician would like to reference in some other document, the physician may highlight the desired text and then select icon 426 to earmark the text with a designating DR. Similarly, if an audible heartbeat is stored on a system DB, while listening to the beat, the physician can select icon 426 to earmark the heartbeat.

In addition, while the data type editor is described above as being used to define both an ARS, a corresponding RRS and a corresponding DR, other simpler editors are contemplated which are used to define subsets of the ARS, RRS and DR information. For example, an editor may only be capable of defining an ARS. As another example, an editor may only be capable of defining an ARS and a corresponding DR.

To apprise the public of the scope of this invention, the following claims are made:

What is claimed is:

1. A method using a processor device (PD) linked to a database (DB) and an interface, the DB storing at least a first segment of a first record at a first database address, the method for tagging at least the first segment of the first record for storage and subsequent access, the method comprising the steps of:
   providing the first record for inspection via the interface;
   selecting the first record segment via the interface;
   providing a data reference (DR) via the interface; and
   storing the DR and the first database address in general data type database for subsequent access.

2. The method of claim 1 further including the step of, prior to storing, gleaning information from the first record and using the gleaned information to form a general database address of the general data type database.

3. The method of claim 2 further including the step of providing an address rule set (ARS) that specifies required information and rules to form the general database address wherein the ARS includes at least one fixed address field corresponding to the general data type database and at least one variable address field.

4. The method of claim 3 wherein the step of providing an ARS includes providing an ARS including a single variable field.

5. The method of claim 4 wherein the step of providing a single variable field includes providing a field selected from the group consisting of a patient identifier field, a date field, a procedure field or a record type.

6. The method of claim 3 wherein the ARSs include instantiation rule sets (IRSs) for each address field where each IRS includes a field format which comprises a character string used to instantiate a corresponding field and wherein the character strings for the fixed fields are fixed and the character strings for the variable fields are variable.

7. The method of claim 6 wherein the information to instantiate the variable field is provided in the first record and the step of gleaning includes gleaning the information required to instantiate the variable field.

8. The method of claim 6 wherein each IRS includes a variable search rule set (VSRS), each VSRS specifying at least one condition which must exist for a corresponding field to be instantiated with a corresponding character string, the method further including the step of determining if all of the VSRSs corresponding to an ARS exist and, where all of the VSRSs corresponding to an ARS exist, performing the step of gleaning.

9. The method of claim 8 wherein the VSRS corresponding to the fixed address field requires provision of a DR.

10. The method of claim 2 further including the steps of providing a database including a record rule set (RRS) that specifies required information and rules to form the general data type database, and, after forming the general database address, determining if the general data type database has been stored at the general database address.

11. The method of claim 10 wherein, if the general data type database is stored at the general database address, the step of storing includes updating the general data type database to include the DR and the first database address, else the step of storing includes applying the RRS to glean from the first record at least a sub-set of the information required to form the general data type database, forming the general data type database, storing the general data type database at the general database address and adding the first record segment and corresponding address to the general data type database.

12. The method of claim 11 wherein the RRS specifies a general data type database including a list of DRs and corresponding addresses, the step of forming the general data type database includes forming the general data type database and the step of updating includes adding a DR and corresponding address to the table.

13. The method of claim 1 further including limiting modifications to the first record segment after the DR is provided.

14. The method of claim 13 wherein the step of limiting includes marking the first record segment so that first record segment deletion is limited.

15. The method of claim 3 wherein the general data type database is a first general data type database type for storing record segments of a first general type and the corresponding ARS is a first ARS and wherein the method further includes the step of providing a second ARS corresponding to a second general data type database type that specifies required information and rules to form a second general database address for a second general data type database, the second general data type database for storing record segments of a second general type, prior to storing, identifying the first record segment as one of the general types, identifying the ARS corresponding to the identified type, gleaning at least a sub-set of the information required for the identified ARS from the first record and forming a general database address corresponding to the ARS.

16. The method of claim 15 wherein the step of identifying the first record segment as one of the first and second types includes providing a general type selection and receiving a selection of type via the interface.

17. The method of claim 1 wherein the interface includes a display screen and wherein the step of providing the first record includes providing the first record via the display screen.

18. The method of claim 17 wherein the step of selecting includes selecting the first record segment on the display screen.

19. The method of claim 18 also for use with an interface including an input device and wherein the step of providing a DR includes using the input device to indicate, via the screen, the DR.

20. The method of claim 19 wherein the step of indicating includes providing an information box on the display screen and providing the DR in the information box.

21. The method of claim 4 also for generating links between instances of the DR in a second record and the first record segment, the method further including, after the DR and first segment address have been stored, searching the second record for instances of the DR and, where an instance of the DR is identified, rendering the first segment accessible via the second record.

22. The method of claim 21 further including the steps of, prior to searching the second record, gleaning the information required by the ARS from the second record, forming thegeneral database addressusing the gleaned information and accessing the DR in the general data type database.

23. The method of claim 2 further including the step of forming the general data type database and storing the general data type database at the general database address.

24. The method of claim 2 also for use with a second record wherein the second record includes information from which the general database address can be identified, the method further including the step of, when the second record is accessed, gleaning information from the second record, using the gleaned information to form the general database address and accessing the general data type database.

25. The method of claim 24 wherein the second record includes information from which a second general database address corresponding to a second general data type database can be identified, the method further including the step of, when the second record is accessed, using gleaned information to form the second general database address and accessing the second general data type database.

26. The method of claim 24 further including the step of, after the general data type database has been accessed, determining if one of the DRs in the data type database is present in the second record.

27. The method of claim 26 wherein, when a DR is present in the second record, the method further includes the step of rendering the first segment accessible via the second record.

28. The method of claim 25 further including the steps of determining if one of the DRs in either of the first or second general data type databases is present in the second record and, if a DR is present in the second record, rendering the first segment accessible via the second record.

29. The method of claim 28 wherein, if DRs from the first and second general data type databases overlap, the method further includes the step of rendering the segment corresponding to the first general data type database accessible in the second record.

30. The method of claim 27 wherein the step of rendering includes using markup language codes to associate the DR in the second record with the first record segment.

31. The method of claim 2 wherein the general data type database is a first database, the method is also for use with at least a second database type and at least a second record, the second database type including address rule sets (ARSs) that specify required information and rules to form database addresses for specific records, the method further including the steps of, when the second record is accessed, gleaning information from the second record and using the gleaned information to form at least one of the general database address and an address corresponding to one of the ARSs in the second database and accessing the corresponding one of the general data type database and the record.

32. The method of claim 31 wherein the second database includes a separate DR corresponding to each of the ARSs and wherein the step of gleaning includes identifying a DR in the second record, accessing the ARS corresponding to the identified DR, identifying the information required to instantiate the accessed ARS and gleaning the information required to instantiate the accessed ARS from the second record.

33. The method of claim 32 wherein the step of accessing the corresponding one of the general data type database-and the record includes, when the corresponding one is the general data type database, identifying the DRs in the general data type database, searching for each identified DR in the second record and, when one of the identified DRs is identified, associating the identified DR with the corresponding record address.

34. The method of claim 32 wherein the step of accessing the corresponding one of the general data type database and the record includes, when the corresponding one is a record, accessing the record and rendering the record accessible via the second record.

35. A method for using a processor device (PD) to form links between data references (DRs) in a first record and records referenced by the DRs, the method comprising the steps of:

storing the DRs in at least first and second data type databases wherein at least the first of the databases is a general type database, each DR in the first data type database associated with a database address;

receiving the first record;

accessing the DRs in the first general data type database;

searching the first record for any of the DRs in the first data type database; and when a first data type database DR is located, forming a link between the DR and the record corresponding to the database address associated with the DR.

36. The method of claim 35 wherein the second data type database is also a general data type database where each DR is associated with a specific record address, the method further including the steps of searching the first record for any of the second data type database DRs and, and when a second data type database DR is located, forming a link between the DR and the record corresponding to the database address associated with the DR.

37. The method of claim 35 further including the step of determining if the first record is associated with the first data type database and only accessing the first data type database when the first record is associated therewith.

38. The method of claim 35 wherein the second data type database includes DRs and associated address rule sets (ARSs) that specify required information and rules to form database addresses for specific records, the method further including the steps of searching the first record for any of the second data type database DRs and, where a second data type database DR is identified, identifying the information required by a corresponding ARS, gleaning the required information from the first record, using the gleaned information to form a record address according to the ARS and accessing the record stored at the formed record address.

39. The method of claim 38 wherein the step of accessing including rendering the record stored at the formed record address accessible in the first record.

40. A method for using a processor device (PD) to form links between data references (DRs) in a first record and records referenced by the DRs, the DRs stored in a plurality of general data type databases, each DR associated with a database record address and each of the general data type databases associated with a sub-set of information, the method comprising the steps of:

receiving the first record;

gleaning information from the first record;

identifying each general data type database that includes an information sub-set that is common with the gleaned information;

accessing the DRs in each identified general data type database;

comparing the accessed DRs to the content of the first record; and when any DR is located in the first record, rendering the record associated with the DR accessible.

41. The method of claim 40 where accessed DRs are unique so the step of rendering includes rendering only a single record.

42. The method of claim 40 where each accessed DR is compared to the first record content, and for every DR that occurs in the first record the method includes linking the DR occurring in the first record to the corresponding record.

43. The method of claim 40 further including the step of accessing at least one other data type database that is not dependent on information gleaned from the first record segment.

44. The method of claim 43 wherein the at least one other data type database includes a list of DRs and corresponding address rule sets (ARSs) that specify required information and rules to form database addresses for specific records, the method further including the steps of, searching the first record for any of the other data type database DRs and, where an other data type database DR is identified, identifying the information required by a corresponding ARS, gleaning the required information from the first record, using the gleaned information to form a record address according to the ARS and accessing the record stored at the formed record address.

* * * * *